US012595271B2

(12) United States Patent
Stoessel et al.

(10) Patent No.: US 12,595,271 B2
(45) Date of Patent: Apr. 7, 2026

(54) AROMATIC COMPOUNDS FOR ORGANIC ELECTROLUMINESCENT DEVICES

(71) Applicant: UDC IRELAND LIMITED, Dublin (IE)

(72) Inventors: Philipp Stoessel, Darmstadt (DE); Rouven Linge, Darmstadt (DE)

(73) Assignee: UDC IRELAND LIMITED, Dublin (IE)

( * ) Notice: Subject to any disclaimer, the term of this patent is extended or adjusted under 35 U.S.C. 154(b) by 819 days.

(21) Appl. No.: 17/785,421

(22) PCT Filed: Dec. 15, 2020

(86) PCT No.: PCT/EP2020/086134

§ 371 (c)(1),
(2) Date: Jun. 15, 2022

(87) PCT Pub. No.: WO2021/122538

PCT Pub. Date: Jun. 24, 2021

(65) Prior Publication Data

US 2023/0069061 A1 Mar. 2, 2023

(30) Foreign Application Priority Data

Dec. 18, 2019 (EP) .................................... 19217614

(51) Int. Cl.

| | |
|---|---|
| ***C07F 5/02*** | (2006.01) |
| ***C07D 221/18*** | (2006.01) |
| ***C07D 265/34*** | (2006.01) |
| ***C07D 279/14*** | (2006.01) |
| ***C09K 11/06*** | (2006.01) |
| ***H10K 50/11*** | (2023.01) |
| ***H10K 85/60*** | (2023.01) |

(52) U.S. Cl.

CPC ............ *C07F 5/027* (2013.01); *C07D 221/18* (2013.01); *C07D 265/34* (2013.01); *C07D 279/14* (2013.01); *C09K 11/06* (2013.01); *H10K 85/657* (2023.02); *H10K 85/6572* (2023.02); *H10K 85/658* (2023.02); *C09K 2211/1018* (2013.01); *C09K 2211/104* (2013.01); *H10K 50/11* (2023.02)

(58) Field of Classification Search

CPC .... C07F 5/027; H10K 85/658; H10K 85/657; H10K 85/6572; C07D 221/18; C07D 265/34; C09K 11/06

USPC .................................................... 252/301.16

See application file for complete search history.

(56) References Cited

FOREIGN PATENT DOCUMENTS

| | | | |
|---|---|---|---|
| CN | 110573516 | A | 12/2019 |
| CN | 111410952 | A | 7/2020 |
| WO | 2019/009687 | A1 | 1/2019 |
| WO | 2019/132506 | A1 | 7/2019 |

OTHER PUBLICATIONS

Dral et al., "Doped Polycyclic Aromatic Hydrocarbons as Building Blocks for Nanoelectronics: A Theoretical Study", Journal Of Organic Chemistry, vol. 78, No. 5, 2012, pp. 1894-1902.

International Search Report and Written Opinion received for PCT Patent Application No. PCT/EP2020/086134, mailed on Feb. 10, 2021, 12 pages (3 pages of English Translation and 9 pages of Original Document).

Tran et al., "[pi]-Stacking Behavior of Selected Nitrogen-Containing PAHs" The Journal of Physical Chemistry A, vol. 108, No. 42, 2004, pp. 9155-9160.

Wang et al., "Exploration of pyrazine -embedded antiaromatic polycyclic hydrocarbons generated by solution and on-surface azomethine ylide homocoupling" Nature Communication, vol. 8, No. 1, 2017, pp. 1-7.

Casanovas et al., "Origin of the Large N 1s Binding Energy in X-ray Photoelectron Spectra of Calcined Carbonaceous Materials", J. Am. Chem. Soc, vol. 118, No. 34, 1996, pp. 8071-8076.

*Primary Examiner* — Anita Nassiri-Motlagh
(74) *Attorney, Agent, or Firm* — DUANE MORRIS LLP

(57) ABSTRACT

The invention relates to compounds which are suitable for use in electronic devices, and to electronic devices, in particular organic electroluminescent devices, containing said compounds.

18 Claims, No Drawings

AROMATIC COMPOUNDS FOR ORGANIC ELECTROLUMINESCENT DEVICES

CROSS-REFERENCE TO RELATED APPLICATIONS

This application is a national stage application (under 35 U.S.C. § 371) of PCT/EP2020/086134, filed Dec. 15, 2020, which claims benefit of European Application No. 19217614.7, filed Dec. 18, 2019, both of which are incorporated herein by reference in their entirety.

The present invention relates to aromatic compounds for use in electronic devices, especially in organic electroluminescent devices, and to electronic devices, especially organic electroluminescent devices, comprising these polycyclic compounds.

Emitting materials used in organic electroluminescent devices are frequently phosphorescent organometallic complexes or fluorescent compounds. There is generally still a need for improvement in electroluminescent devices.

WO 2010/104047 A1 and WO 2019/132506 A1 disclose polycyclic compounds that can be used in organic electroluminescent devices. There is no disclosure of compounds according to the present invention. In addition, antiaromatic properties of compounds are examined by Wang et al., Nature Communications, 2017, 8, 1948. However, there is no description of the use of these compounds in organic electroluminescent devices by Wang et al.

In general terms, there is still a need for improvement in these polycyclic compounds, for example for use as emitters, especially as fluorescent emitters, particularly in relation to lifetime and color purity, but also in relation to the efficiency and operating voltage of the device.

It is therefore an object of the present invention to provide compounds which are suitable for use in an organic electronic device, especially in an organic electroluminescent device, and which lead to good device properties when used in this device, and to provide the corresponding electronic device.

More particularly, the problem addressed by the present invention is that of providing compounds which lead to a high lifetime, good efficiency and low operating voltage.

In addition, the compounds should have excellent processibility, and the compounds should especially show good solubility.

A further problem addressed by the present invention can be considered that of providing compounds suitable for use in phosphorescent or fluorescent electroluminescent devices, especially as emitter. More particularly, a problem addressed by the present invention is that of providing emitters suitable for red, green or blue electroluminescent devices.

In addition, the compounds, especially when they are used as emitters in organic electroluminescent devices, should lead to devices having excellent color purity.

A further problem can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds described in detail below solve this problem and are of good suitability for use in electroluminescent devices and lead to improvements in the organic electroluminescent devices, especially in relation to lifetime, color purity, efficiency and operating voltage. The present invention therefore provides these compounds and electronic devices, especially organic electroluminescent devices, comprising such compounds.

The present invention provides a compound comprising at least one structure of the formula (Ia) and/or (Ib), preferably a compound of the formula (Ia) and/or (Ib):

Formula (Ia)

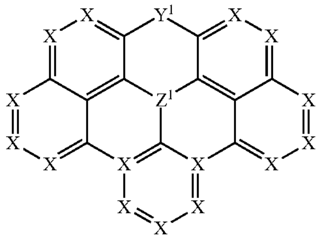

Formula (Ib)

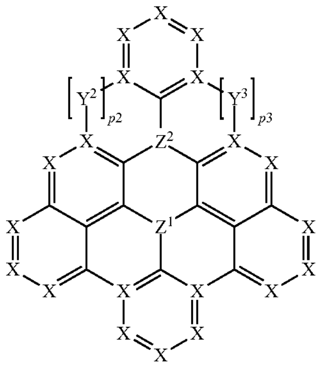

where the symbols and indices used are as follows:

$Z^1$, $Z^2$ is the same or different at each instance and is N, P, B, Al, P(═O), P(═S), or Ga, preferably N, B or Al, more preferably N or B;

$Y^1$, $Y^2$, $Y^3$ is the same or different at each instance and is a bond, N(Ar), N(R), P(Ar), P(R), P(═O)Ar, P(═O)R, P(═S)Ar, P(═S)R, B(Ar), B(R), Al(Ar), Al(R), Ga(Ar), Ga(R), C═O, $C(R)_2$, $Si(R)_2$, C═NR, C═NAr, C═$C(R)_2$, O, S, Se, S═O, or $SO_2$, preferably a bond, N(Ar), N(R), B(Ar), B(R), P(═O)R, P(═O)Ar, C═O, $C(R)_2$, O, S, S═O, or $SO_2$, more preferably a bond, $C(R)_2$, O, S, C═O, N(Ar) or B(Ar);

$p^2$, $p^3$ are the same or different and are 0 or 1;

X is N, CR, or C if a $Y^1$, $Y^2$ or $Y^3$ group binds thereto, with the proviso that not more than two of the X groups in one cycle are N;

R is the same or different at each instance and is H, D, OH, F, Cl, Br, I, CN, $NO_2$, $N(Ar)_2$, $N(R^1)_2$, C(═O)$N(Ar)_2$, C(═O)$N(R^1)_2$, $C(Ar)_3$, $C(R^1)_3$, $Si(Ar)_3$, $Si(R^1)_3$, $B(Ar)_2$, $B(R^1)_2$, C(═O)Ar, C(═O)$R^1$, P(═O)$(Ar)_2$, P(═O)$(R^1)_2$, $P(Ar)_2$, $P(R^1)_2$, S(═O)Ar, S(═O)$R^1$, S(═O)$_2$Ar, S(═O)$_2R^1$, $OSO_2Ar$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more non-adjacent $CH_2$ groups may be replaced by $R^1C$═$CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R radicals may also together form a ring system;

Ar is the same or different at each instance and is an aromatic or heteroaromatic ring system which has 5 to 60 aromatic ring atoms and may be substituted by one or more $R^1$ radicals; at the same time, it is possible for two Ar radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C═O, $C{=}NR^1$, $C{=}C(R^1)_2$, O, S, S═O, $SO_2$, $N(R^1)$, $P(R^1)$ and $P(=O)R^1$;

$R^1$ is the same or different at each instance and is H, D, F, Cl, Br, I, CN, $NO_2$, $N(Ar')_2$, $N(R^2)_2$, C(═O)Ar', $C(=O)R^2$, $P(=O)(Ar')_2$, $P(Ar')_2$, $B(Ar')_2$, $B(R^2)_2$, $C(Ar')_3$, $C(R^2)_3$, $Si(Ar')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more non-adjacent $CH_2$ groups may be replaced by $-R^2C{=}CR^2-$, —C≡C—, $Si(R^2)_2$, C═O, C═S, C═Se, $C{=}NR^2$, —C(═O)O—, $-C(=O)NR^2-$, $NR^2$, $P(=O)(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent $R^1$ radicals together may form a ring system; at the same time, one or more $R^1$ radicals may form a ring system with a further part of the compound;

Ar' is the same or different at each instance and is an aromatic or heteroaromatic ring system which has 5 to 30 aromatic ring atoms and may be substituted by one or more $R^2$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C═O, $C{=}NR^2$, $C{=}C(R^2)_2$, O, S, S═O, $SO_2$, $N(R^2)$, $P(R^2)$ and $P(=O)R^2$, $R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, preferably adjacent substituents $R^2$ together may form a ring system.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An electron-deficient heteroaryl group in the context of the present invention is a heteroaryl group having at least one heteroaromatic six-membered ring having at least one nitrogen atom. Further aromatic or heteroaromatic five-membered or six-membered rings may be fused onto this six-membered ring. Examples of electron-deficient heteroaryl groups are pyridine, pyrimidine, pyrazine, pyridazine, triazine, quinoline, quinazoline or quinoxaline.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a non-aromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 20 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 or 5-40 aromatic ring atoms and may also be substituted in each case by the abovementioned radicals and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

The wording that two or more radicals together may form a ring, in the context of the present description, should be understood to mean, inter alia, that the two radicals are joined to one another by a chemical bond with formal elimination of two hydrogen atoms. This is illustrated by the following scheme:

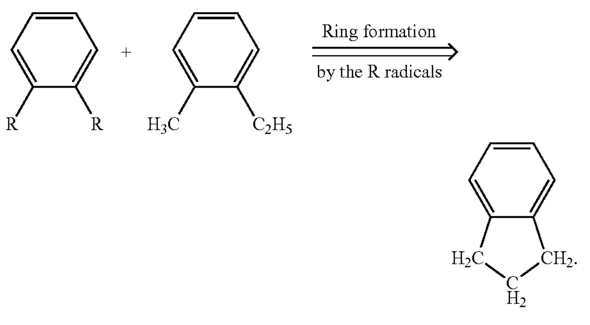

In addition, however, the abovementioned wording shall also be understood to mean that, if one of the two radicals is hydrogen, the second radical binds to the position to which the hydrogen atom was bonded, forming a ring. This will be illustrated by the following scheme:

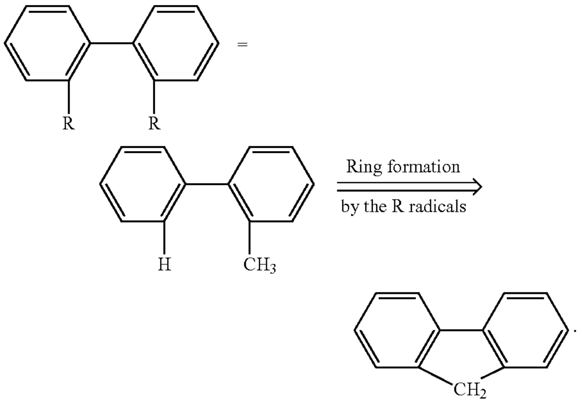

In a preferred configuration, the compounds of the invention may comprise a structure of the formulae (IIa), (IIb), (IIc) and/or (IId); more preferably, the compounds of the invention may be selected from the compounds of the formulae (IIa), (IIb), (IIc) and/or (IId):

Formula (IIa)

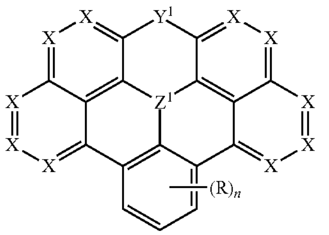

Formula (IIb)

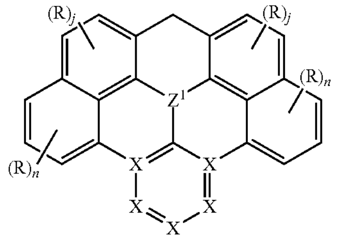

Formula (IIc)

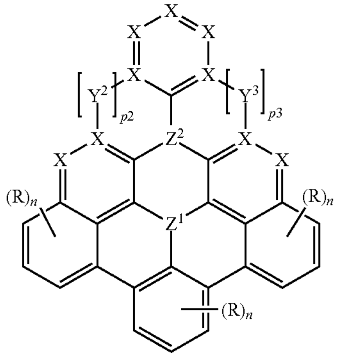

-continued

Formula (IId)

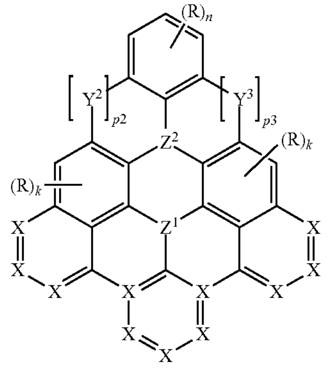

where $p^2$, $p^3$, $Y^1$, $Y^2$, $Y^3$, X, $Z^1$, $Z^2$ and R have the definitions given above, especially for formula (Ia) and/or (Ib), the index n is 0, 1, 2 or 3, preferably 0, 1 or 2, the index j is 0, 1 or 2, preferably 0 or 1, and the index k is 0 or 1, preferably 0, where the sum total of the indices k, j and n is preferably 0, 1, 2, 3, 4, 5 or 6.

It may preferably be the case that, in the formulae (Ia), (Ib), (IIa), (IIb), (IIc) and (IId), not more than four, preferably not more than two, X group(s) are N; more preferably, all X groups are CR.

In a further preferred embodiment, it may be the case that the compounds of the invention comprise a structure of the formulae (IIIa), (IIIb), (IIIc) and/or (IIId), where the compounds of the invention may more preferably be selected from the compounds of the formulae (IIIa), (IIIb), (IIIc) and/or (IIId):

Formula (IIIa)

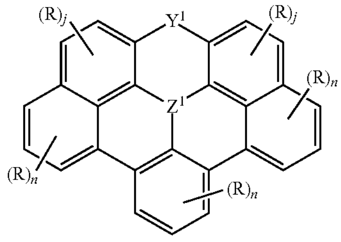

Formula (IIIb)

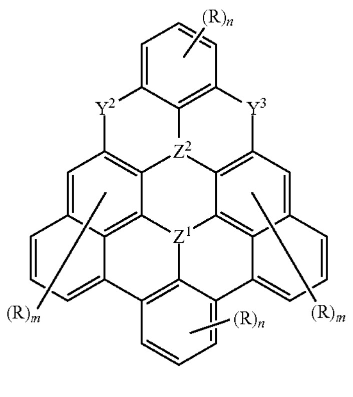

-continued

Formula (IIIc)

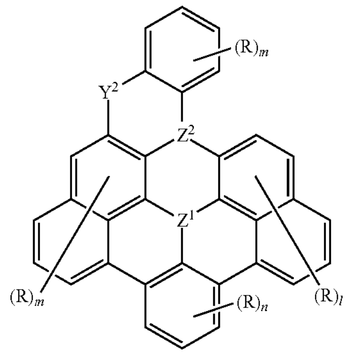

Formula (IIId)

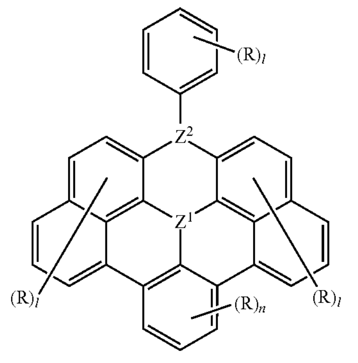

where $Y^1$, $Y^2$, $Y^3$, X, $Z^1$, $Z^2$ and R have the definitions given above, especially for formula (Ia) and/or (Ib), the index l is 0, 1, 2, 3, 4 or 5, preferably 0, 1 or 2, the index l is 0, 1, 2, 3, 4 or 5, preferably 0, 1 or 2, the index m is 0, 1, 2, 3 or 4, preferably 0, 1 or 2, and the index n is 0, 1, 2 or 3, preferably 0, 1 or 2, where the sum total of the indices l, m and n is preferably 2, 3, 4, 5, 6, 7 or 8, preference being given to structures of the formulae (IIIa) and (IIIb), and particular preference to structures of the formula (IIIa).

The sum total of the indices m, n and l in structures/compounds of the formulae (IIIa), (IIIb), (IIIc) and (IIId) is preferably not more than 10, especially preferably not more than 8 and more preferably not more than 6.

In addition, in formulae including (Ia), (Ib), (IIa), (IIb), (IIc), (IId), (IIIa), (IIIb), (IIIc), (IIId) and/or the preferred embodiments of these formulae set out hereinafter, it may be the case that, if $Z^1$ is N, $Y^1$ is not N(Ar), N(R), or, if $Z^1$ is N, $Z^2$ is not N.

Moreover, in formulae including (Ia), (Ib), (IIa), (IIb), (IIc), (IId), (IIIa), (IIIb), (IIIc), (IIId) and/or the preferred embodiments of these formulae set out hereinafter, it may be the case that, if $Z^1$ is N and $Y^1$ is N(Ar), compounds are excluded in which the Ar group of the N(Ar) radical represented by $Y^1$, together with four R radicals derived from X groups of the ring systems to which the $Y^1$ radical binds, forms an aromatic ring system where any two of the four X groups are adjacent.

In a further configuration, in formulae including (Ia), (Ib), (IIa), (IIb), (IIc), (IId), (IIIa), (IIIb), (IIIc), (IIId) and/or the preferred embodiments of these formulae set out hereinafter, it may be the case that $Z^1$ is selected from N and P and the $Y^1$ group is P(═O)Ar, P(═O)R, B(Ar), B(R), Al(Ar), Al(R), Ga(Ar), Ga(R), C═O, S═O or $SO_2$, preferably B(Ar), B(R), P(=O)Ar, P(=O)R, C=O, S=O or $SO_2$, more preferably B(R) or B(Ar), or that $Z^1$ is selected from N and P and the $Z^2$ group is B, Al, P(=O), P(=S) or Ga, preferably B, Al or P(=O), more preferably B, or that $Z^2$ is selected from N and P and at least one of the $Y^2$, $Y^3$ groups is P(=O)Ar, P(=O)R, B(Ar), B(R), Al(Ar), Al(R), Ga(Ar), Ga(R), C=O, S=O or $SO_2$, preferably B(Ar), B(R), P(=O)Ar, P(=O)R, C=O, S=O or $SO_2$, more preferably B(R) or B(Ar).

In a further configuration, in formulae including (Ia), (Ib), (IIa), (IIb), (IIc), (IId), (IIIa), (IIIb), (IIIc), (IIId) and/or the preferred embodiments of these formulae set out hereinafter, it may be the case that $Z^1$ is selected from B, Al, P(=O), P(=S) and Ga and the $Y^1$ group is N(Ar), N(R), P(Ar), P(R), O, S or Se, preferably N(Ar), N(R), O or S, more preferably N(Ar), or that $Z^1$ is selected from B, Al, P(=O), P(=S) and Ga, and the $Z^2$, $Y^3$ group is N or P, preferably N or P, more preferably N;

that $Z^2$ is selected from B, Al, P(=O), P(=S) and Ga, and at least one of the $Y^2$, $Y^3$ groups is N(Ar), N(R), P(Ar), P(R), O, S or Se, preferably N(Ar), N(R), O or S, more preferably N(Ar).

More preferably, $Z^1$ and/or $Z^2$ is B. In addition, $Z^1$ and/or $Z^2$ is more preferably N. In an especially preferred configuration, one of the $Z^1$ and $Z^2$ groups is B and one of the $Z^1$ and $Z^2$ groups is N.

In a preferred development of the present invention, it may be the case that at least two R radicals form a fused ring together with the further groups to which the two R radicals bind, where the two R radicals form at least one structure of the formulae (RA-1) to (RA-12):

Formula RA-1

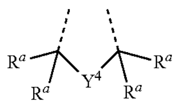

Formula RA-2

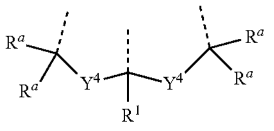

Formula RA-3

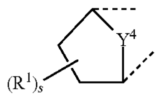

Formula RA-4

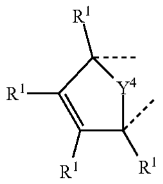

Formula RA-5

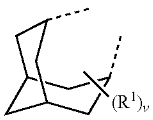

-continued

Formula RA-6

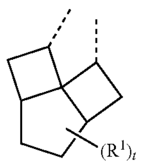

Formula RA-7

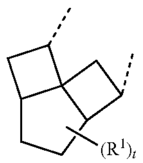

Formula RA-8

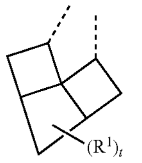

Formula RA-9

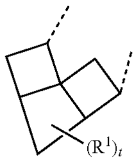

Formula RA-10

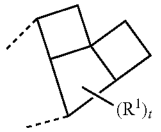

Formula RA-11

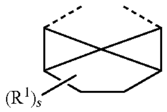

Formula RA-12

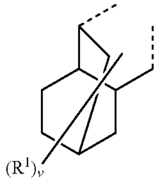

where $R^1$ has the definition set out above, the dotted bonds represent the sites of attachment to the atoms of the groups to which the two R radicals bind, and the further symbols have the following definition:

$Y^4$ is the same or different at each instance and is $C(R^1)_2$, $(R^1)_2C—C(R^1)_2$, $(R^1)C=C(R^1)$, $NR^1$, NAr, O or S, preferably $C(R^1)_2$, $(R^1)_2C—C(R^1)_2$, $(R^1)C=C(R^1)$, O or S;

$R^a$ is the same or different at each instance and is F, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more non-adjacent $CH_2$ groups may be replaced by $R^2C=CR^2$, C≡C, $Si(R^2)_2$, C=O, C=S, C=Se, $C=NR^2$, —O(=O)O—, $—C(=O)NR^2—$, $NR^2$, $P(=O)(R^1)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; at the same time, it is also possible for two $R^a$ radicals together to form a ring system;

s is 0, 1, 2, 3, 4, 5 or 6, preferably 0, 1, 2, 3 or 4, more preferably 0, 1 or 2;

t is 0, 1, 2, 3, 4, 5, 6, 7 or 8, preferably 0, 1, 2, 3 or 4, more preferably 0, 1 or 2;

v is 0, 1, 2, 3, 4, 5, 6, 7, 8 or 9, preferably 0, 1, 2, 3 or 4, more preferably 0, 1 or 2.

It may further be the case that the at least two R radicals that form structures of the formulae (RA-1) to (RA-12) and form a fused ring are R radicals from adjacent X groups.

In a preferred embodiment of the invention, the at least two R radicals form a fused ring together with the further groups to which the two R radicals bind, where the two R radicals preferably form at least one of the structures of the formulae (RA-1a) to (RA-4f):

Formula RA-1a

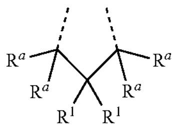

Formula RA-1b

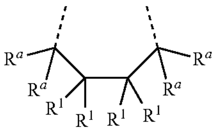

Formula RA-1c

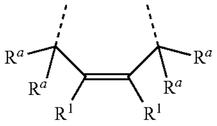

Formula RA-2a

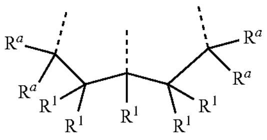

Formula RA-2b

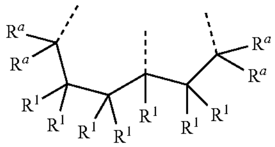

Formula RA-2c

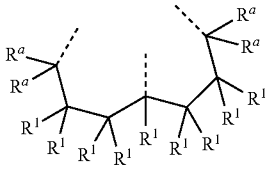

Formula RA-3a

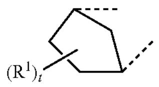

-continued

Formula RA-3b

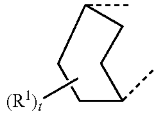

Formula RA-4a

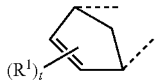

Formula RA-4b

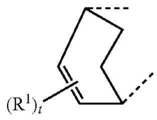

Formula RA-4c

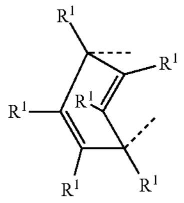

Formula RA-4d

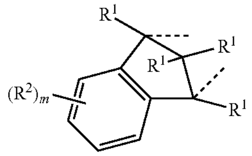

Formula RA-4e

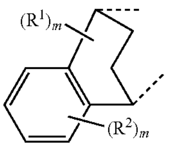

Formula RA-4f

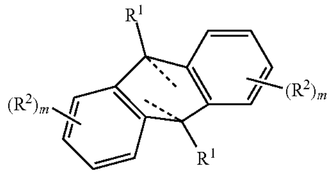

where the symbols $R^a$ and $R^1$ and the indices s and t have the definitions given above, especially for formulae (RA-1) to (RA-12), and the index m is 0, 1, 2, 3 or 4, preferably 0, 1 or 2.

In a further-preferred configuration, at least two R radicals form a fused ring together with the further groups to which the two R radicals bind, where the two R radicals form structures of the formula (RB):

Formula RB

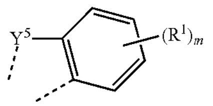

where $R^1$ has the definition set out above, especially for formula (Ia) and/or (Ib), the index m is 0, 1, 2, 3 or 4, preferably 0, 1 or 2, and $Y^5$ is $C(R^1)_2$, $NR^1$, NAr, O or S, preferably $C(R^1)_2$, NAr or O.

It may be the case here that the at least two R radicals that form structures of the formula (RB) and form a fused ring are R radicals from adjacent X groups.

More preferably, the compounds include at least one structure of the formulae (IVa) to (IVr); more preferably, the compounds are selected from compounds of the formulae (IVa) to (IVr), where the compounds have at least one fused ring:

Formula (IVa)

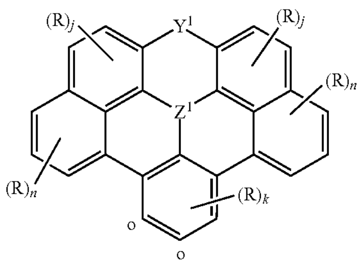

Formula (IVb)

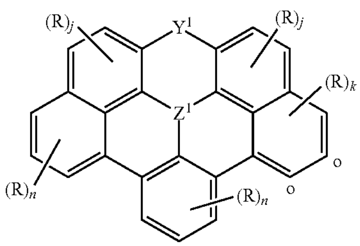

Formula (IVc)

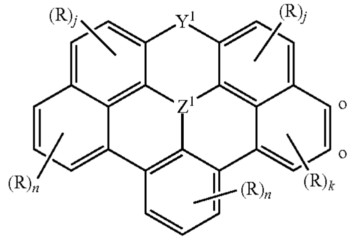

Formula (IVd)

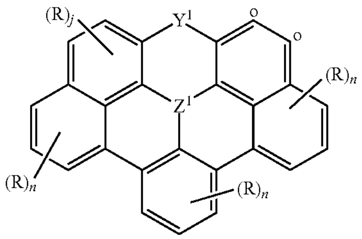

Formula (IVe)

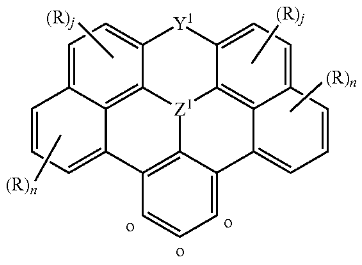

-continued

Formula (IVf)

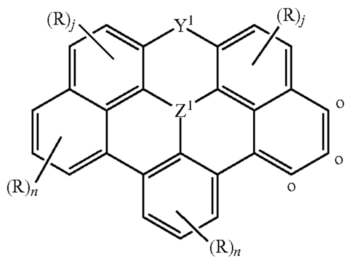

Formula (IVg)

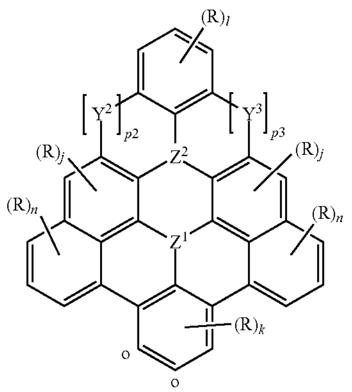

Formula (IVh)

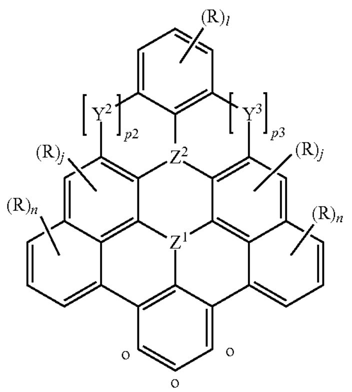

Formula (IVi)

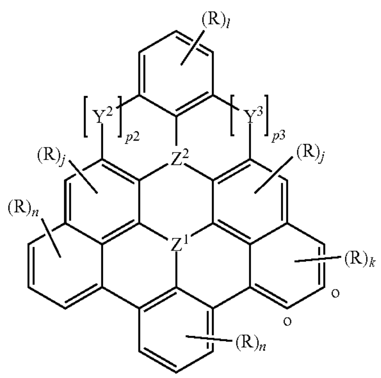

-continued
Formula (IVj)
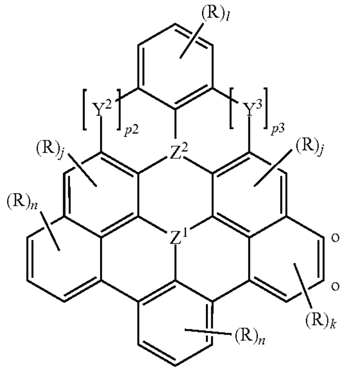
Formula (IVk)
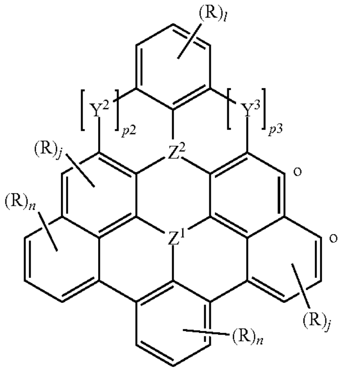
Formula (IVm)
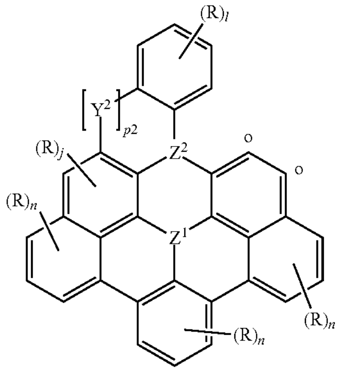
Formula (IVn)
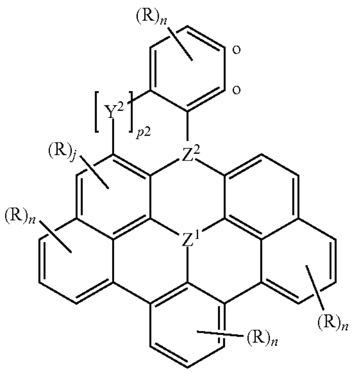
-continued
Formula (IVo)
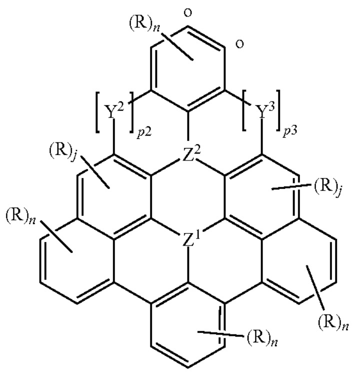
Formula (IVp)
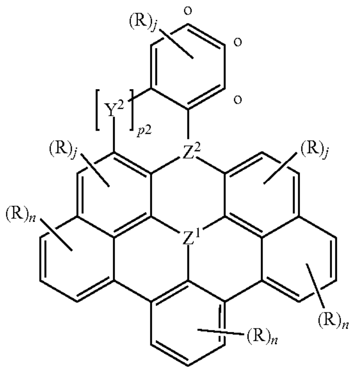
Formula (IVq)
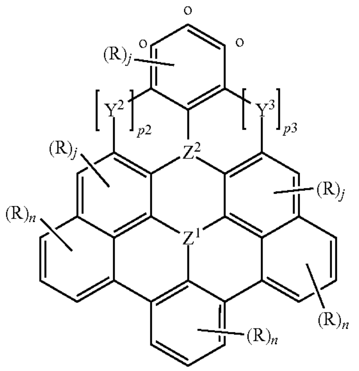
Formula (IVr)
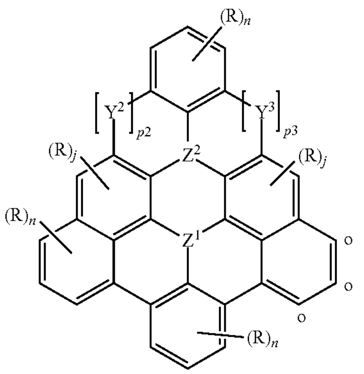
where $Y^1$, $Y^2$, $Y^3$, X, $Z^1$, $Z^2$ and R have the definitions given above, especially for formula (Ia) and/or (Ib), the symbol o represents the sites of attachment of the fused ring, the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, the index j is 0, 1 or 2, preferably 0 or 1, and the index k is 0 or 1, preferably 0, where the sum total of the indices k, j, l, m and n is preferably 0, 1, 2, 3, 4, 5 or 6. Preference is given here to structures/compounds of the formulae (IVa) to (IVk), and particular preference to structures/compounds of the formulae (IVa) to (IVd).

The fused ring, especially in formulae (IVa) to (IVr), is preferably formed by at least one of the structures of the formulae (RA-1) to (RA-12), of the formulae (RA-1a) to (RA-4f) and/or of the formula (RB), together with the ring atoms marked by the symbol o, particular preference being given to structures of the formulae (RA-1) to (RA-12), of the formulae (RA-1a) to (RA-4f).

In preferred embodiments, the compounds include structures having the features that follow, with ring formation on the base structure shown in the table that follows according to the structures shown below, and selected according to the criteria that follow.

| | Base structure | Ring formation formula |
|---|---|---|
| Formula (IVa-1) | Formula (IVa) | (RA-1) |
| Formula (IVa-2) | Formula (IVa) | (RA-1a) |
| Formula (IVa-3) | Formula (IVa) | (RA-1b) |
| Formula (IVa-4) | Formula (IVa) | (RA-1c) |
| Formula (IVa-5) | Formula (IVa) | (RA-3) |
| Formula (IVa-6) | Formula (IVa) | (RA-3a) |
| Formula (IVa-7) | Formula (IVa) | (RA-3b) |
| Formula (IVa-8) | Formula (IVa) | (RA-4) |
| Formula (IVa-9) | Formula (IVa) | (RA-4a) |
| Formula (IVa-10) | Formula (IVa) | (RA-4b) |
| Formula (IVa-11) | Formula (IVa) | (RA-4c) |
| Formula (IVa-12) | Formula (IVa) | (RA-4d) |
| Formula (IVa-13) | Formula (IVa) | (RA-4e) |
| Formula (IVa-14) | Formula (IVa) | (RA-4f) |
| Formula (IVa-15) | Formula (IVa) | (RA-5) |
| Formula (IVa-16) | Formula (IVa) | (RA-6) |
| Formula (IVa-17) | Formula (IVa) | (RA-7) |
| Formula (IVa-18) | Formula (IVa) | (RA-8) |
| Formula (IVa-19) | Formula (IVa) | (RA-9) |
| Formula (IVa-20) | Formula (IVa) | (RA-10) |
| Formula (IVa-21) | Formula (IVa) | (RA-11) |
| Formula (IVa-22) | Formula (IVa) | (RA-12) |
| Formula (IVa-23) | Formula (IVa) | (RB) |
| Formula (IVb-1) | Formula (IVb) | (RA-1) |
| Formula (IVb-2) | Formula (IVb) | (RA-1a) |
| Formula (IVb-3) | Formula (IVb) | (RA-1b) |
| Formula (IVb-4) | Formula (IVb) | (RA-1c) |
| Formula (IVb-5) | Formula (IVb) | (RA-3) |
| Formula (IVb-6) | Formula (IVb) | (RA-3a) |
| Formula (IVb-7) | Formula (IVb) | (RA-3b) |
| Formula (IVb-8) | Formula (IVb) | (RA-4) |
| Formula (IVb-9) | Formula (IVb) | (RA-4a) |
| Formula (IVb-10) | Formula (IVb) | (RA-4b) |
| Formula (IVb-11) | Formula (IVb) | (RA-4c) |
| Formula (IVb-12) | Formula (IVb) | (RA-4d) |
| Formula (IVb-13) | Formula (IVb) | (RA-4e) |
| Formula (IVb-14) | Formula (IVb) | (RA-4f) |
| Formula (IVb-15) | Formula (IVb) | (RA-5) |
| Formula (IVb-16) | Formula (IVb) | (RA-6) |
| Formula (IVb-17) | Formula (IVb) | (RA-7) |
| Formula (IVb-18) | Formula (IVb) | (RA-8) |
| Formula (IVb-19) | Formula (IVb) | (RA-9) |
| Formula (IVb-20) | Formula (IVb) | (RA-10) |
| Formula (IVb-21) | Formula (IVb) | (RA-11) |
| Formula (IVb-22) | Formula (IVb) | (RA-12) |
| Formula (IVb-23) | Formula (IVb) | (RB) |
| Formula (IVc-1) | Formula (IVc) | (RA-1) |
| Formula (IVc-2) | Formula (IVc) | (RA-1a) |
| Formula (IVc-3) | Formula (IVc) | (RA-1b) |
| Formula (IVc-4) | Formula (IVc) | (RA-1c) |

-continued

| | Base structure | Ring formation formula |
|---|---|---|
| Formula (IVc-5) | Formula (IVc) | (RA-3) |
| Formula (IVc-6) | Formula (IVc) | (RA-3a) |
| Formula (IVc-7) | Formula (IVc) | (RA-3b) |
| Formula (IVc-8) | Formula (IVc) | (RA-4) |
| Formula (IVc-9) | Formula (IVc) | (RA-4a) |
| Formula (IVc-10) | Formula (IVc) | (RA-4b) |
| Formula (IVc-11) | Formula (IVc) | (RA-4c) |
| Formula (IVc-12) | Formula (IVc) | (RA-4d) |
| Formula (IVc-13) | Formula (IVc) | (RA-4e) |
| Formula (IVc-14) | Formula (IVc) | (RA-4f) |
| Formula (IVc-15) | Formula (IVc) | (RA-5) |
| Formula (IVc-16) | Formula (IVc) | (RA-6) |
| Formula (IVc-17) | Formula (IVc) | (RA-7) |
| Formula (IVc-18) | Formula (IVc) | (RA-8) |
| Formula (IVc-19) | Formula (IVc) | (RA-9) |
| Formula (IVc-20) | Formula (IVc) | (RA-10) |
| Formula (IVc-21) | Formula (IVc) | (RA-11) |
| Formula (IVc-22) | Formula (IVc) | (RA-12) |
| Formula (IVc-23) | Formula (IVc) | (RB) |
| Formula (IVd-1) | Formula (IVd) | (RA-1) |
| Formula (IVd-2) | Formula (IVd) | (RA-1a) |
| Formula (IVd-3) | Formula (IVd) | (RA-1b) |
| Formula (IVd-4) | Formula (IVd) | (RA-1c) |
| Formula (IVd-5) | Formula (IVd) | (RA-3) |
| Formula (IVd-6) | Formula (IVd) | (RA-3a) |
| Formula (IVd-7) | Formula (IVd) | (RA-3b) |
| Formula (IVd-8) | Formula (IVd) | (RA-4) |
| Formula (IVd-9) | Formula (IVd) | (RA-4a) |
| Formula (IVd-10) | Formula (IVd) | (RA-4b) |
| Formula (IVd-11) | Formula (IVd) | (RA-4c) |
| Formula (IVd-12) | Formula (IVd) | (RA-4d) |
| Formula (IVd-13) | Formula (IVd) | (RA-4e) |
| Formula (IVd-14) | Formula (IVd) | (RA-4f) |
| Formula (IVd-15) | Formula (IVd) | (RA-5) |
| Formula (IVd-16) | Formula (IVd) | (RA-6) |
| Formula (IVd-17) | Formula (IVd) | (RA-7) |
| Formula (IVd-18) | Formula (IVd) | (RA-8) |
| Formula (IVd-19) | Formula (IVd) | (RA-9) |
| Formula (IVd-20) | Formula (IVd) | (RA-10) |
| Formula (IVd-21) | Formula (IVd) | (RA-11) |
| Formula (IVd-22) | Formula (IVd) | (RA-12) |
| Formula (IVd-23) | Formula (IVd) | (RB) |
| Formula (IVe-1) | Formula (IVe) | (RA-2) |
| Formula (IVe-2) | Formula (IVe) | (RA-2a) |
| Formula (IVe-3) | Formula (IVe) | (RA-2b) |
| Formula (IVe-4) | Formula (IVe) | (RA-2c) |
| Formula (IVf-1) | Formula (IVf) | (RA-2) |
| Formula (IVf-2) | Formula (IVf) | (RA-2a) |
| Formula (IVf-3) | Formula (IVf) | (RA-2b) |
| Formula (IVf-4) | Formula (IVf) | (RA-2c) |
| Formula (IVg-1) | Formula (IVg) | (RA-1) |
| Formula (IVg-2) | Formula (IVg) | (RA-1a) |
| Formula (IVg-3) | Formula (IVg) | (RA-1b) |
| Formula (IVg-4) | Formula (IVg) | (RA-1c) |
| Formula (IVg-5) | Formula (IVg) | (RA-3) |
| Formula (IVg-6) | Formula (IVg) | (RA-3a) |
| Formula (IVg-7) | Formula (IVg) | (RA-3b) |
| Formula (IVg-8) | Formula (IVg) | (RA-4) |
| Formula (IVg-9) | Formula (IVg) | (RA-4a) |
| Formula (IVg-10) | Formula (IVg) | (RA-4b) |
| Formula (IVg-11) | Formula (IVg) | (RA-4c) |
| Formula (IVg-12) | Formula (IVg) | (RA-4d) |
| Formula (IVg-13) | Formula (IVg) | (RA-4e) |
| Formula (IVg-14) | Formula (IVg) | (RA-4f) |
| Formula (IVg-15) | Formula (IVg) | (RA-5) |
| Formula (IVg-16) | Formula (IVg) | (RA-6) |
| Formula (IVg-17) | Formula (IVg) | (RA-7) |
| Formula (IVg-18) | Formula (IVg) | (RA-8) |
| Formula (IVg-19) | Formula (IVg) | (RA-9) |
| Formula (IVg-20) | Formula (IVg) | (RA-10) |
| Formula (IVg-21) | Formula (IVg) | (RA-11) |
| Formula (IVg-22) | Formula (IVg) | (RA-12) |
| Formula (IVg-23) | Formula (IVg) | (RB) |
| Formula (IVh-1) | Formula (IVh) | (RA-2) |
| Formula (IVh-2) | Formula (IVh) | (RA-2a) |
| Formula (IVh-3) | Formula (IVh) | (RA-2b) |

-continued

| | Base structure | Ring formation formula |
|---|---|---|
| Formula (IVh-4) | Formula (IVh) | (RA-2c) |
| Formula (IVi-1) | Formula (IVi) | (RA-1) |
| Formula (IVi-2) | Formula (IVi) | (RA-1a) |
| Formula (IVi-3) | Formula (IVi) | (RA-1b) |
| Formula (IVi-4) | Formula (IVi) | (RA-1c) |
| Formula (IVi-5) | Formula (IVi) | (RA-3) |
| Formula (IVi-6) | Formula (IVi) | (RA-3a) |
| Formula (IVi-7) | Formula (IVi) | (RA-3b) |
| Formula (IVi-8) | Formula (IVi) | (RA-4) |
| Formula (IVi-9) | Formula (IVi) | (RA-4a) |
| Formula (IVi-10) | Formula (IVi) | (RA-4b) |
| Formula (IVi-11) | Formula (IVi) | (RA-4c) |
| Formula (IVi-12) | Formula (IVi) | (RA-4d) |
| Formula (IVi-13) | Formula (IVi) | (RA-4e) |
| Formula (IVi-14) | Formula (IVi) | (RA-4f) |
| Formula (IVi-15) | Formula (IVi) | (RA-5) |
| Formula (IVi-16) | Formula (IVi) | (RA-6) |
| Formula (IVi-17) | Formula (IVi) | (RA-7) |
| Formula (IVi-18) | Formula (IVi) | (RA-8) |
| Formula (IVi-19) | Formula (IVi) | (RA-9) |
| Formula (IVi-20) | Formula (IVi) | (RA-10) |
| Formula (IVi-21) | Formula (IVi) | (RA-11) |
| Formula (IVi-22) | Formula (IVi) | (RA-12) |
| Formula (IVi-23) | Formula (IVi) | (RB) |
| Formula (IVj-1) | Formula (IVj) | (RA-1) |
| Formula (IVj-2) | Formula (IVj) | (RA-1a) |
| Formula (IVj-3) | Formula (IVj) | (RA-1b) |
| Formula (IVj-4) | Formula (IVj) | (RA-1c) |
| Formula (IVj-5) | Formula (IVj) | (RA-3) |
| Formula (IVj-6) | Formula (IVj) | (RA-3a) |
| Formula (IVj-7) | Formula (IVj) | (RA-3b) |
| Formula (IVj-8) | Formula (IVj) | (RA-4) |
| Formula (IVj-9) | Formula (IVj) | (RA-4a) |
| Formula (IVj-10) | Formula (IVj) | (RA-4b) |
| Formula (IVj-11) | Formula (IVj) | (RA-4c) |
| Formula (IVj-12) | Formula (IVj) | (RA-4d) |
| Formula (IVj-13) | Formula (IVj) | (RA-4e) |
| Formula (IVj-14) | Formula (IVj) | (RA-4f) |
| Formula (IVj-15) | Formula (IVj) | (RA-5) |
| Formula (IVj-16) | Formula (IVj) | (RA-6) |
| Formula (IVj-17) | Formula (IVj) | (RA-7) |
| Formula (IVj-18) | Formula (IVj) | (RA-8) |
| Formula (IVj-19) | Formula (IVj) | (RA-9) |
| Formula (IVj-20) | Formula (IVj) | (RA-10) |
| Formula (IVj-21) | Formula (IVj) | (RA-11) |
| Formula (IVj-22) | Formula (IVj) | (RA-12) |
| Formula (IVj-23) | Formula (IVj) | (RB) |
| Formula (IVo-1) | Formula (IVo) | (RA-1) |
| Formula (IVo-2) | Formula (IVo) | (RA-1a) |
| Formula (IVo-3) | Formula (IVo) | (RA-1b) |
| Formula (IVo-4) | Formula (IVo) | (RA-1c) |
| Formula (IVo-5) | Formula (IVo) | (RA-3) |
| Formula (IVo-6) | Formula (IVo) | (RA-3a) |
| Formula (IVo-7) | Formula (IVo) | (RA-3b) |
| Formula (IVo-8) | Formula (IVo) | (RA-4) |
| Formula (IVo-9) | Formula (IVo) | (RA-4a) |
| Formula (IVo-10) | Formula (IVo) | (RA-4b) |
| Formula (IVo-11) | Formula (IVo) | (RA-4c) |
| Formula (IVo-12) | Formula (IVo) | (RA-4d) |
| Formula (IVo-13) | Formula (IVo) | (RA-4e) |
| Formula (IVo-14) | Formula (IVo) | (RA-4f) |
| Formula (IVo-15) | Formula (IVo) | (RA-5) |
| Formula (IVo-16) | Formula (IVo) | (RA-6) |
| Formula (IVo-17) | Formula (IVo) | (RA-7) |
| Formula (IVo-18) | Formula (IVo) | (RA-8) |
| Formula (IVo-19) | Formula (IVo) | (RA-9) |
| Formula (IVo-20) | Formula (IVo) | (RA-10) |
| Formula (IVo-21) | Formula (IVo) | (RA-11) |
| Formula (IVo-22) | Formula (IVo) | (RA-12) |
| Formula (IVo-23) | Formula (IVo) | (RB) |

It may preferably be the case that the compounds have at least two fused rings, wherein at least one fused ring is formed by structures of the formulae (RA-1) to (RA-12) and/or (RA-1a) to (RA-4f) and a further ring is formed by structures of the formulae (RA-1) to (RA-12), (RA-1a) to (RA-4f) or (RB), where the compounds include at least one structure of the formulae (Va) to (Vs), preferably where the compounds are selected from the compounds of the formulae (Va) to (Vz):

Formula (Va)

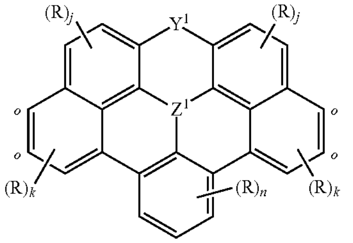

Formula (Vb)

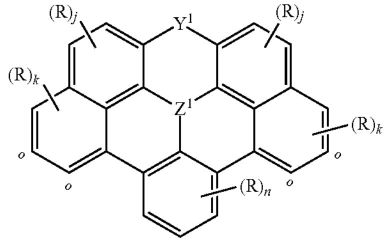

Formula (Vc)

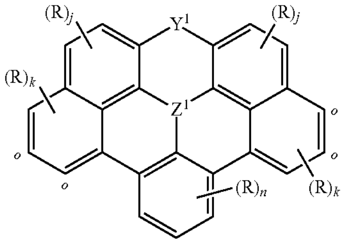

Formula (Vd)

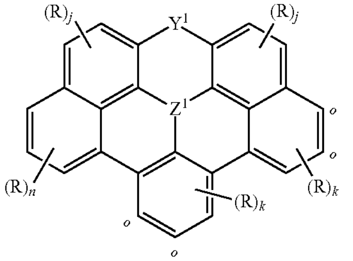

Formula (Ve)

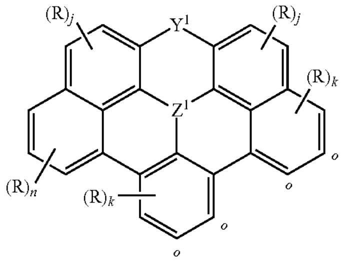

-continued
Formula (Vf)
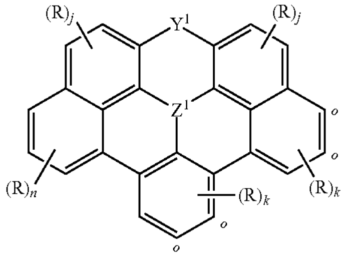
Formula (Vg)
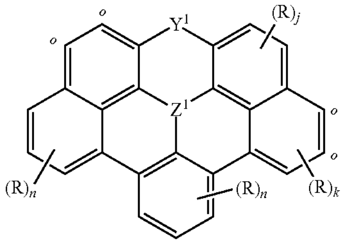
Formula (Vh)
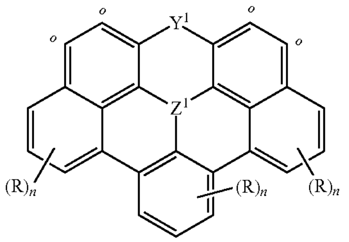
Formula (Vi)
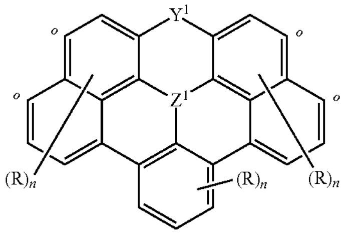
Formula (Vj)
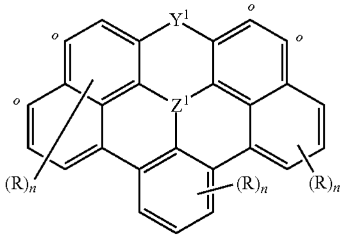
-continued
Formula (Vk)
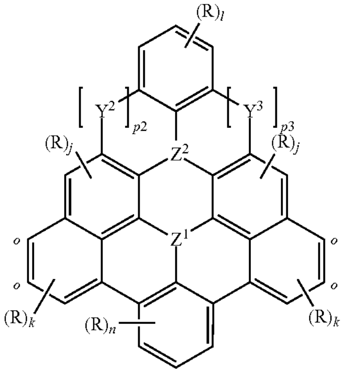
Formula (Vl)
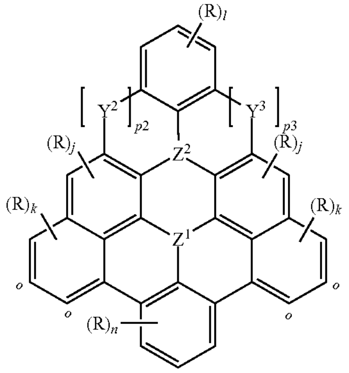
Formula (Vm)
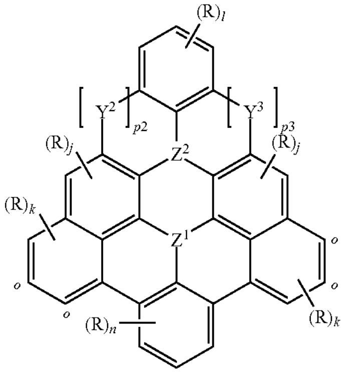
Formula (Vn)
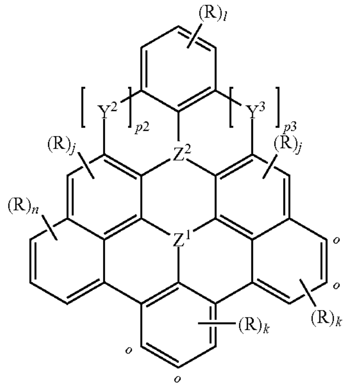

-continued

Formula (Vo)

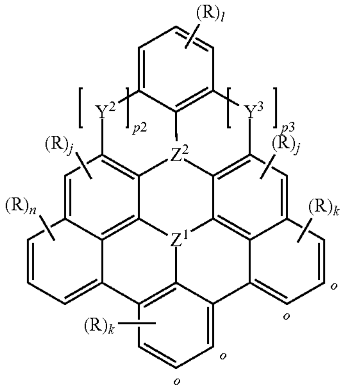

Formula (Vp)

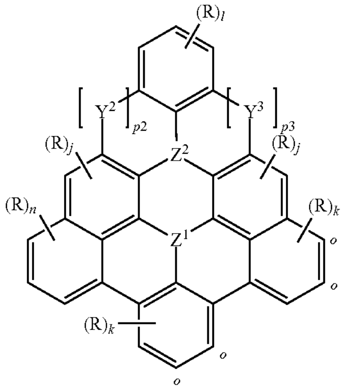

Formula (Vq)

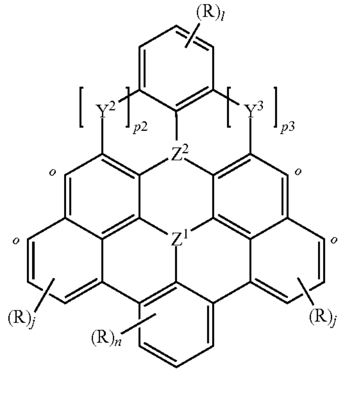

Formula (Vr)

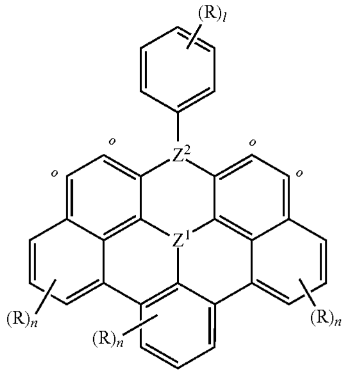

-continued

Formula (Vs)

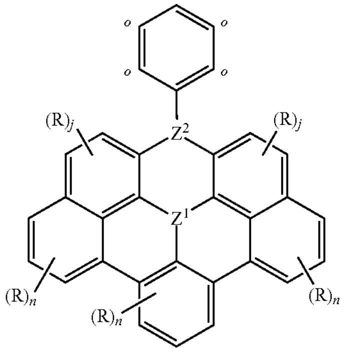

where $Y^1$, $Y^2$, $Y^3$, X, $Z^1$, $Z^2$ and R have the definitions given above, especially for formula (Ia) and/or (Ib), the symbol o represents the sites of attachment of at least one structure of the formulae (RA-1) to (RA-12) and/or (RA-1a) to (RA-4f) or a structure of the formula (RB), the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, the index j is 0, 1 or 2, preferably 0 or 1, and the index k is 0 or 1, preferably 0, where the sum total of the indices k, j, l, m and n is preferably 0, 1, 2, 3 or 4, more preferably 2, 3 or 4. Preference is given here to structures/compounds of the formulae (Va) to (Vq). Preferably, the sum total of the indices k, j, l, m and n is 0, 1, 2 or 3, preferably 1 or 2.

It may be the case here that the formulae (Va) to (Vs) have at least two fused rings, where the fused rings are the same and the moiety formed by two R radicals can be represented by at least one structure of the formulae (RA-1) to (RA-12) and/or (RA-1a) to (RA-4f).

It may further be the case that the formulae (Va) to (Vs) have at least two fused rings, where the fused rings are different and the moiety formed by two R radicals can be represented in each case by at least one structure of the formulae (RA-1) to (RA-12) and/or (RA-1a) to (RA-4f).

It may additionally be the case that the formulae (Va) to (Vs) have at least two fused rings, where the fused rings are different and one of the two fused rings has a moiety formed by two R radicals that can be represented by at least one of the structures of the formulae (RA-1) to (RA-12) and/or (RA-1a) to (RA-4f), and one of the two fused rings has a moiety formed by two R radicals that can be represented by one of the structures of the formula (RB).

It may also be the case that the substituents R and $R^a$, $R^1$ and $R^2$ of the above formulae do not form a fused aromatic or heteroaromatic ring system with the ring atoms of the ring system to which R and $R^a$, $R^1$ and $R^2$ bind. This includes the formation of a fused aromatic or heteroaromatic ring system with possible substituents $R^1$ and $R^2$ which may be bonded to the R, $R^a$ and $R^1$ radicals.

When two radicals that may especially be selected from R, $R^a$, $R^1$ and/or $R^2$ form a ring system with one another, this ring system may be mono- or polycyclic, aliphatic, heteroaliphatic, aromatic or heteroaromatic. In this case, the radicals which together form a ring system may be adjacent, meaning that these radicals are bonded to the same carbon atom or to carbon atoms directly bonded to one another, or they may be further removed from one another. In addition, the ring systems provided with the substituents R, $R^a$, $R^1$ and/or $R^2$ may also be joined to one another via a bond, such that this can bring about a ring closure. In this case, each of the corresponding bonding sites has preferably been provided with a substituent R, $R^a$, $R^1$ and/or $R^2$.

In a preferred configuration, a compound of the invention can be represented by at least one of the structures of formula (Ia), (Ib), (IIa) to (IId), (IIIa) to (IIId), (IVa) to (IVr) and/or (Va) to (Vs). Preferably, compounds of the invention, preferably comprising structures of formula (Ia), (Ib), (IIa) to (IId), (IIIa) to (IIId), (IVa) to (IVr) and/or (Va) to (Vs), have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

Preferred aromatic or heteroaromatic ring systems R, $R^a$ and/or Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals.

Preferably, at least one substituent R is the same or different at each instance and is selected from the group consisting of H, D or an aromatic or heteroaromatic ring system selected from the groups of the following formulae Ar-1 to Ar-75, where the substituents R preferably either form a ring according to the structures of the formulae (RA-1) to (RA-12), (RA-1a) to (RA-4f) or (RB) or the substituent R is the same or different at each instance and is selected from the group consisting of H, D or an aromatic or heteroaromatic ring system selected from the groups of the following formulae Ar-1 to Ar-75, and/or the Ar group is the same or different at each instance and is selected from the groups of the following formulae Ar-1 to Ar-75:

Ar-1

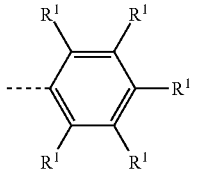

Ar-2

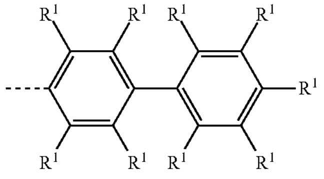

-continued

Ar-3

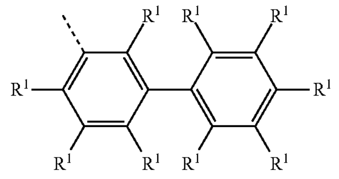

Ar-4

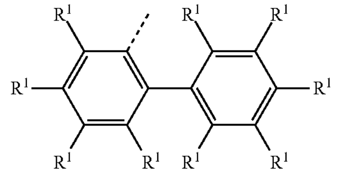

Ar-5

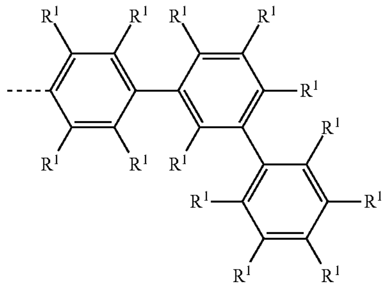

Ar-6

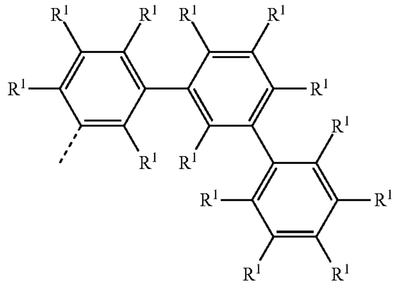

Ar-7

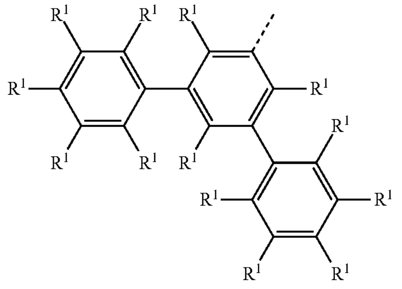

Ar-8

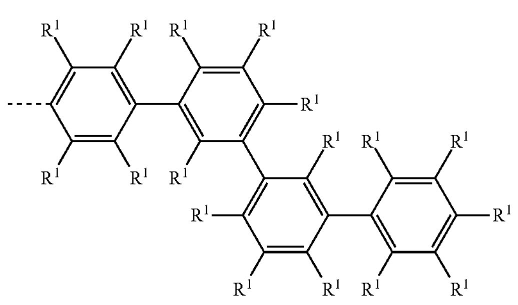

-continued
Ar-9
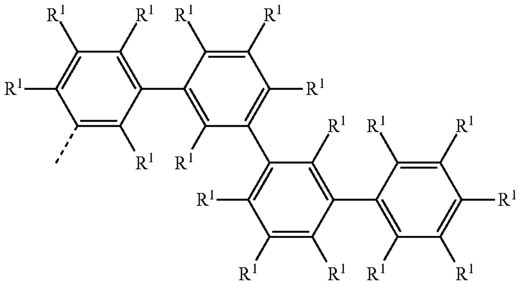
Ar-10
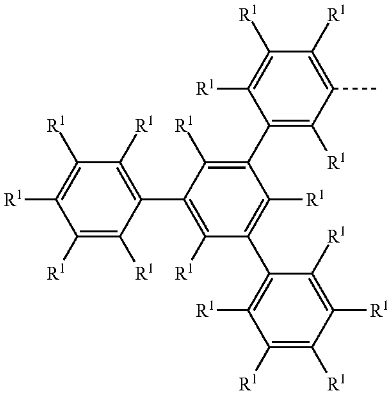
Ar-11
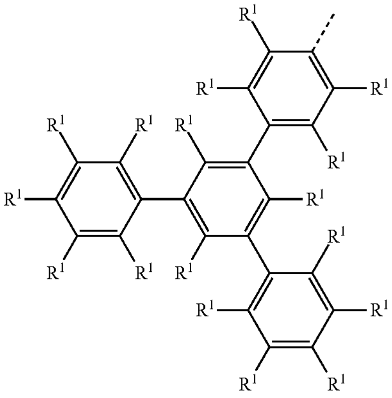
Ar-12
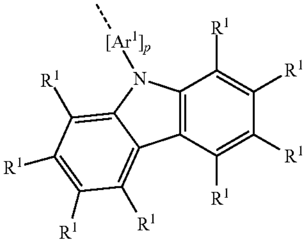
Ar-13
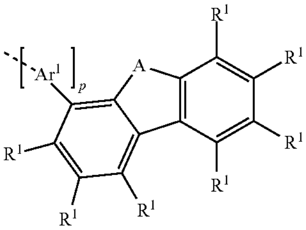
-continued
Ar-14
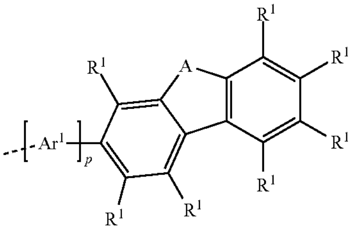
Ar-15
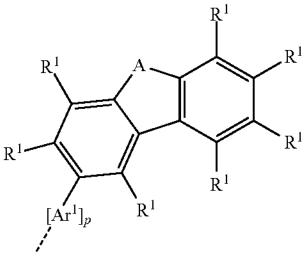
Ar-16
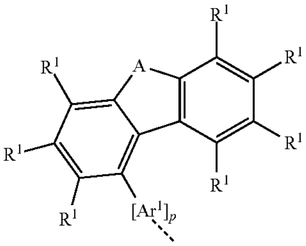
Ar-17
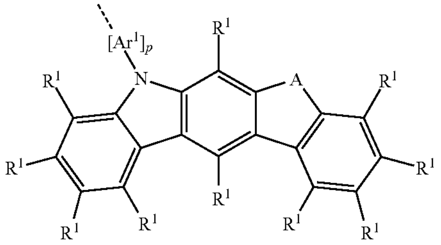
Ar-18
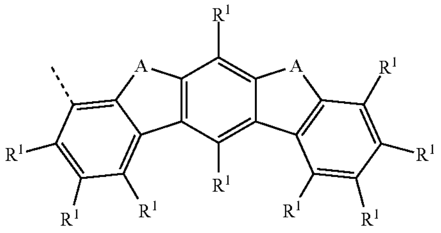
Ar-19
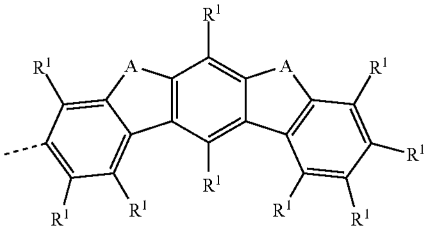

-continued
Ar-20
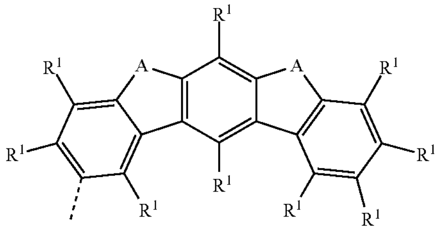
Ar-21
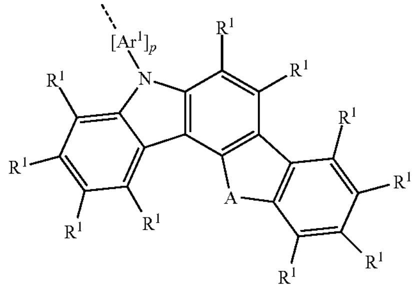
Ar-22
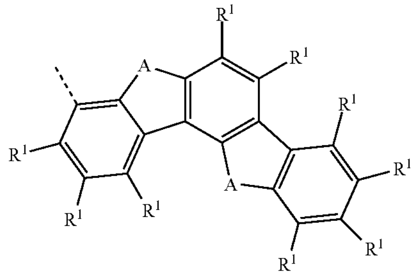
Ar-23
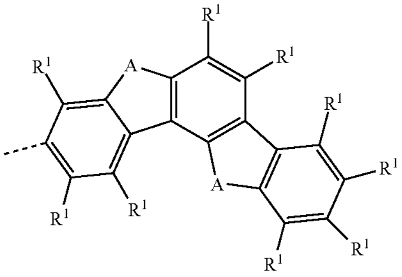
Ar-24
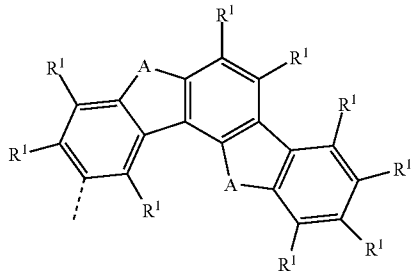
-continued
Ar-25
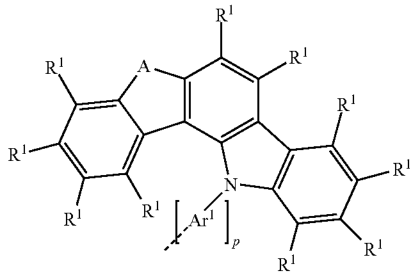
Ar-26
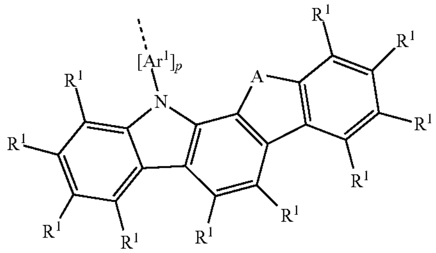
Ar-27
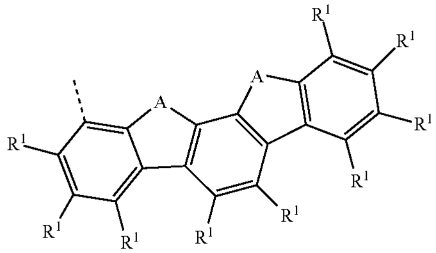
Ar-28
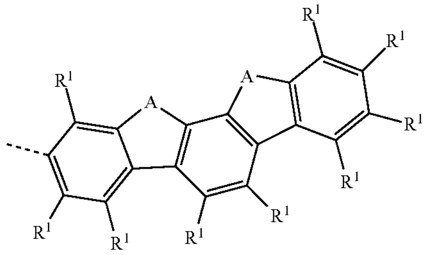
Ar-29
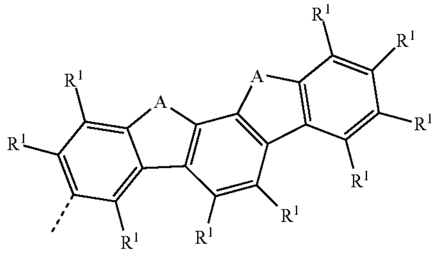
Ar-30
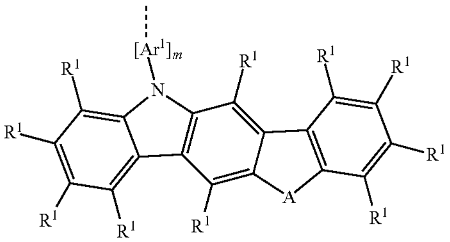

-continued
Ar-31
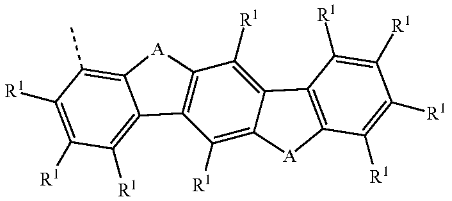
Ar-32
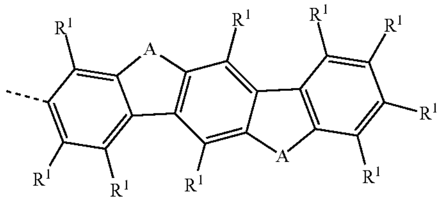
Ar-33
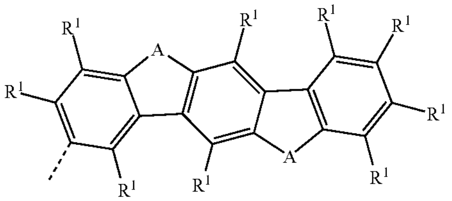
Ar-34
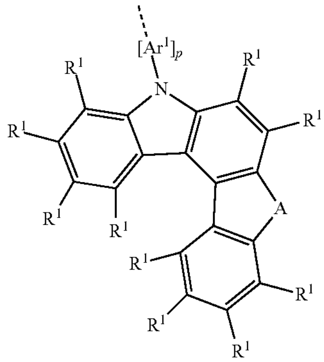
Ar-35
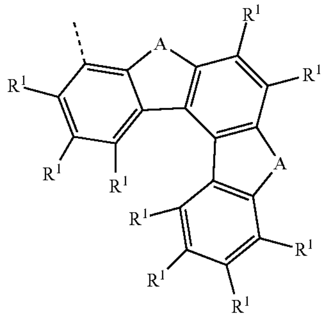
Ar-36
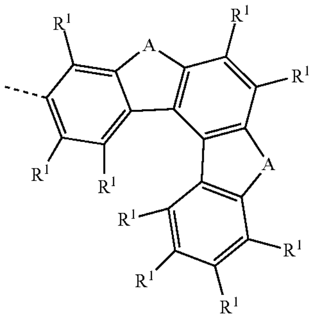
-continued
Ar-37
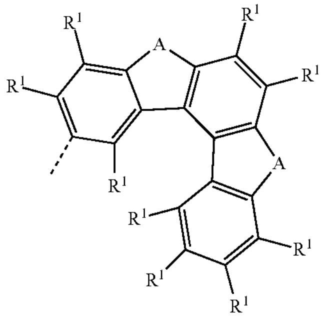
Ar-38
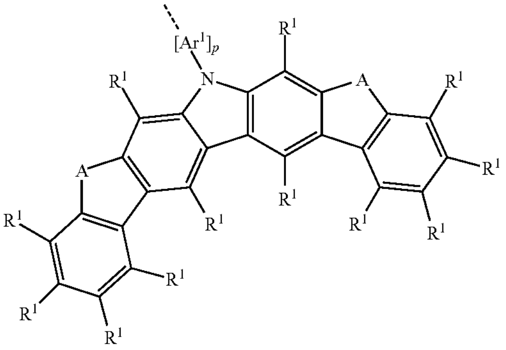
Ar-39
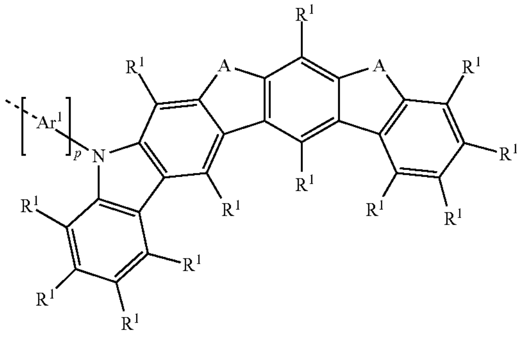
Ar-40
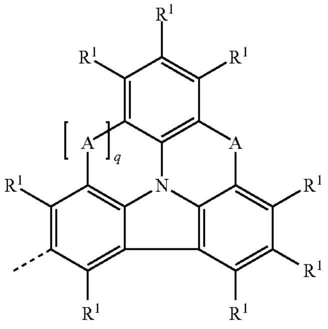

-continued
Ar-41
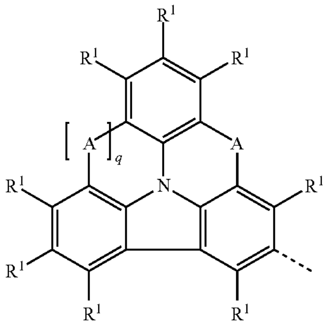
Ar-42
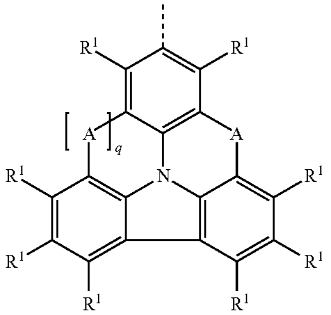
Ar-43
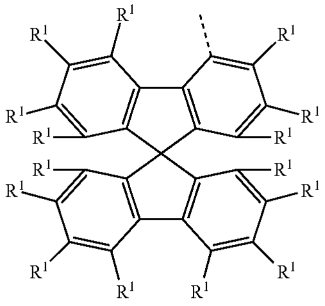
Ar-44
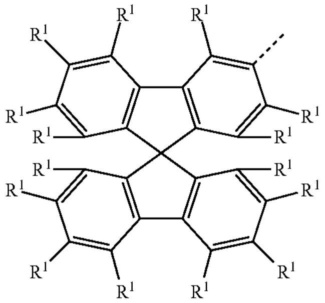
Ar-45
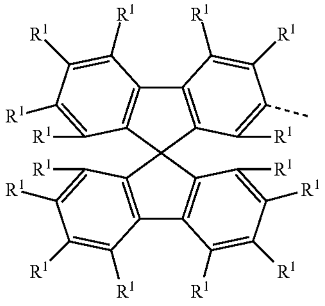
-continued
Ar-46
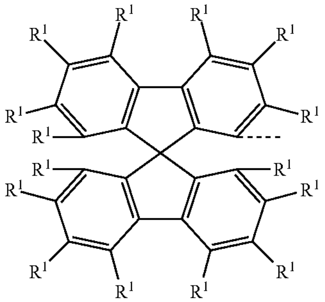
Ar-47
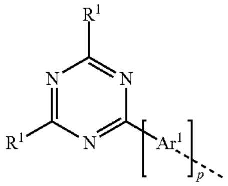
Ar-48
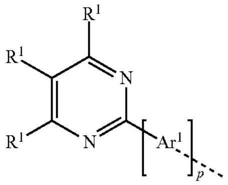
Ar-49
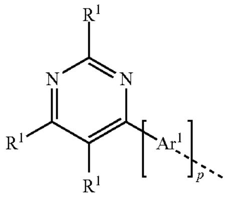
Ar-50
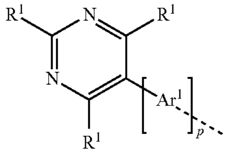
Ar-51
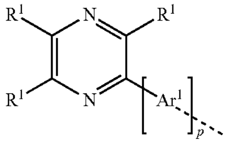
Ar-52
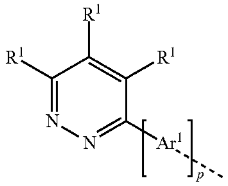
Ar-53
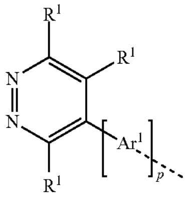

-continued
Ar-54
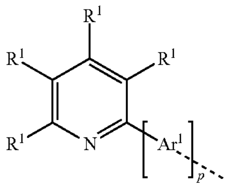
Ar-55
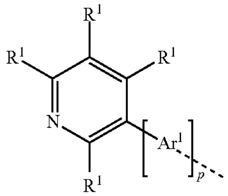
Ar-56
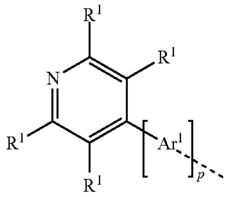
Ar-57
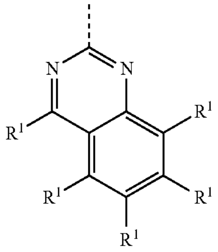
Ar-58
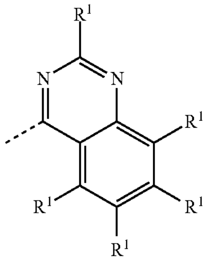
Ar-59
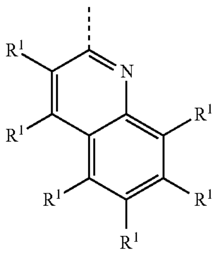
-continued
Ar-60
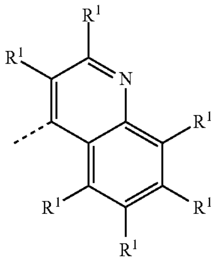
Ar-61
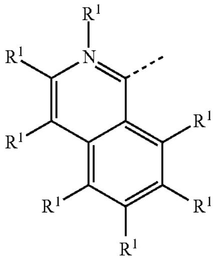
Ar-62
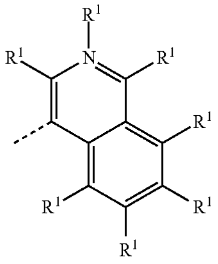
Ar-63
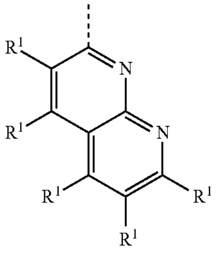
Ar-64
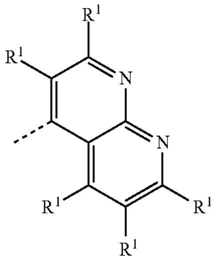
Ar-65
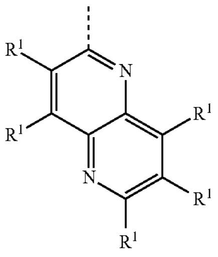

-continued

Ar-66

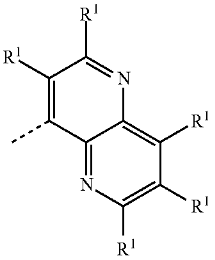

Ar-67

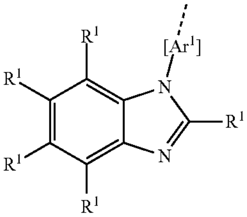

Ar-68

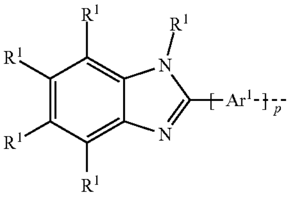

Ar-69

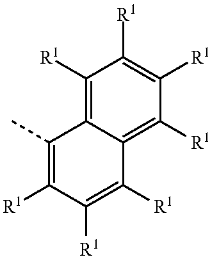

Ar-70

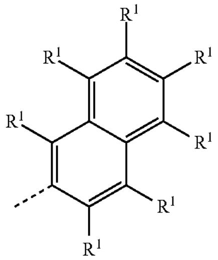

Ar-71

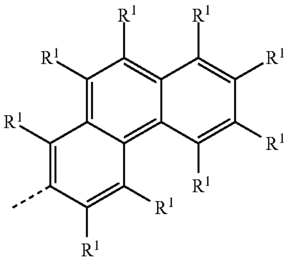

-continued

Ar-72

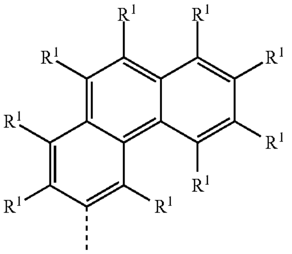

Ar-73

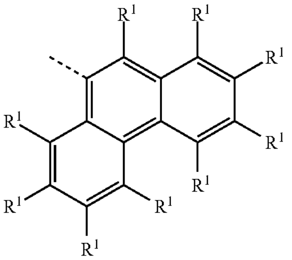

Ar-74

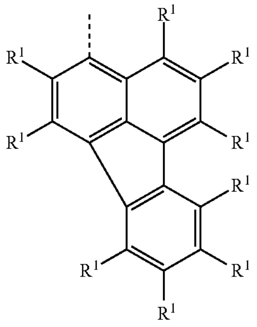

Ar-75

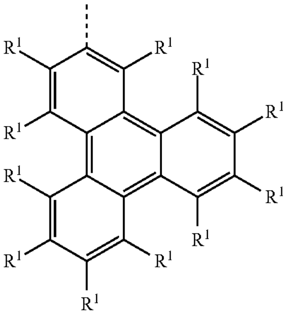

where $R^1$ is as defined above, the dotted bond represents the attachment site and, in addition:

Ar' is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to HetAr;

q is 0 or 1, where q=0 means that no A group is bonded at this position and $R^1$ radicals are bonded to the corresponding carbon atoms instead.

When the abovementioned groups for Ar have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Preference is given to phenyl, biphenyl, terphenyl and quaterphenyl having bonding patterns as listed above for Ar-1 to Ar-11, where these structures, rather than by $R^1$, may be substituted by one or more $R^2$ radicals, but are preferably unsubstituted. Preference is further given to triazine, pyrimidine and quinazoline as listed above for Ar-47 to Ar-50, Ar-57 and Ar-58, where these structures, rather than by $R^1$, may be substituted by one or more $R^2$ radicals.

There follows a description of preferred substituents R and $R^a$.

In a preferred embodiment of the invention, R is the same or different at each instance and is selected from the group consisting of H, D, F, CN, $NO_2$, $Si(R^1)_3$, $B(OR^1)_2$, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

In a further-preferred embodiment of the invention, R is the same or different at each instance and is selected from the group consisting of H, D, F, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

It may further be the case that at least one substituent R is the same or different at each instance and is selected from the group consisting of H, D, an aromatic or heteroaromatic ring system which has 6 to 30 aromatic ring atoms and may be substituted by one or more $R^1$ radicals, and an $N(Ar)_2$ group. In a further-preferred embodiment of the invention, the R substituents either form a ring according to the structures of the formulae (RA-1) to (RA-12), (RA-1a) to (RA-4f) or (RB) or R is the same or different at each instance and is selected from the group consisting of H, D, an aromatic or heteroaromatic ring system which has 6 to 30 aromatic ring atoms and may be substituted by one or more $R^1$ radicals, and an $N(Ar)_2$ group. More preferably, R is the same or different at each instance and is selected from the group consisting of H or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^1$ radicals.

In a preferred embodiment of the invention, $R^a$ is the same or different at each instance and is selected from the group consisting of a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

In a further-preferred embodiment of the invention, $R^a$ is the same or different at each instance and is selected from the group consisting of a straight-chain alkyl group having 1 to 10 carbon atoms or a branched or cyclic alkyl group having 3 to 10 carbon atoms, where the alkyl group may be substituted in each case by one or more $R^1$ radicals, an aromatic or heteroaromatic ring system which has 6 to 30 aromatic ring atoms and may be substituted by one or more $R^1$ radicals. More preferably, $R^a$ is the same or different at each instance and is selected from the group consisting of a straight-chain alkyl group having 1 to 5 carbon atoms or a branched or cyclic alkyl group having 3 to 5 carbon atoms, where the alkyl group may be substituted in each case by one or more $R^1$ radicals, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^1$ radicals.

In a preferred embodiment of the invention, $R^a$ is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more $R^1$ radicals, or an aromatic or heteroaromatic ring system which has 6 to 24 aromatic ring atoms and may be substituted in each case by one or more $R^1$ radicals; at the same time, two $R^a$ radicals together may also form a ring system. More preferably, $R^a$ is the same or different at each instance and is selected from the group consisting of a straight-chain alkyl group having 1, 2, 3 or 4 carbon atoms or a branched or cyclic alkyl group having 3 to 6 carbon atoms, where the alkyl group may be substituted in each case by one or more $R^1$ radicals, but is preferably unsubstituted, or an aromatic ring system which has 6 to 12 aromatic ring atoms, especially 6 aromatic ring atoms, and may be substituted in each case by one or more preferably nonaromatic $R^1$ radicals, but is preferably unsubstituted; at the same time, two $R^a$ radicals together may form a ring system. Most preferably, $R^a$ is the same or different at each instance and is selected from the group consisting of a straight-chain alkyl group having 1, 2, 3 or 4 carbon atoms, or a branched alkyl group having 3 to 6 carbon atoms. Most preferably, $R^a$ is a methyl group or is a phenyl group, where two phenyl groups together may form a ring system, preference being given to a methyl group over a phenyl group.

Preferred aromatic or heteroaromatic ring systems R, $R^a$ or Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals. The structures Ar-1 to Ar-75 listed above are particularly preferred, preference being given to structures of the formulae (Ar-1), (Ar-2), (Ar-3), (Ar-12), (Ar-13), (Ar-14), (Ar-15), (Ar-16), (Ar-69), (Ar-70), (Ar-75), and particular preference to structures of the formulae (Ar-1), (Ar-2), (Ar-3), (Ar-12), (Ar-13), (Ar-14), (Ar-15), (Ar-16).

Further suitable R groups are groups of the formula $—Ar^4—N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from a single bond, $C(R^1)_2$, $NR^1$, O and S. Preferably, the linkage of $Ar^4$ and $Ar^2$ to one another or of $Ar^2$ and $Ar^3$ to one another is ortho in each case to the position of linkage to the nitrogen atom, such that, for example and with preference, a carbazole is formed. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene or triphenylene, each of which may be substituted by one or more $R^1$ radicals. Most preferably, $Ar^2$ and $Ar^3$ are the same or different at each instance and are selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

In a further preferred embodiment of the invention, $R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^5$ radicals, but is preferably unsubstituted, or an aromatic or heteroaromatic ring system which has 6 to 13 aromatic ring atoms and may be substituted in each case by one or more $R^5$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

At the same time, in compounds of the invention that are processed by vacuum evaporation, the alkyl groups preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

It may further be the case that the compound includes exactly two or exactly three structures of formula (Ia), (Ib), (IIa) to (IId), (IIIa) to (IIId), (IVa) to (IVr) and/or (Va) to (Vs), where preferably one of the $Y^1$, $Y^2$, $Y^3$ groups or one of the aromatic or heteroaromatic ring systems to which at least one of the $Y^1$, $Y^2$, $Y^3$ groups binds is shared by both structures.

In a preferred configuration, the compounds include at least one of the structures of the formulae (D-1) to (D-5), where the compounds more preferably conform to the formulae (D-1) to (D-5), Formula (D-1)

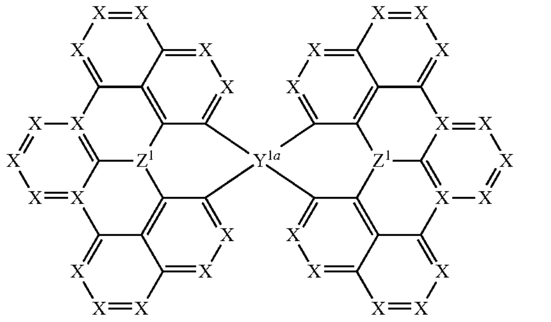

Formula (D-2)

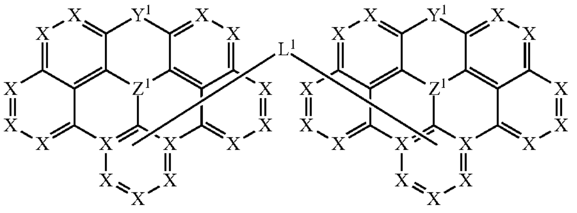

-continued

Formula (D3)

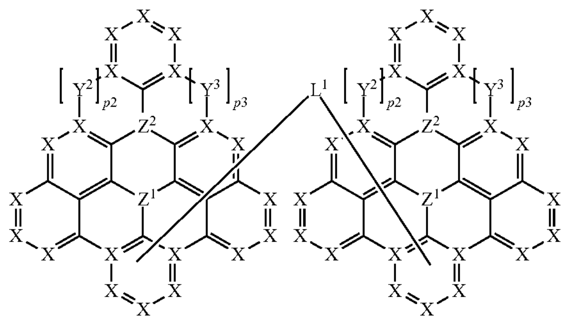

Formula (D3)

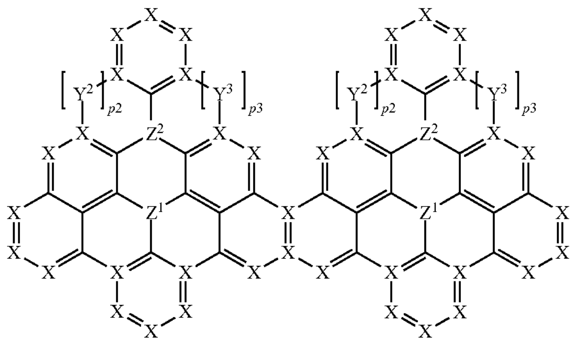

Formula (D5)

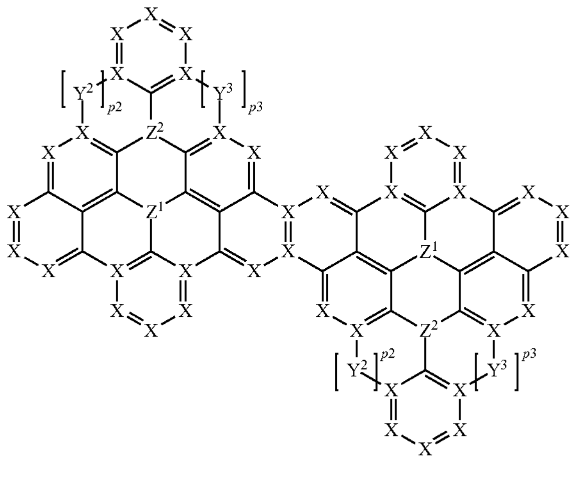

where Yea is C or Si, the $L^1$ group represents a connecting group, preferably a bond or an aromatic or heteroaromatic ring system which has 5 to 40, preferably 5 to 30, aromatic ring atoms and may be substituted by one or more $R^1$ radicals, and the further symbols and indices used have the definitions given above, especially for formula (Ia) and/or (Ib).

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (Ia) and/or (Ib). More preferably, $L^1$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (Ia) and/or (Ib).

Further preferably, the symbol $L^1$ shown in formulae including (D2) and (D3) is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the $L^1$ group shown in formulae (D2) and (D3) comprises an aromatic ring system having not more than two fused aromatic and/or heteroaromatic 6-membered rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^1$ radicals, but are preferably unsubstituted.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds shown in the following table:

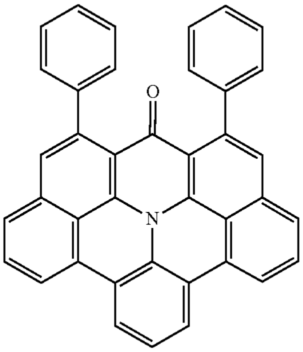 [SMILES: O=c1c2c(-c3ccccc3)cc3cccc4c5cccc6c7cccc8cc(-c9ccccc9)c1c(c87)n(c56)c2c34]
1
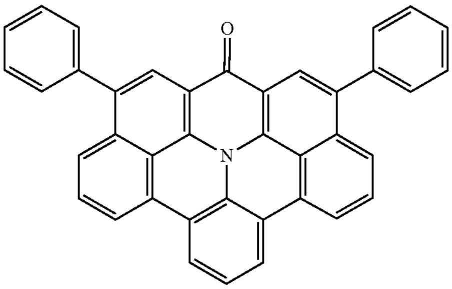 [SMILES: O=c1c2cc(-c3ccccc3)c3cccc4c5cccc6c7cccc8c(-c9ccccc9)cc1c(c87)n(c56)c2c34]
2
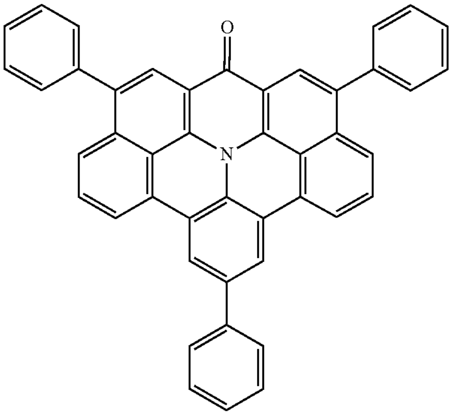 [SMILES: O=c1c2cc(-c3ccccc3)c3cccc4c5cc(-c6ccccc6)cc6c7cccc8c(-c9ccccc9)cc1c(c87)n(c56)c2c34]
3
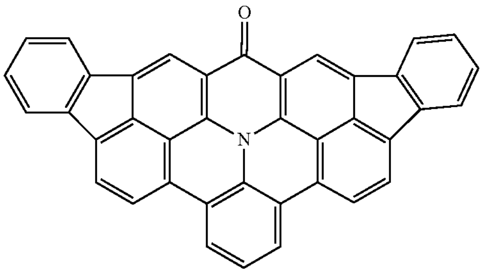 [SMILES: O=c1c2cc3c4ccccc4c4ccc5c6cccc7c8ccc9c%10ccccc%10c%10cc1c(c8c9%10)n(c67)c2c5c43]
4

-continued
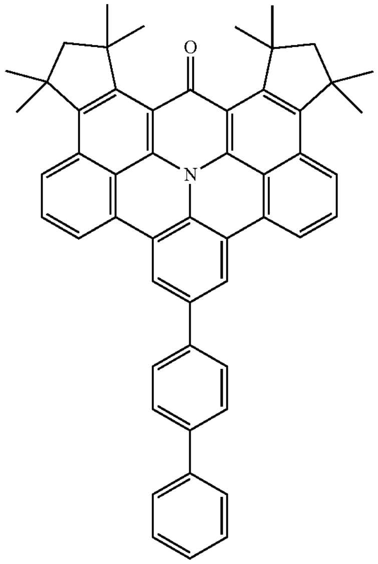
5
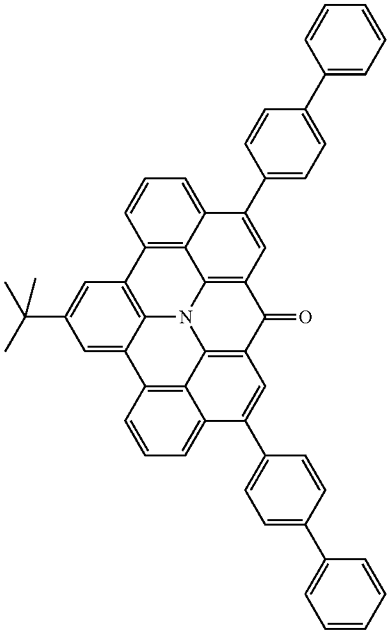 [SMILES: CC(C)(C)c1cc2c3cccc4c(-c5ccc(-c6ccccc6)cc5)cc5c(=O)c6cc(-c7ccc(-c8ccccc8)cc7)c7cccc8c(c1)c2n(c5c43)c6c78]
6
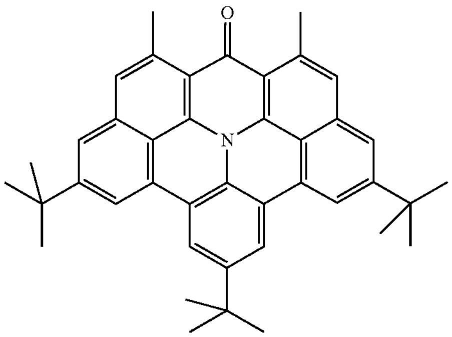 [SMILES: Cc1cc2cc(C(C)(C)C)cc3c4cc(C(C)(C)C)cc5c6cc(C(C)(C)C)cc7cc(C)c8c(=O)c1c(c23)n(c45)c8c76]
7

-continued
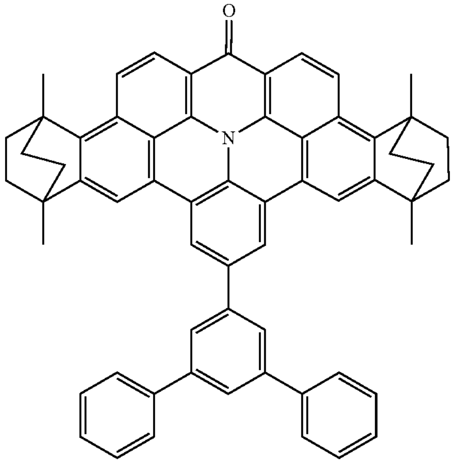 [SMILES: CC12CCC(C)(CC1)c1c2cc2c3cc(-c4cc(-c5ccccc5)cc(-c5ccccc5)c4)cc4c5cc6c(c7ccc8c(=O)c9ccc1c2c9n(c34)c8c75)C1(C)CCC6(C)CC1]
8
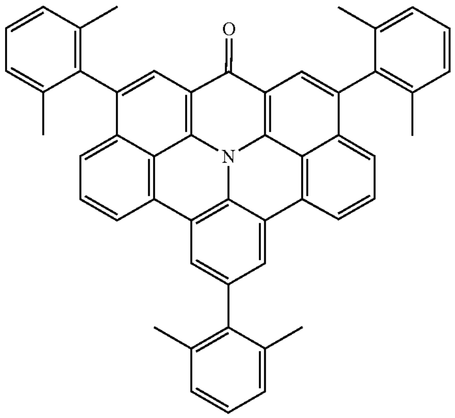 [SMILES: Cc1cccc(C)c1-c1cc2c3cccc4c(-c5c(C)cccc5C)cc5c(=O)c6cc(-c7c(C)cccc7C)c7cccc8c(c1)c2n(c5c43)c6c78]
9
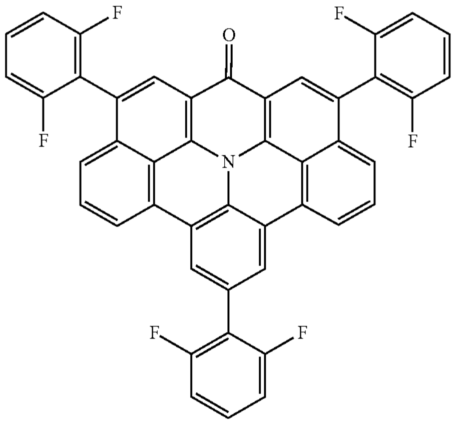 [SMILES: O=c1c2cc(-c3c(F)cccc3F)c3cccc4c5cc(-c6c(F)cccc6F)cc6c7cccc8c(-c9c(F)cccc9F)cc1c(c87)n(c56)c2c34]
10

-continued
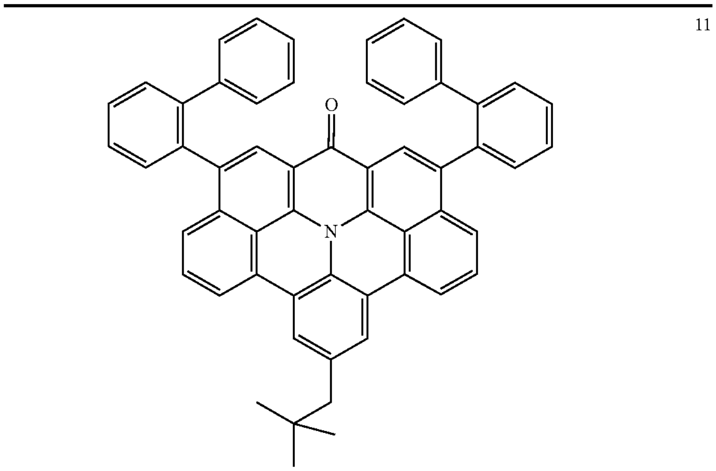
11
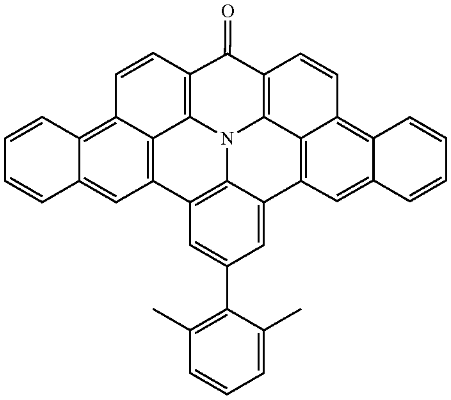 [SMILES: Cc1cccc(C)c1-c1cc2c3cc4ccccc4c4ccc5c(=O)c6ccc7c8ccccc8cc8c(c1)c2n(c5c43)c6c78]
12
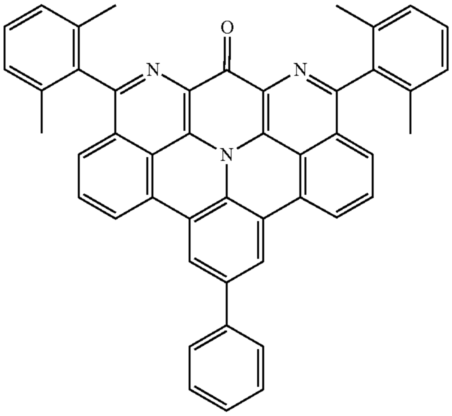 [SMILES: Cc1cccc(C)c1-c1nc2c(=O)c3nc(-c4c(C)cccc4C)c4cccc5c6cc(-c7ccccc7)cc7c8cccc1c8c2n(c76)c3c45]
13

-continued
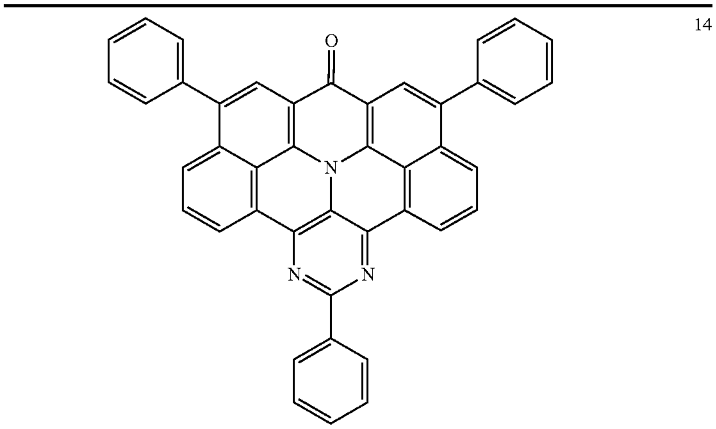
14
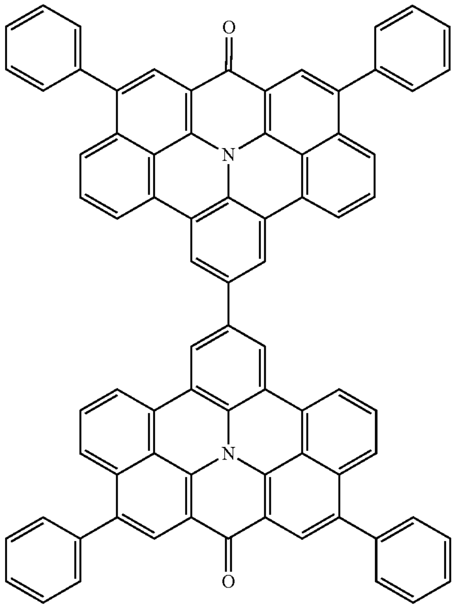 [SMILES: O=c1c2cc(-c3ccccc3)c3cccc4c5cc(-c6cc7c8cccc9c(-c%10ccccc%10)cc%10c(=O)c%11cc(-c%12ccccc%12)c%12cccc%13c(c6)c7n(c%10c98)c%11c%12%13)cc6c7cccc8c(-c9ccccc9)cc1c(c87)n(c56)c2c34]
15
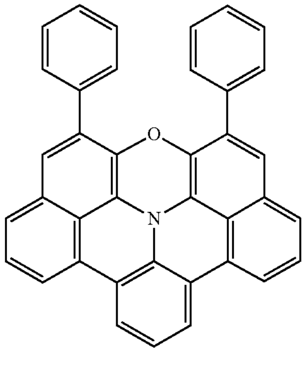 [SMILES: c1ccc(-c2cc3cccc4c5cccc6c7cccc8cc(-c9ccccc9)c9oc2c(c34)n(c56)c9c87)cc1]
16

-continued
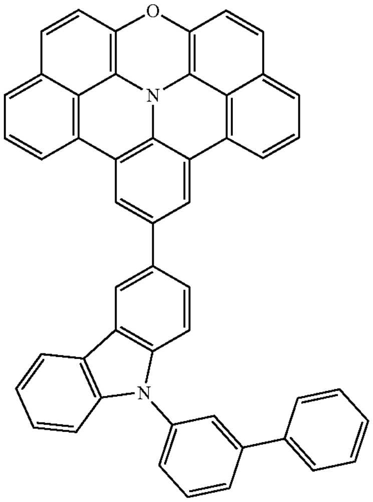 [SMILES: c1ccc(-c2cccc(-n3c4ccccc4c4cc(-c5cc6c7cccc8ccc9oc%10ccc%11cccc%12c(c5)c6n(c9c87)c%10c%11%12)ccc43)c2)cc1]
17
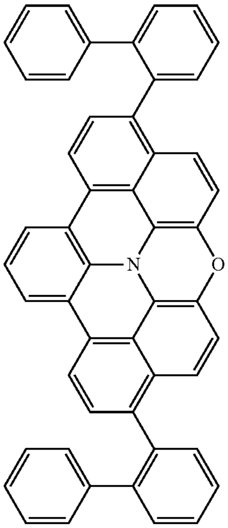 [SMILES: c1ccc(-c2ccccc2-c2ccc3c4cccc5c6ccc(-c7ccccc7-c7ccccc7)c7ccc8oc9ccc2c3c9n(c45)c8c76)cc1]
18
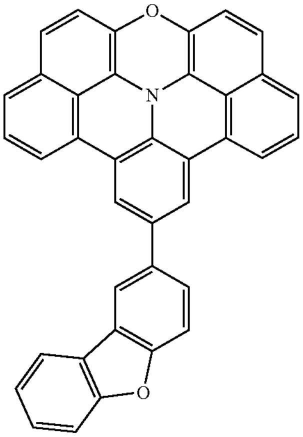 [SMILES: c1ccc2c(c1)oc1ccc(-c3cc4c5cccc6ccc7oc8ccc9cccc%10c(c3)c4n(c7c65)c8c9%10)cc12]
19

-continued
20
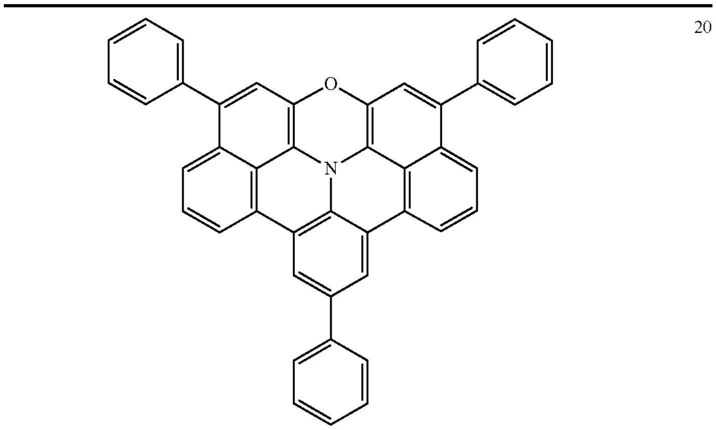
21
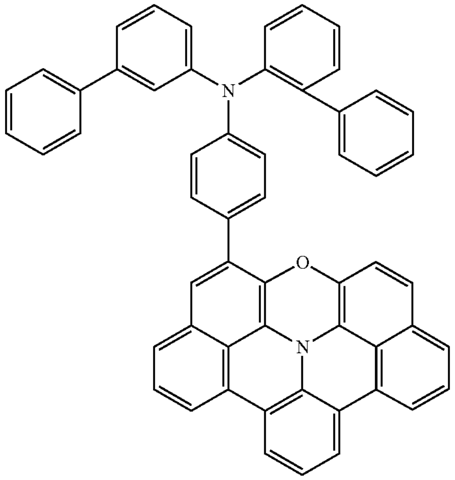 [SMILES: c1ccc(-c2cccc(N(c3ccc(-c4cc5cccc6c7cccc8c9cccc%10ccc%11oc4c(c56)n(c87)c%11c%109)cc3)c3ccccc3-c3ccccc3)c2)cc1]
22
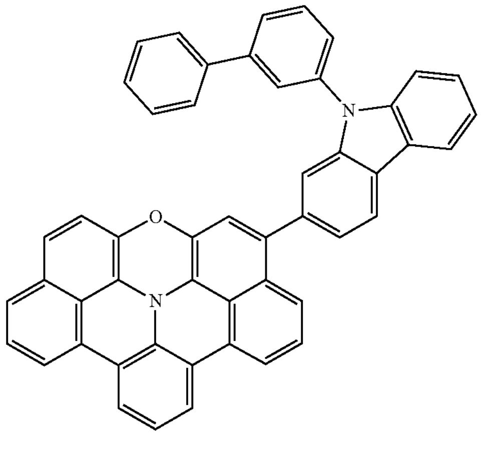 [SMILES: c1ccc(-c2cccc(-n3c4ccccc4c4ccc(-c5cc6oc7ccc8cccc9c%10cccc%11c%12cccc5c%12c6n(c%10%11)c7c89)cc43)c2)cc1]

-continued
23
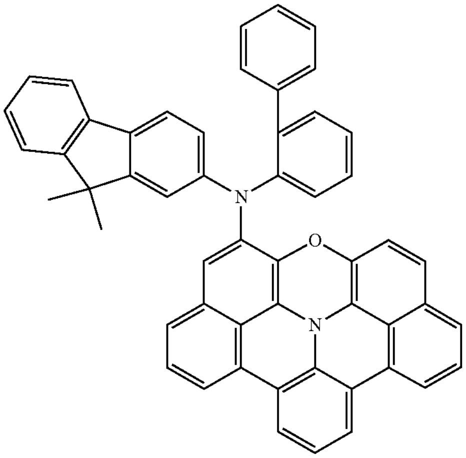 [SMILES: CC1(C)c2ccccc2-c2ccc(N(c3ccccc3-c3ccccc3)c3cc4cccc5c6cccc7c8cccc9ccc%10oc3c(c45)n(c76)c%10c98)cc21]
24
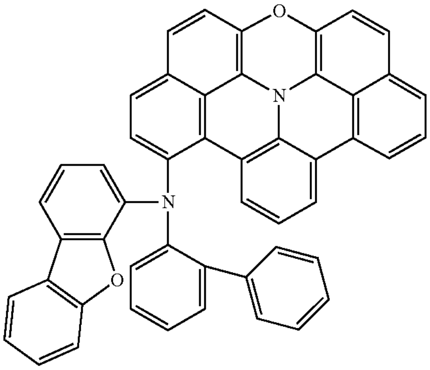 [SMILES: c1ccc(-c2ccccc2N(c2cccc3c2oc2ccccc23)c2ccc3ccc4oc5ccc6cccc7c8cccc9c2c3c4n(c89)c5c67)cc1]
25
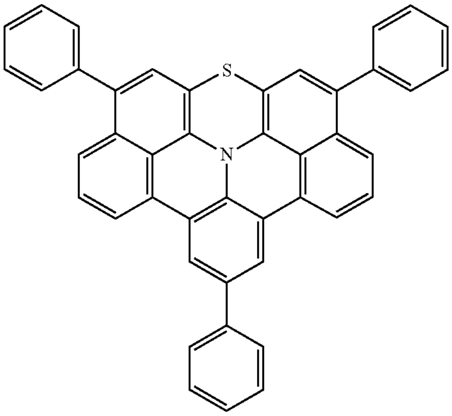 [SMILES: c1ccc(-c2cc3c4cccc5c(-c6ccccc6)cc6sc7cc(-c8ccccc8)c8cccc9c(c2)c3n(c6c54)c7c89)cc1]

-continued
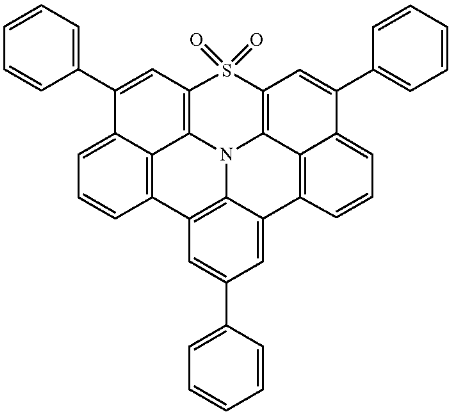 [SMILES: O=S1(=O)c2cc(-c3ccccc3)c3cccc4c3c2N2c3c-4cc(-c4ccccc4)cc3-c3cccc4c(-c5ccccc5)cc1c2c34]
26
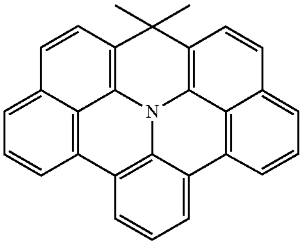 [SMILES: CC1(C)c2ccc3cccc4c3c2N2c3c-4cccc3-c3cccc4ccc1c2c34]
27
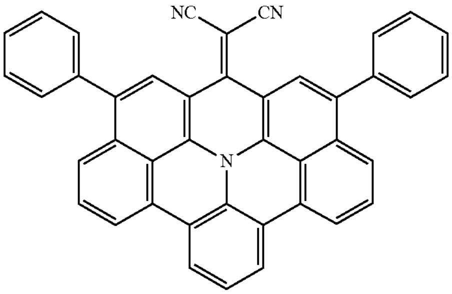 [SMILES: N#CC(C#N)=c1c2cc(-c3ccccc3)c3cccc4c5cccc6c5N(c2c34)c2c1cc(-c1ccccc1)c1cccc6c21]
28
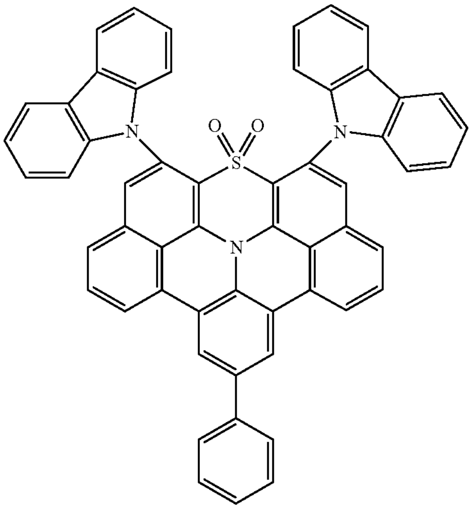 [SMILES: O=S1(=O)c2c(-n3c4ccccc4c4ccccc43)cc3cccc4c3c2N2c3c-4cc(-c4ccccc4)cc3-c3cccc4cc(-n5c6ccccc6c6ccccc65)c1c2c34]
29

-continued
30
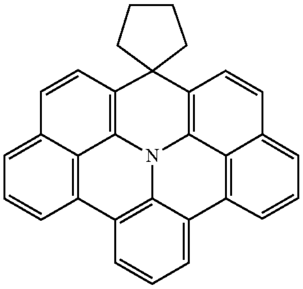 [SMILES: c1cc2c3c(c1)-c1cccc4ccc5c(c14)N3c1c(ccc3cccc-2c13)C51CCCC1]
31
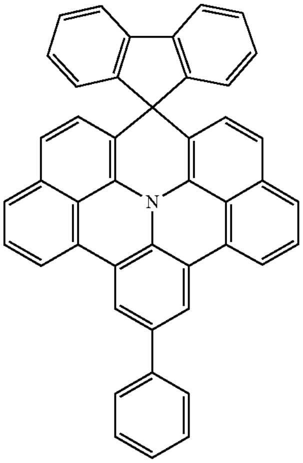 [SMILES: c1ccc(-c2cc3c4c(c2)-c2cccc5ccc6c(c25)N4c2c(ccc4cccc-3c24)C62c3ccccc3-c3ccccc32)cc1]
32
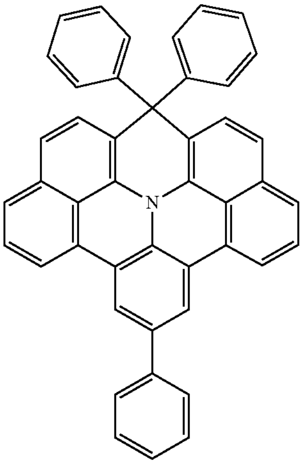 [SMILES: c1ccc(-c2cc3c4c(c2)-c2cccc5ccc6c(c25)N4c2c(ccc4cccc-3c24)C6(c2ccccc2)c2ccccc2)cc1]

-continued
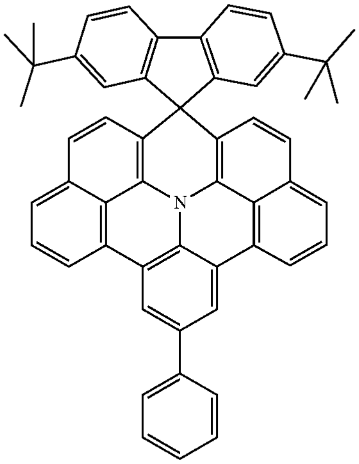 [SMILES: CC(C)(C)c1ccc2c(c1)C1(c3cc(C(C)(C)C)ccc3-2)c2ccc3cccc4c3c2N2c3c-4cc(-c4ccccc4)cc3-c3cccc4ccc1c2c34]
33
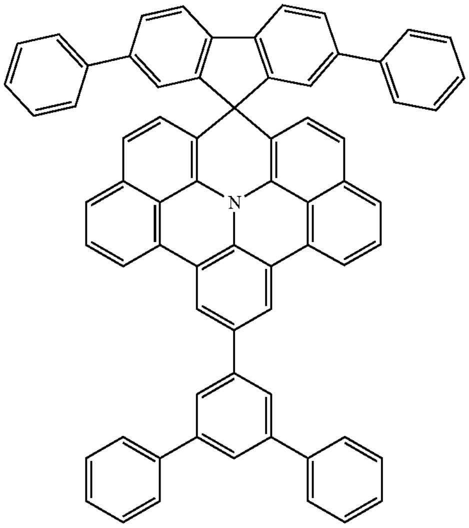 [SMILES: c1ccc(-c2cc(-c3ccccc3)cc(-c3cc4c5c(c3)-c3cccc6ccc7c(c36)N5c3c(ccc5cccc-4c35)C73c4cc(-c5ccccc5)ccc4-c4ccc(-c5ccccc5)cc43)c2)cc1]
34
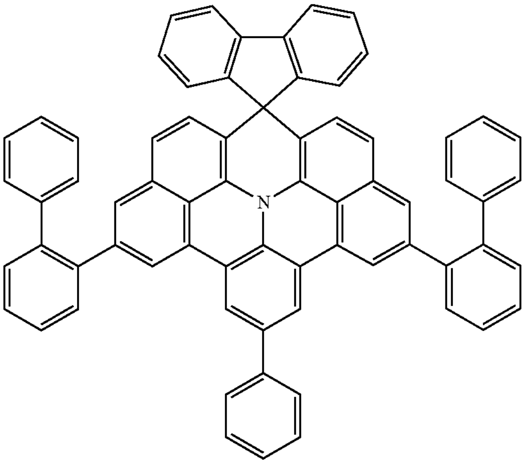 [SMILES: c1ccc(-c2cc3c4c(c2)-c2cc(-c5ccccc5-c5ccccc5)cc5ccc6c(c25)N4c2c(ccc4cc(-c5ccccc5-c5ccccc5)cc-3c24)C62c3ccccc3-c3ccccc32)cc1]
35

-continued
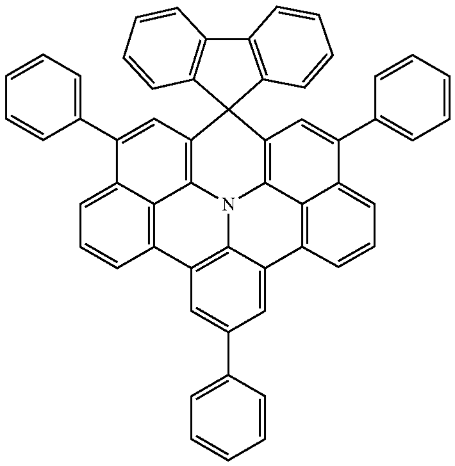 [SMILES: c1ccc(-c2cc3c4c(c2)-c2cccc5c(-c6ccccc6)cc6c(c25)N4c2c(cc(-c4ccccc4)c4cccc-3c24)C62c3ccccc3-c3ccccc32)cc1]
36
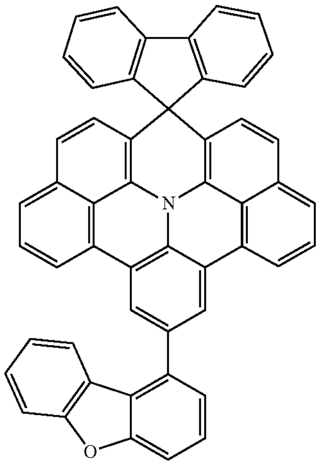 [SMILES: c1ccc2c(c1)-c1ccccc1C21c2ccc3cccc4c3c2N2c3c-4cc(-c4cccc5oc6ccccc6c45)cc3-c3cccc4ccc1c2c34]
37
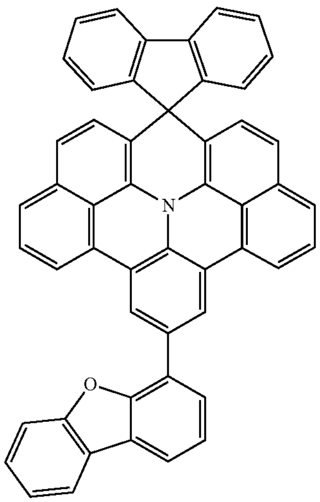 [SMILES: c1ccc2c(c1)-c1ccccc1C21c2ccc3cccc4c3c2N2c3c-4cc(-c4cccc5c4oc4ccccc45)cc3-c3cccc4ccc1c2c34]
38

-continued
39
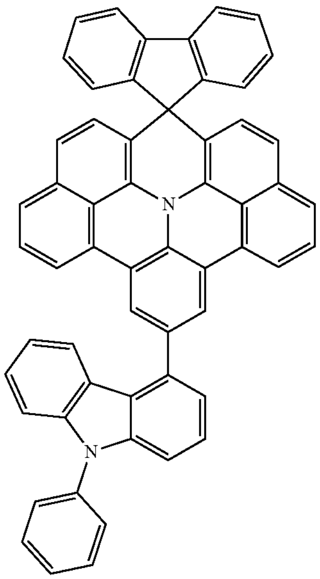 [SMILES: c1ccc(-n2c3ccccc3c3c(-c4cc5c6c(c4)-c4cccc7ccc8c(c47)N6c4c(ccc6cccc-5c46)C84c5ccccc5-c5ccccc54)cccc32)cc1]
40
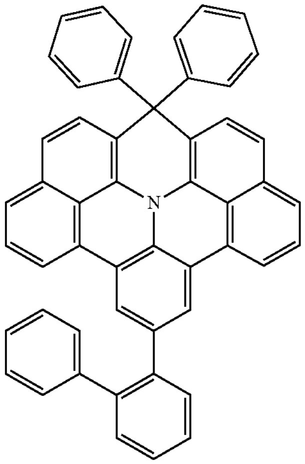 [SMILES: c1ccc(-c2ccccc2-c2cc3c4c(c2)-c2cccc5ccc6c(c25)N4c2c(ccc4cccc-3c24)C6(c2ccccc2)c2ccccc2)cc1]
41
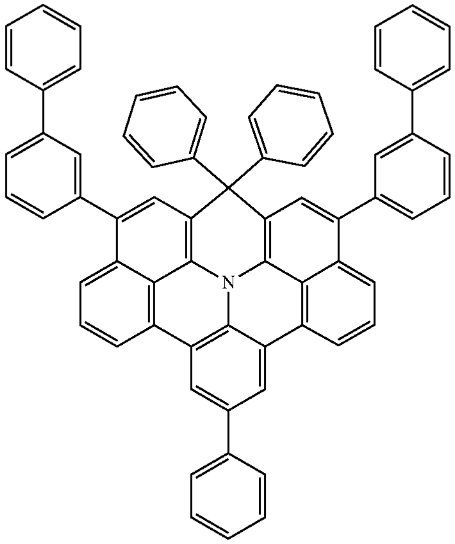 [SMILES: c1ccc(-c2cccc(-c3cc4c5c6c(cccc36)-c3cc(-c6ccccc6)cc6c3N5c3c(cc(-c5cccc(-c7ccccc7)c5)c5cccc-6c35)C4(c3ccccc3)c3ccccc3)c2)cc1]

-continued
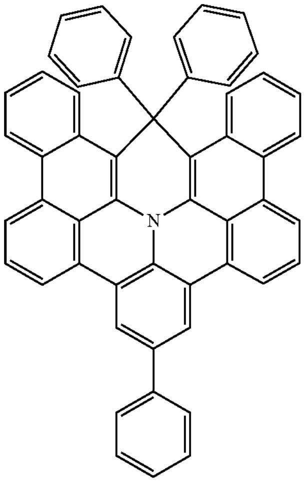 [SMILES: c1ccc(-c2cc3c4c(c2)-c2cccc5c2c2c(c6ccccc65)C(c5ccccc5)(c5ccccc5)c5c(c6c-3cccc6c3ccccc53)N42)cc1]
42
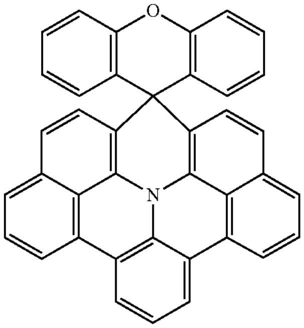 [SMILES: c1ccc2c(c1)Oc1ccccc1C21c2ccc3cccc4c3c2N2c3c-4cccc3-c3cccc4ccc1c2c34]
43
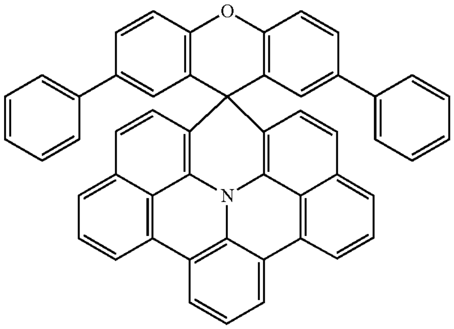 [SMILES: c1ccc(-c2ccc3c(c2)C2(c4cc(-c5ccccc5)ccc4O3)c3ccc4cccc5c4c3N3c4c-5cccc4-c4cccc5ccc2c3c45)cc1]
44
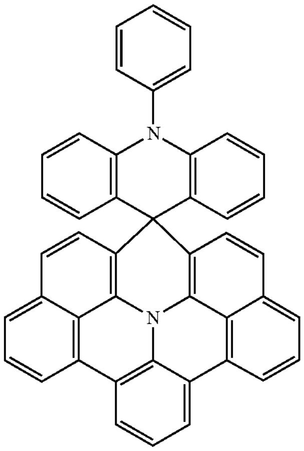 [SMILES: c1ccc(N2c3ccccc3C3(c4ccccc42)c2ccc4cccc5c4c2N2c4c-5cccc4-c4cccc5ccc3c2c45)cc1]
45

-continued
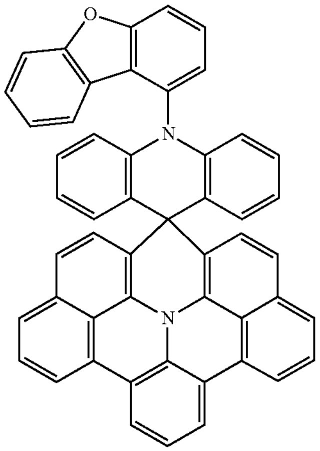 [SMILES: c1cc2c3c(c1)-c1cccc4ccc5c(c14)N3c1c(ccc3cccc-2c13)C51c2ccccc2N(c2cccc3oc4ccccc4c23)c2ccccc21]
46
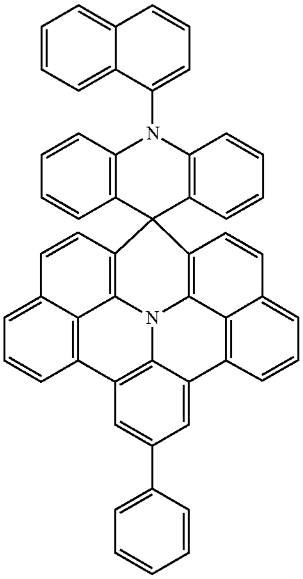 [SMILES: c1ccc(-c2cc3c4c(c2)-c2cccc5ccc6c(c25)N4c2c(ccc4cccc-3c24)C62c3ccccc3N(c3cccc4ccccc34)c3ccccc32)cc1]
47
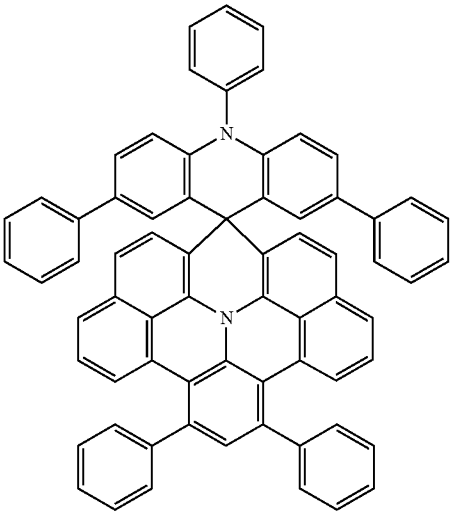 [SMILES: c1ccc(-c2ccc3c(c2)C2(c4cc(-c5ccccc5)ccc4N3c3ccccc3)c3ccc4cccc5c4c3N3c4c-5c(-c5ccccc5)cc(-c5ccccc5)c4-c4cccc5ccc2c3c45)cc1]
48

-continued
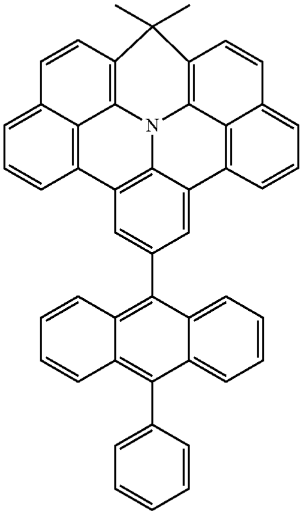 [SMILES: CC1(C)c2ccc3cccc4c3c2N2c3c-4cc(-c4c5ccccc5c(-c5ccccc5)c5ccccc45)cc3-c3cccc4ccc1c2c34]
49
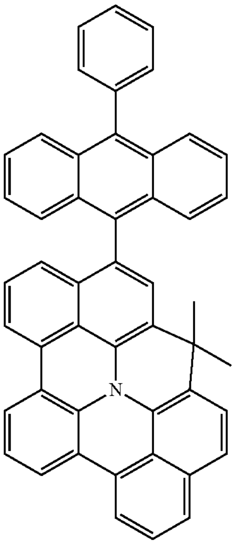 [SMILES: CC1(C)c2ccc3cccc4c3c2N2c3c-4cccc3-c3cccc4c(-c5c6ccccc6c(-c6ccccc6)c6ccccc56)cc1c2c34]
50
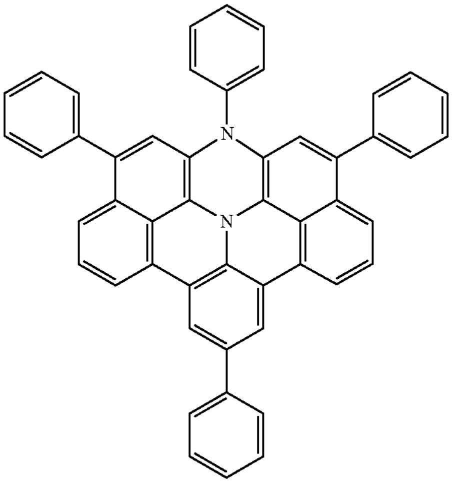 [SMILES: c1ccc(-c2cc3c4cccc5c(-c6ccccc6)cc6c(c54)n4c3c(c2)c2cccc3c(-c5ccccc5)cc(c4c32)n6-c2ccccc2)cc1]
51

-continued
52
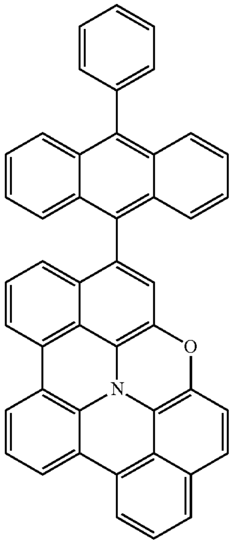 [SMILES: c1ccc(-c2c3ccccc3c(-c3cc4oc5ccc6cccc7c8cccc9c%10cccc3c%10c4n(c89)c5c67)c3ccccc23)cc1]
53
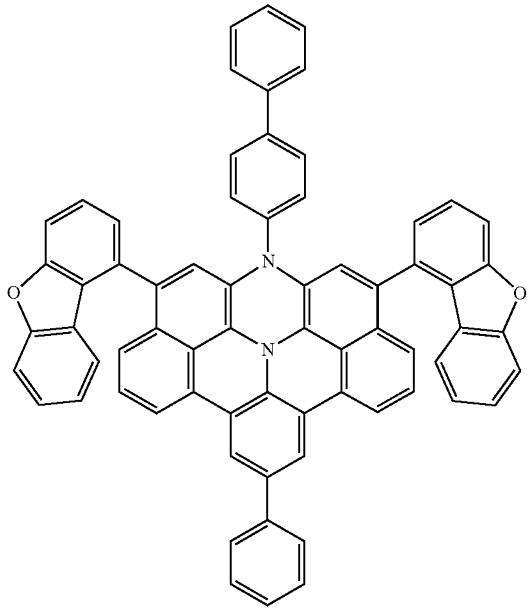 [SMILES: c1ccc(-c2ccc(-n3c4cc(-c5cccc6oc7ccccc7c56)c5cccc6c7cc(-c8ccccc8)cc8c9cccc%10c(-c%11cccc%12oc%13ccccc%13c%11%12)cc3c(c%109)n(c78)c4c56)cc2)cc1]
54
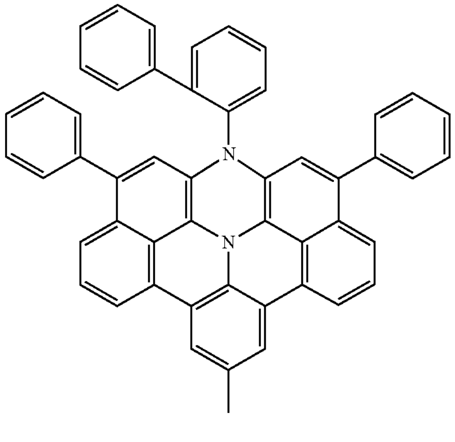 [SMILES: Cc1cc2c3cccc4c(-c5ccccc5)cc5c(c43)n3c2c(c1)c1cccc2c(-c4ccccc4)cc(c3c21)n5-c1ccccc1-c1ccccc1]

-continued
55
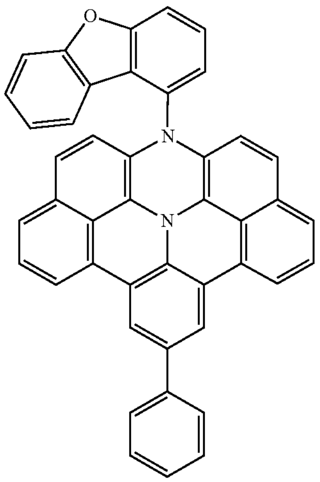 [SMILES: c1ccc(-c2cc3c4cccc5ccc6c(c54)n4c3c(c2)c2cccc3ccc(c4c32)n6-c2cccc3oc4ccccc4c23)cc1]
56
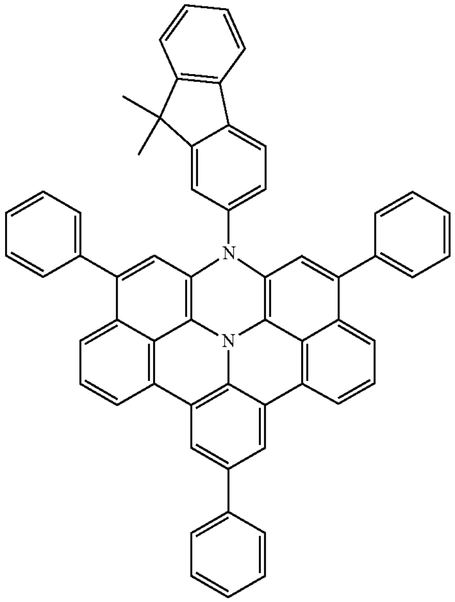 [SMILES: CC1(C)c2ccccc2-c2ccc(-n3c4cc(-c5ccccc5)c5cccc6c7cc(-c8ccccc8)cc8c9cccc%10c(-c%11ccccc%11)cc3c(c%109)n(c78)c4c56)cc21]
57
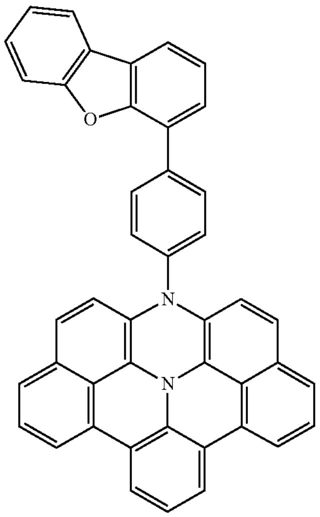 [SMILES: c1ccc2c(c1)oc1c(-c3ccc(-n4c5ccc6cccc7c8cccc9c%10cccc%11ccc4c(c%11%10)n(c89)c5c67)cc3)cccc12]

-continued
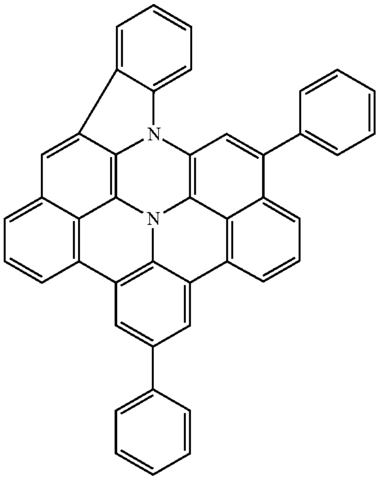 [SMILES: c1ccc(-c2cc3c4cccc5c(-c6ccccc6)cc6c(c54)n4c3c(c2)c2cccc3cc5c7ccccc7n6c5c4c32)cc1]
58
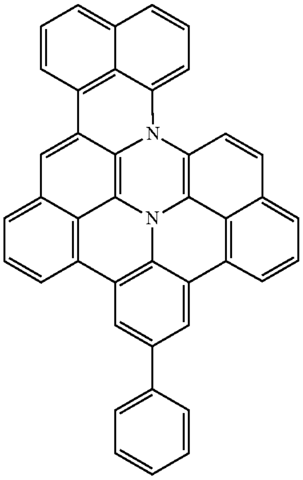 [SMILES: c1ccc(-c2cc3c4cccc5ccc6c(c54)n4c3c(c2)c2cccc3cc5c7cccc8cccc(c87)n6c5c4c32)cc1]
59
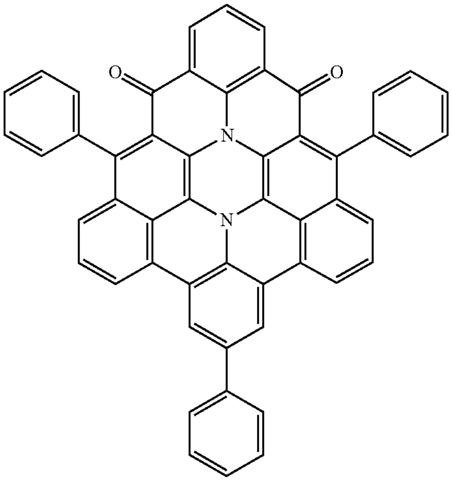 [SMILES: O=c1c2cccc3c(=O)c4c(-c5ccccc5)c5cccc6c7cc(-c8ccccc8)cc8c9cccc%10c(-c%11ccccc%11)c1c1c(c%109)n(c87)c(c56)c4n1c23]
60

-continued
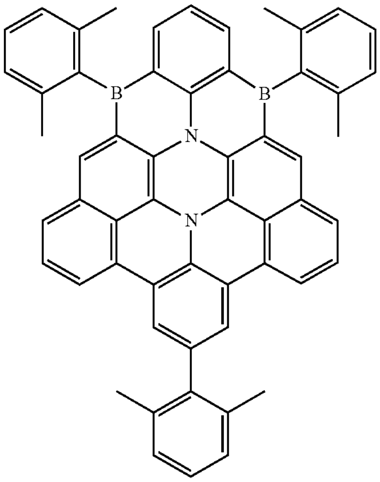 [SMILES: Cc1cccc(C)c1B1c2cccc3c2-n2c4c1cc1cccc5c6cc(-c7c(C)cccc7C)cc7c8cccc9cc(c2c(c98)n(c67)c4c15)B3c1c(C)cccc1C]
61
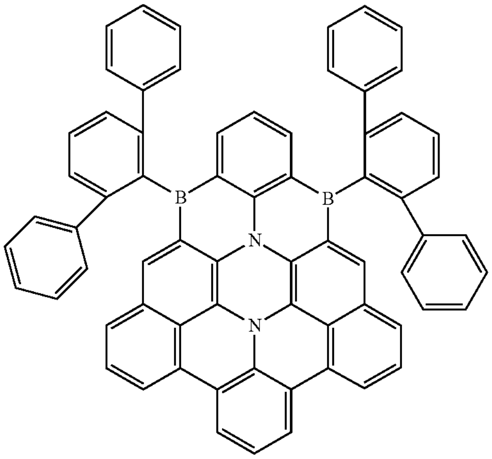 [SMILES: c1ccc(-c2cccc(-c3ccccc3)c2B2c3cccc4c3-n3c5c2cc2cccc6c7cccc8c9cccc%10cc(c3c(c%109)n(c78)c5c26)B4c2c(-c3ccccc3)cccc2-c2ccccc2)cc1]
62
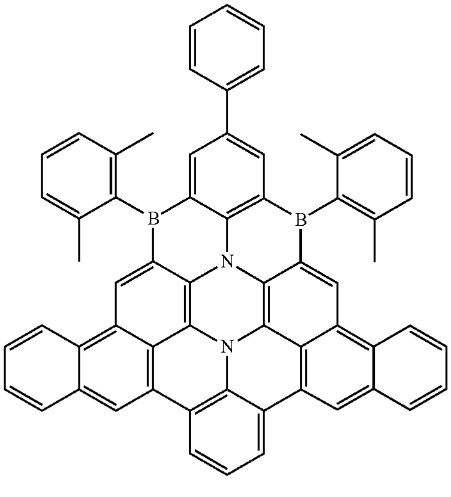 [SMILES: Cc1cccc(C)c1B1c2cc(-c3ccccc3)cc3c2-n2c4c1cc1c5ccccc5cc5c6cccc7c8cc9ccccc9c9cc(c2c(c98)n(c67)c4c15)B3c1c(C)cccc1C]
63

-continued
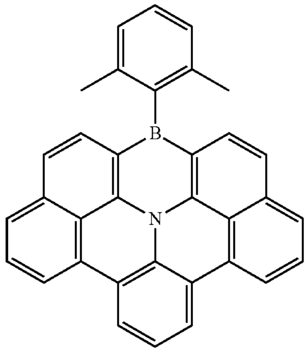 [SMILES: Cc1cccc(C)c1B1c2ccc3cccc4c3c2N2c3c-4cccc3-c3cccc4ccc1c2c34]
64
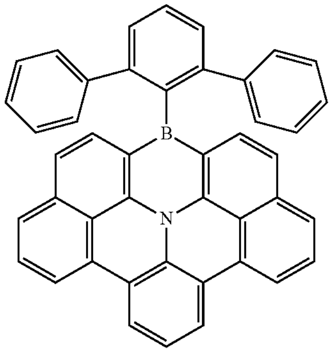 [SMILES: c1ccc(-c2cccc(-c3ccccc3)c2B2c3ccc4cccc5c4c3N3c4c-5cccc4-c4cccc5ccc2c3c45)cc1]
65
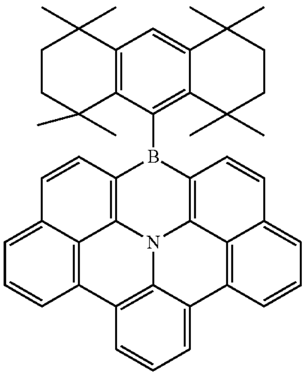 [SMILES: CC1(C)CCC(C)(C)c2c1cc1c(c2B2c3ccc4cccc5c4c3N3c4c-5cccc4-c4cccc5ccc2c3c45)C(C)(C)CCC1(C)C]
66

-continued
67
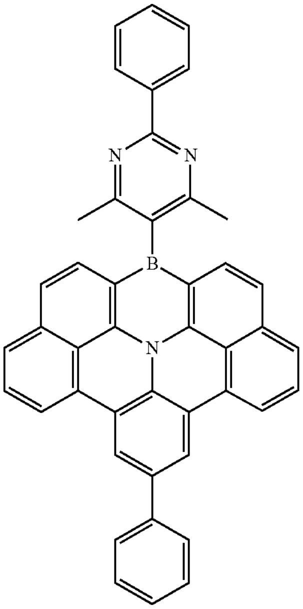 [SMILES: Cc1nc(-c2ccccc2)nc(C)c1B1c2ccc3cccc4c3c2N2c3c-4cc(-c4ccccc4)cc3-c3cccc4ccc1c2c34]
68
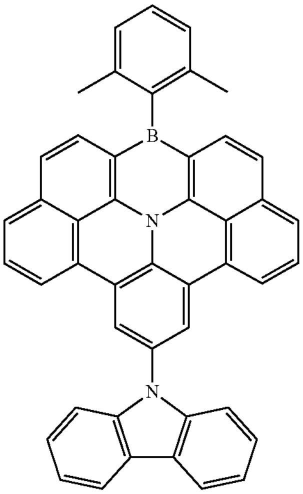 [SMILES: Cc1cccc(C)c1B1c2ccc3cccc4c3c2N2c3c-4cc(-n4c5ccccc5c5ccccc54)cc3-c3cccc4ccc1c2c34]
69
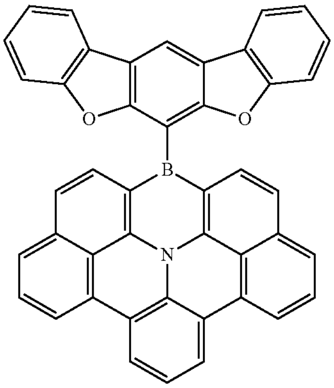 [SMILES: c1cc2c3c(c1)-c1cccc4ccc5c(c14)N3c1c(ccc3cccc-2c13)B5c1c2oc3ccccc3c2cc2c1oc1ccccc12]

-continued
70
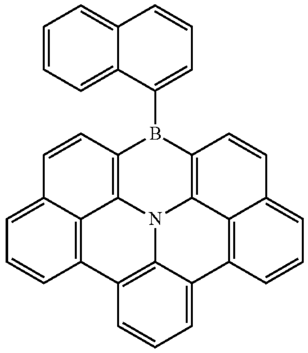 [SMILES: c1cc2c3c(c1)-c1cccc4ccc5c(c14)N3c1c(ccc3cccc-2c13)B5c1cccc2ccccc12]
71
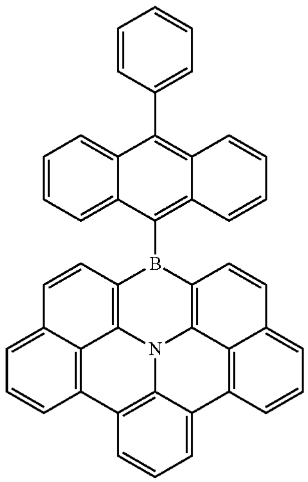 [SMILES: c1ccc(-c2c3ccccc3c(B3c4ccc5cccc6c5c4N4c5c-6cccc5-c5cccc6ccc3c4c56)c3ccccc23)cc1]
72
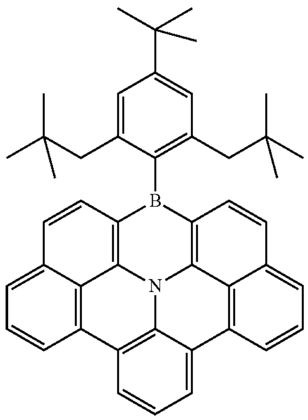 [SMILES: CC(C)(C)Cc1cc(C(C)(C)C)cc(CC(C)(C)C)c1B1c2ccc3cccc4c3c2N2c3c-4cccc3-c3cccc4ccc1c2c34]

-continued
73
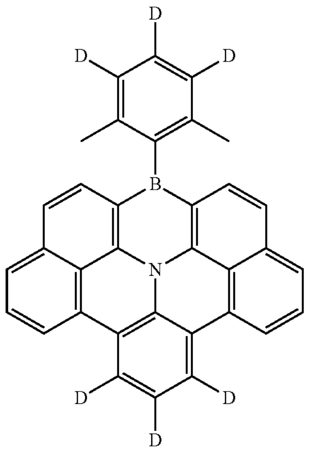 [SMILES: [2H]c1c([2H])c(C)c(B2c3ccc4cccc5c4c3N3c4c-5c([2H])c([2H])c([2H])c4-c4cccc5ccc2c3c45)c(C)c1[2H]]
74
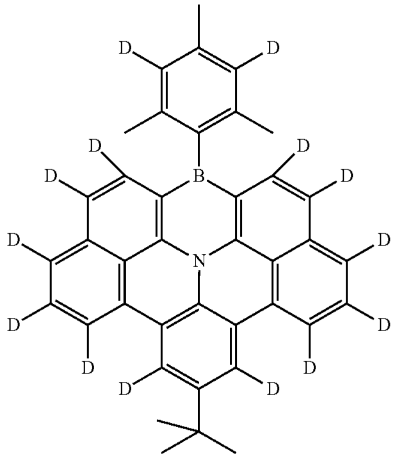 [SMILES: [2H]c1c(C)c([2H])c(C)c(B2c3c([2H])c([2H])c4c([2H])c([2H])c([2H])c5c4c3N3c4c-5c([2H])c(C(C)(C)C)c([2H])c4-c4c([2H])c([2H])c([2H])c5c([2H])c([2H])c2c3c45)c1C]
75
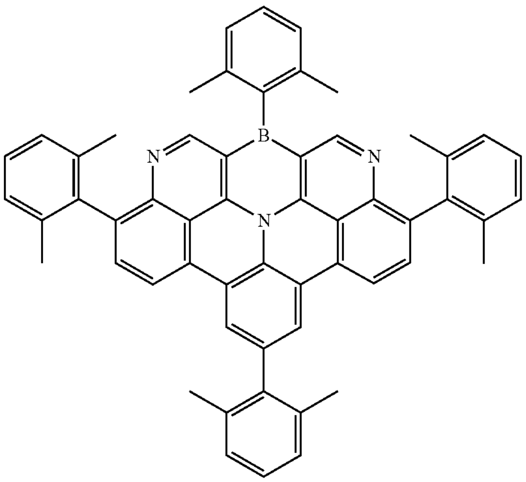 [SMILES: Cc1cccc(C)c1B1c2cnc3c(-c4c(C)cccc4C)ccc4c3c2N2c3c-4cc(-c4c(C)cccc4C)cc3-c3ccc(-c4c(C)cccc4C)c4ncc1c2c34]

-continued
76
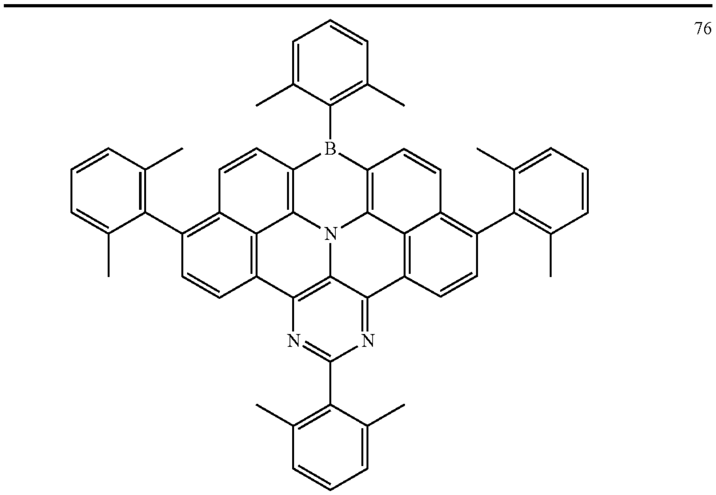
77
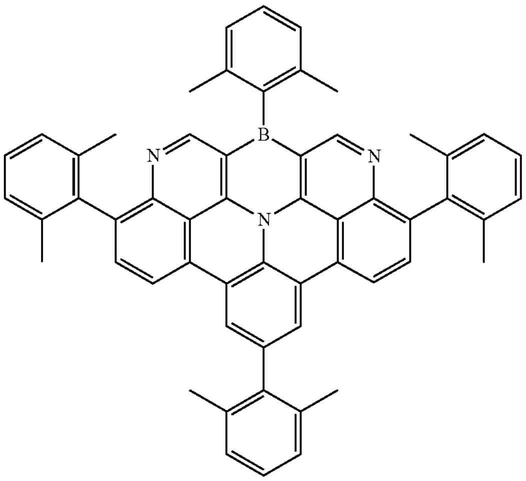 [SMILES: Cc1cccc(C)c1B1c2cnc3c(-c4c(C)cccc4C)ccc4c3c2N2c3c-4cc(-c4c(C)cccc4C)cc3-c3ccc(-c4c(C)cccc4C)c4ncc1c2c34]
78
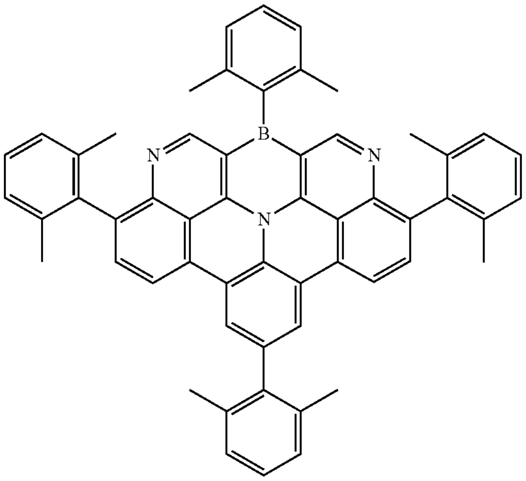 [SMILES: Cc1cccc(C)c1B1c2cnc3c(-c4c(C)cccc4C)ccc4c3c2N2c3c-4cc(-c4c(C)cccc4C)cc3-c3ccc(-c4c(C)cccc4C)c4ncc1c2c34]

-continued
79
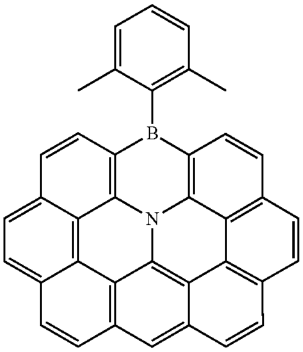 [SMILES: Cc1cccc(C)c1B1c2ccc3ccc4ccc5cc6ccc7ccc8ccc1c1c8c7c6c6c5c4c3c2N16]
80
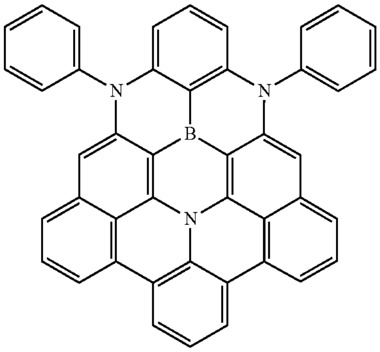 [SMILES: c1ccc(N2c3cccc4c3B3c5c2cc2cccc6c2c5N2c5c-6cccc5-c5cccc6cc(c3c2c56)N4c2ccccc2)cc1]
81
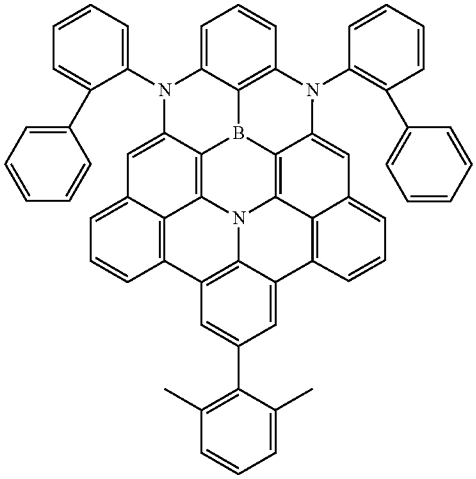 [SMILES: Cc1cccc(C)c1-c1cc2c3c(c1)-c1cccc4cc5c6c(c14)N3c1c3c(cc4cccc-2c14)N(c1ccccc1-c1ccccc1)c1cccc(c1B36)N5c1ccccc1-c1ccccc1]

-continued
82
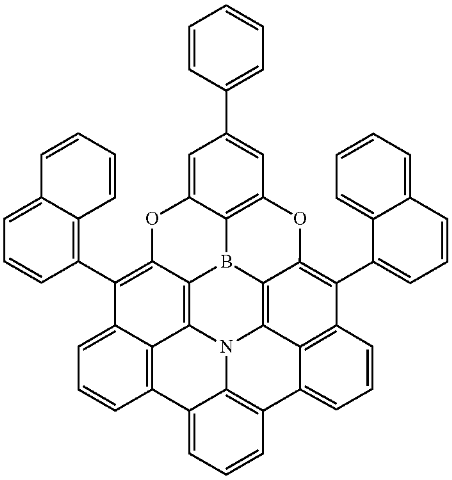 [SMILES: c1ccc(-c2cc3c4c(c2)Oc2c5c6c7c(cccc7c2-c2cccc7ccccc27)-c2cccc7c2N6c2c(c(c(-c6cccc8ccccc68)c6cccc-7c26)O3)B45)cc1]
83
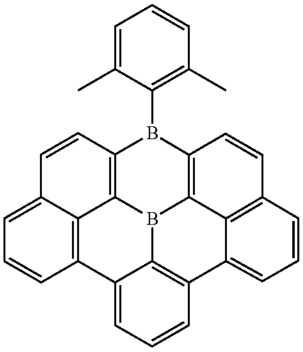 [SMILES: Cc1cccc(C)c1B1c2ccc3cccc4c3c2B2c3c-4cccc3-c3cccc4ccc1c2c34]
84
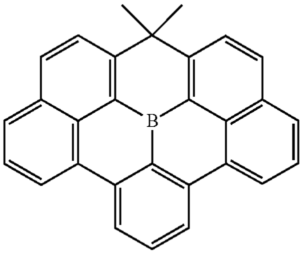 [SMILES: CC1(C)c2ccc3cccc4c3c2B2c3c-4cccc3-c3cccc4ccc1c2c34]
85
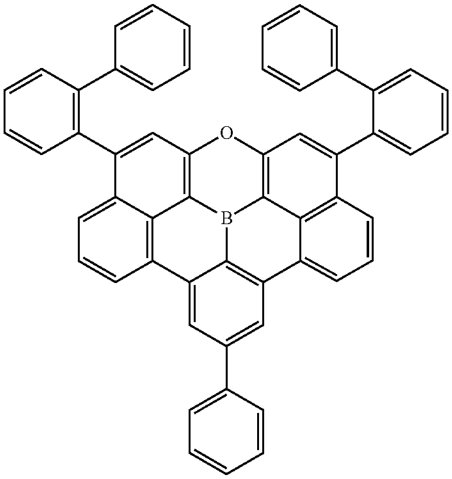 [SMILES: c1ccc(-c2cc3c4c(c2)-c2cccc5c(-c6ccccc6-c6ccccc6)cc6c(c25)B4c2c(cc(-c4ccccc4-c4ccccc4)c4cccc-3c24)O6)cc1]

-continued
86
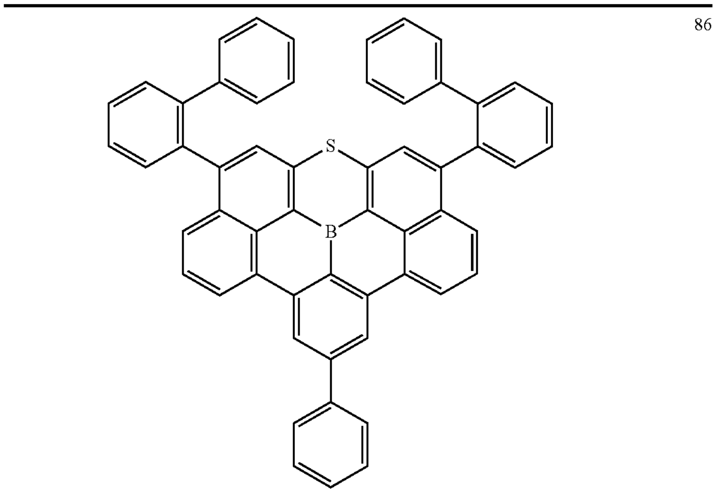
87
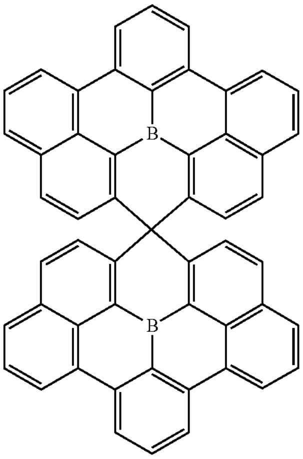 [SMILES: c1cc2c3c(c1)-c1cccc4ccc5c(c14)B3c1c(ccc3cccc-2c13)C51c2ccc3cccc4c3c2B2c3c-4cccc3-c3cccc4ccc1c2c34]
88
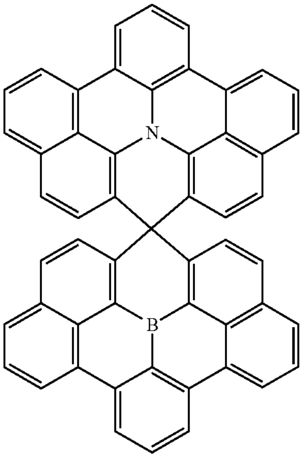

-continued
89
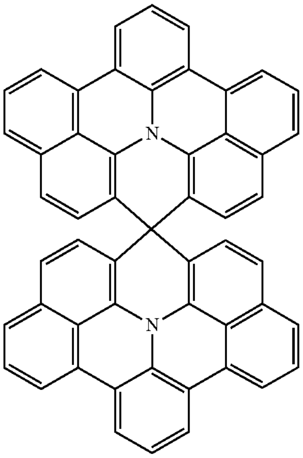
90
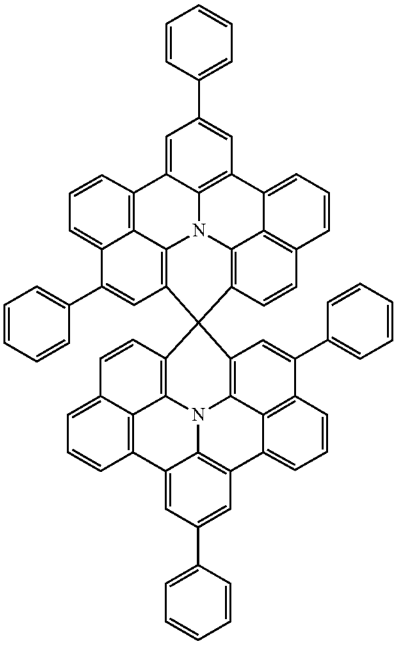 [SMILES: c1ccc(-c2cc3c4c(c2)-c2cccc5c(-c6ccccc6)cc6c(c25)N4c2c(ccc4cccc-3c24)C62c3ccc4cccc5c4c3N3c4c-5cc(-c5ccccc5)cc4-c4cccc5c(-c6ccccc6)cc2c3c45)cc1]
91
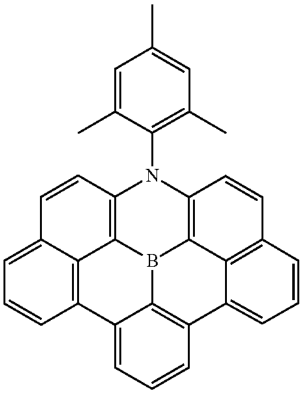 [SMILES: Cc1cc(C)c(N2c3ccc4cccc5c4c3B3c4c-5cccc4-c4cccc5ccc2c3c45)c(C)c1]

-continued
92
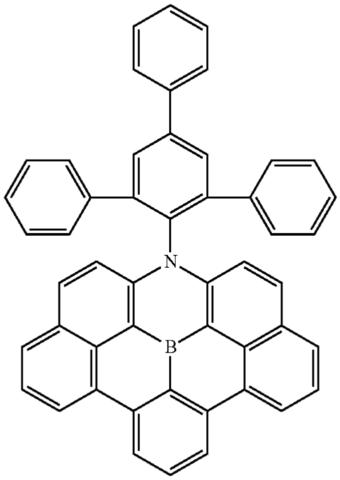 [SMILES: c1ccc(-c2cc(-c3ccccc3)c(N3c4ccc5cccc6c5c4B4c5c-6cccc5-c5cccc6ccc3c4c56)c(-c3ccccc3)c2)cc1]
93
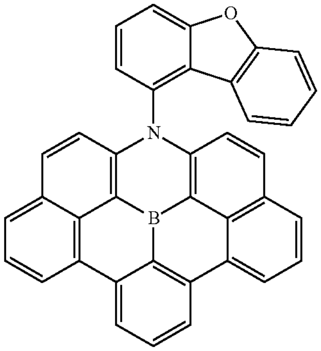 [SMILES: c1cc2c3c(c1)-c1cccc4ccc5c(c14)B3c1c(ccc3cccc-2c13)N5c1cccc2oc3ccccc3c12]
94
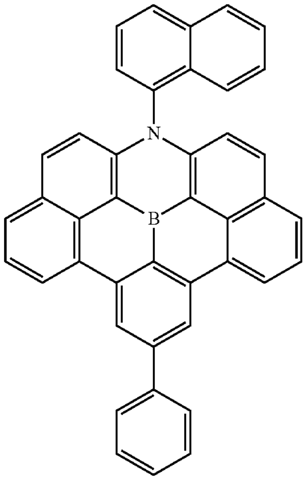 [SMILES: c1ccc(-c2cc3c4c(c2)-c2cccc5ccc6c(c25)B4c2c(ccc4cccc-3c24)N6c2cccc3ccccc23)cc1]

-continued
95
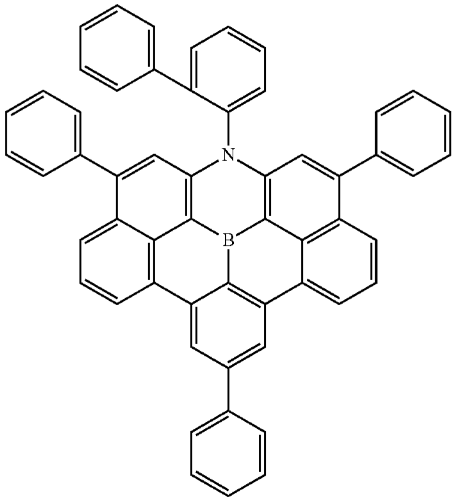 [SMILES: c1ccc(-c2cc3c4c(c2)-c2cccc5c(-c6ccccc6)cc6c(c25)B4c2c(cc(-c4ccccc4)c4cccc-3c24)N6c2ccccc2-c2ccccc2)cc1]
96
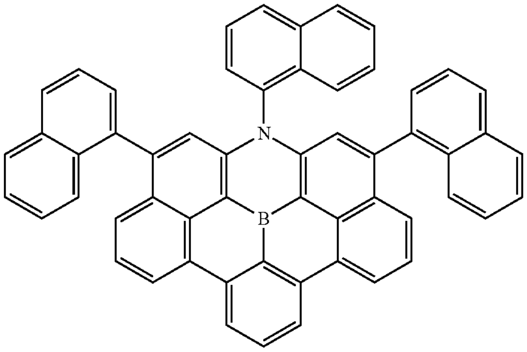 [SMILES: c1cc2c3c(c1)-c1cccc4c(-c5cccc6ccccc56)cc5c(c14)B3c1c(cc(-c3cccc4ccccc34)c3cccc-2c13)N5c1cccc2ccccc12]
97
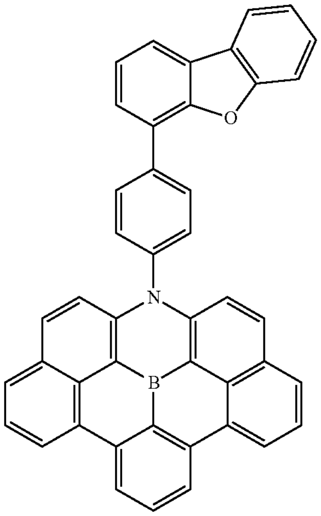 [SMILES: c1cc2c3c(c1)-c1cccc4ccc5c(c14)B3c1c(ccc3cccc-2c13)N5c1ccc(-c2cccc3c2oc2ccccc23)cc1]

-continued
98
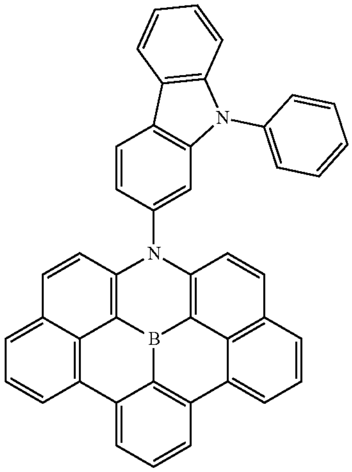 [SMILES: c1ccc(-n2c3ccccc3c3ccc(N4c5ccc6cccc7c6c5B5c6c-7cccc6-c6cccc7ccc4c5c67)cc32)cc1]
99
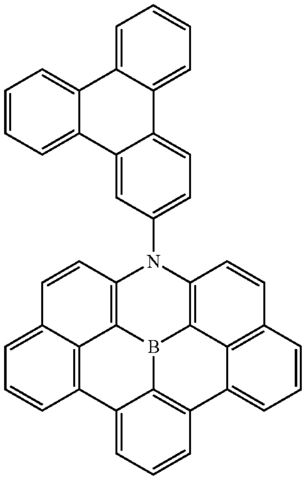 [SMILES: c1cc2c3c(c1)-c1cccc4ccc5c(c14)B3c1c(ccc3cccc-2c13)N5c1ccc2c3ccccc3c3ccccc3c2c1]
100
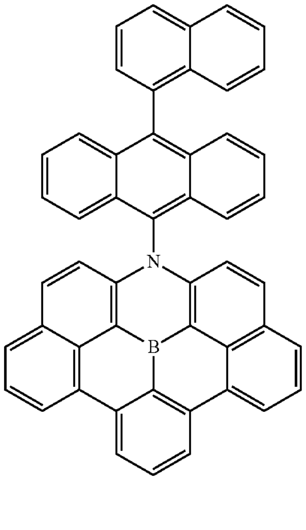 [SMILES: c1cc2c3c(c1)-c1cccc4ccc5c(c14)B3c1c(ccc3cccc-2c13)N5c1c2ccccc2c(-c2cccc3ccccc23)c2ccccc12]

-continued
101
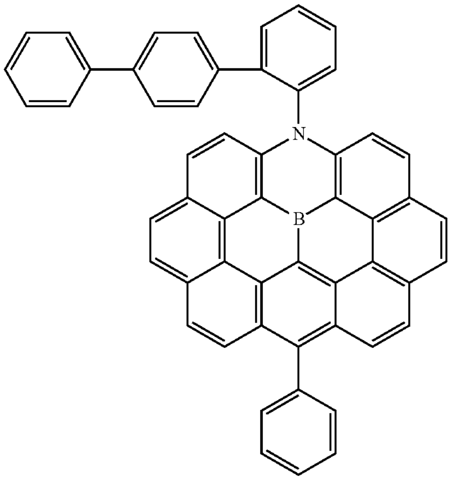 [SMILES: c1ccc(-c2ccc(-c3ccccc3N3c4ccc5ccc6ccc7c(-c8ccccc8)c8ccc9ccc%10ccc3c3c%10c9c8c8c7c6c5c4B38)cc2)cc1]
102
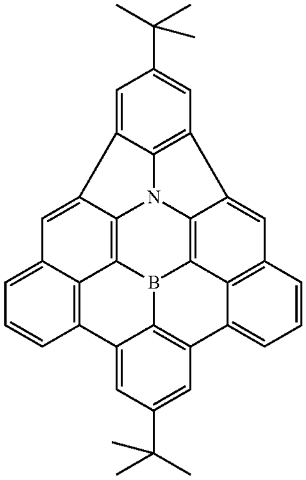 [SMILES: CC(C)(C)c1cc2c3c(c1)-c1cccc4cc5c6cc(C(C)(C)C)cc7c8cc9cccc-2c9c2c8n(c5c(c14)B32)c76]
103
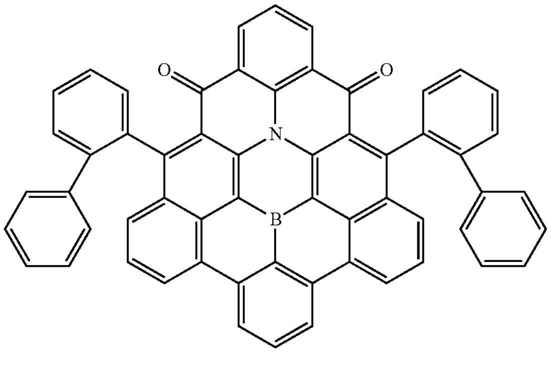 [SMILES: O=c1c2cccc3c(=O)c4c(-c5ccccc5-c5ccccc5)c5cccc6c5c5c4n(c4c7c8c(cccc8c(-c8ccccc8-c8ccccc8)c14)-c1cccc-6c1B75)c23]

-continued
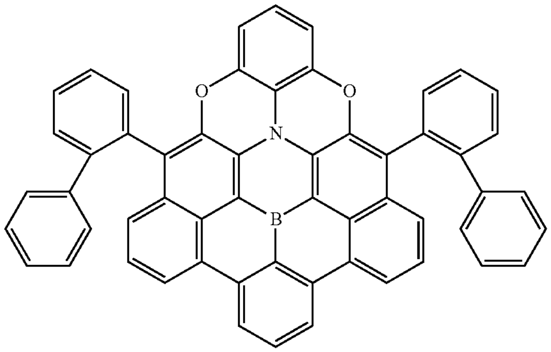 [SMILES: c1ccc(-c2ccccc2-c2c3c4c5c6c(cccc26)-c2cccc6c2B5c2c5c(c(-c7ccccc7-c7ccccc7)c7cccc-6c27)Oc2cccc(c2N45)O3)cc1]
104
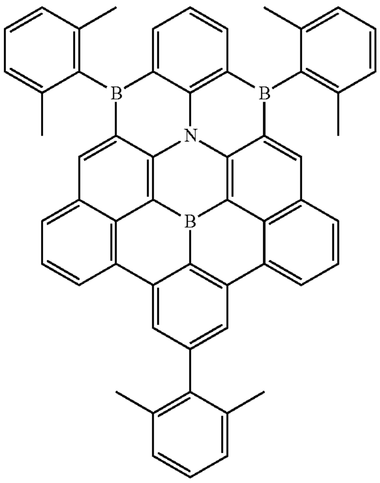 [SMILES: Cc1cccc(C)c1B1c2cccc3c2N2c4c1cc1cccc5c1c4B1c4c-5cc(-c5c(C)cccc5C)cc4-c4cccc5cc(c2c1c45)B3c1c(C)cccc1C]
105
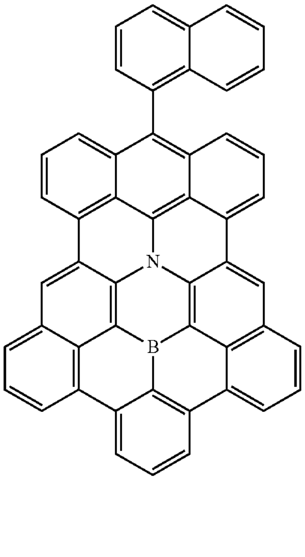 [SMILES: c1cc2c3c(c1)-c1cccc4cc5c6c(c14)B3c1c3c(cc4cccc-2c14)-c1cccc2c(-c4cccc7ccccc47)c4cccc-5c4c(c12)N36]
106

-continued
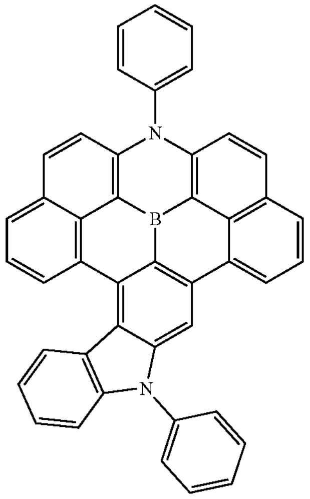 [SMILES: c1ccc(N2c3ccc4cccc5c4c3B3c4c-5cc5c(c4-c4cccc6ccc2c3c46)c2ccccc2n5-c2ccccc2)cc1]
107
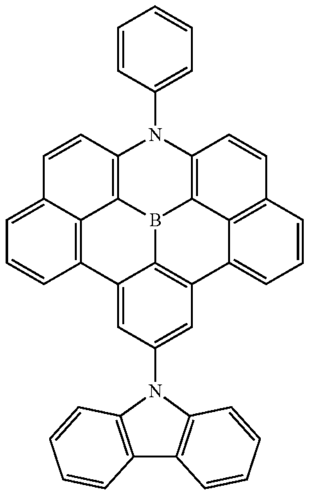 [SMILES: c1ccc(N2c3ccc4cccc5c4c3B3c4c-5cc(-n5c6ccccc6c6ccccc65)cc4-c4cccc5ccc2c3c45)cc1]
108
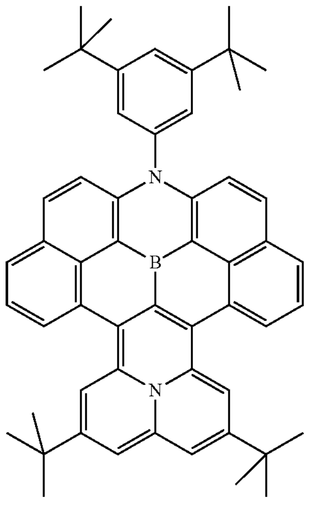 [SMILES: CC(C)(C)C1=CC2=CC(C(C)(C)C)=CC3=C4C5=C(C(=C1)N23)c1cccc2ccc3c(c12)B5c1c(ccc2cccc4c12)N3c1cc(C(C)(C)C)cc(C(C)(C)C)c1]
109

-continued
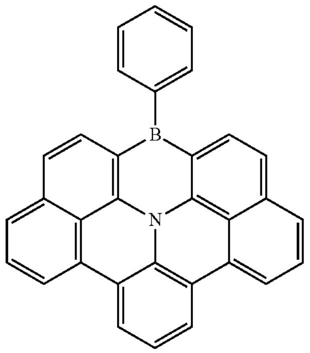
110
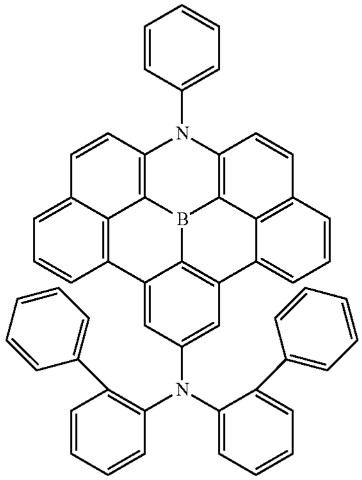 [SMILES: c1ccc(-c2ccccc2N(c2cc3c4c(c2)-c2cccc5ccc6c(c25)B4c2c(ccc4cccc-3c24)N6c2ccccc2)c2ccccc2-c2ccccc2)cc1]
111
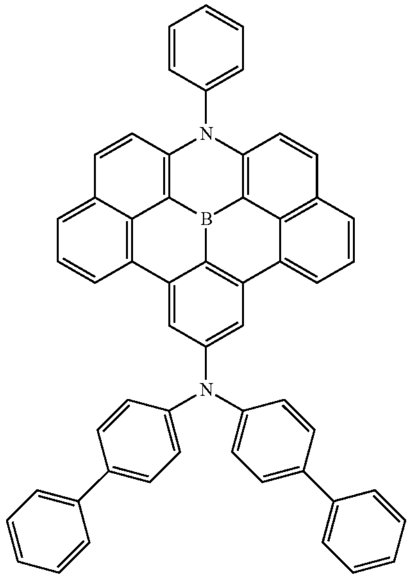 [SMILES: c1ccc(-c2ccc(N(c3ccc(-c4ccccc4)cc3)c3cc4c5c(c3)-c3cccc6ccc7c(c36)B5c3c(ccc5cccc-4c35)N7c3ccccc3)cc2)cc1]
112

-continued
113
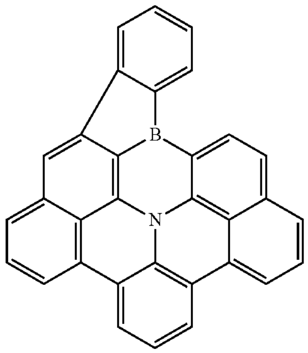 [SMILES: c1ccc2c(c1)B1c3ccc4cccc5c4c3N3c4c-5cccc4-c4cccc5cc-2c1c3c45]
114
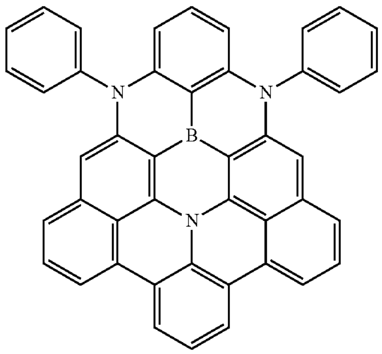 [SMILES: c1ccc(N2c3cccc4c3B3c5c2cc2cccc6c2c5N2c5c-6cccc5-c5cccc6cc(c3c2c56)N4c2ccccc2)cc1]
115
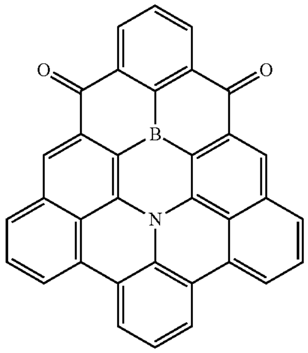
116
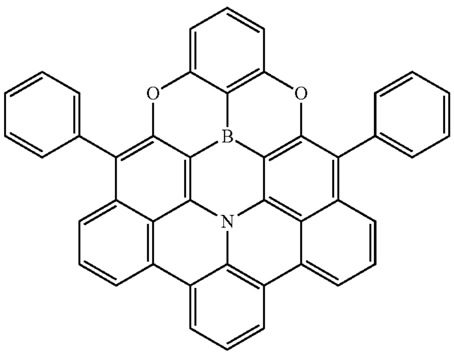 [SMILES: c1ccc(-c2c3c4c5c6c(cccc26)-c2cccc6c2N5c2c5c(c(-c7ccccc7)c7cccc-6c27)Oc2cccc(c2B45)O3)cc1]

-continued
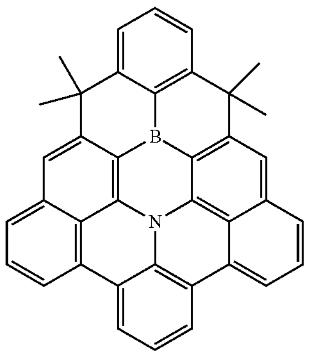 [SMILES: CC1(C)c2cccc3c2B2c4c1cc1cccc5c1c4N1c4c-5cccc4-c4cccc5cc(c2c1c45)C3(C)C]
117
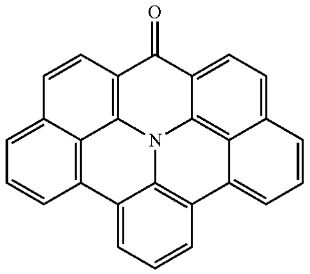 [SMILES: O=c1c2ccc3cccc4c5cccc6c7cccc8ccc1c(c87)n(c56)c2c34]
118
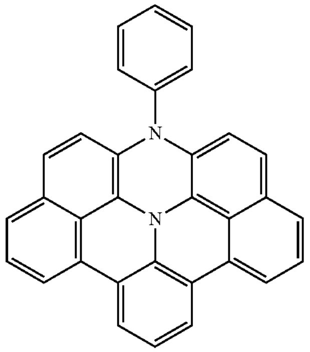 [SMILES: c1ccc(-n2c3ccc4cccc5c6cccc7c8cccc9ccc2c(c98)n(c67)c3c45)cc1]
119
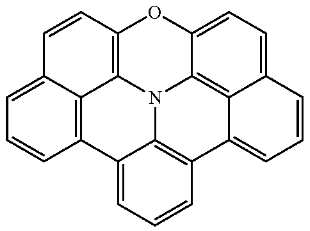 [SMILES: c1cc2ccc3oc4ccc5cccc6c7cccc8c(c1)c2c3n(c87)c4c56]
120
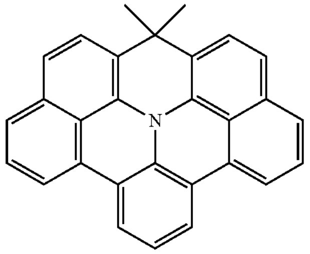 [SMILES: CC1(C)c2ccc3cccc4c3c2N2c3c-4cccc3-c3cccc4ccc1c2c34]
121

-continued
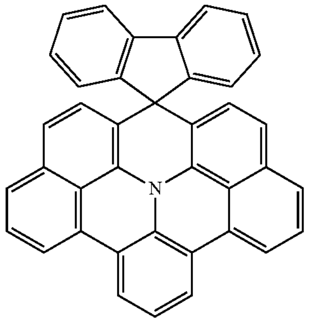 [SMILES: c1ccc2c(c1)-c1ccccc1C21c2ccc3cccc4c3c2N2c3c-4cccc3-c3cccc4ccc1c2c34]
122
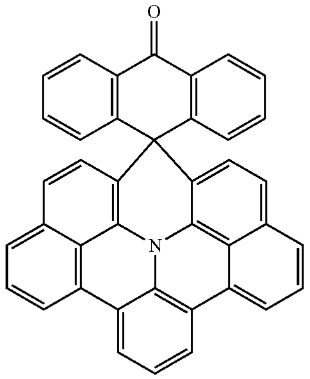 [SMILES: O=C1c2ccccc2C2(c3ccccc31)c1ccc3cccc4c3c1N1c3c-4cccc3-c3cccc4ccc2c1c34]
123
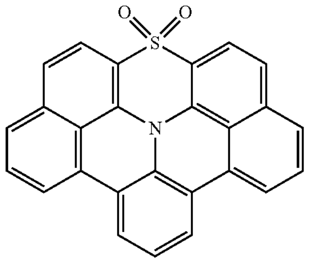 [SMILES: O=S1(=O)c2ccc3cccc4c3c2N2c3c-4cccc3-c3cccc4ccc1c2c34]
124
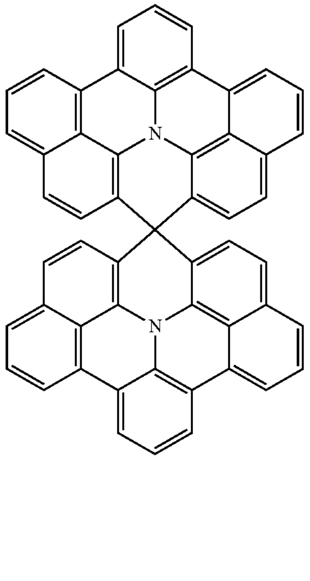 [SMILES: c1cc2c3c(c1)-c1cccc4ccc5c(c14)N3c1c(ccc3cccc-2c13)C51c2ccc3cccc4c3c2N2c3c-4cccc3-c3cccc4ccc1c2c34]
125

-continued
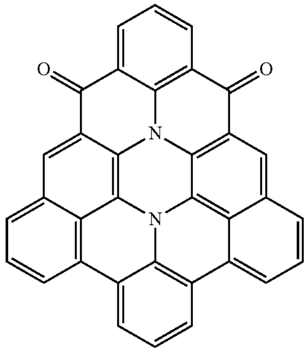 [SMILES: O=c1c2cccc3c(=O)c4cc5cccc6c7cccc8c9cccc%10cc1c1c(c%109)n(c87)c(c56)c4n1c23]
126
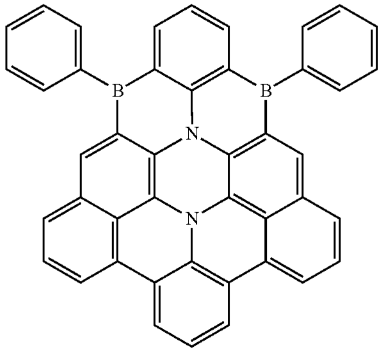
127
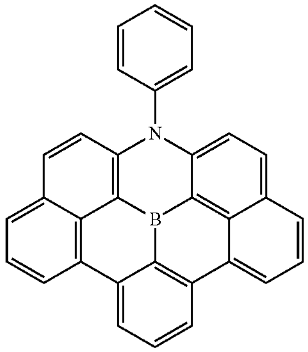
128
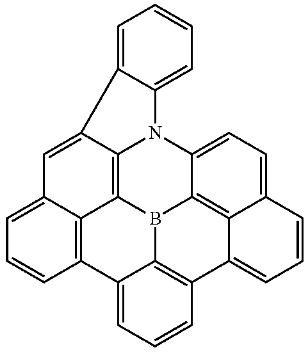 [SMILES: c1cc2c3c(c1)-c1cccc4cc5c6ccccc6n6c5c(c14)B3c1c-6ccc3cccc-2c13]
129

-continued
130
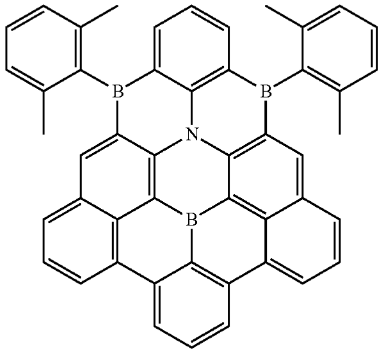 [SMILES: Cc1cccc(C)c1B1c2cccc3c2N2c4c1cc1cccc5c1c4B1c4c-5cccc4-c4cccc5cc(c2c1c45)B3c1c(C)cccc1C]
131
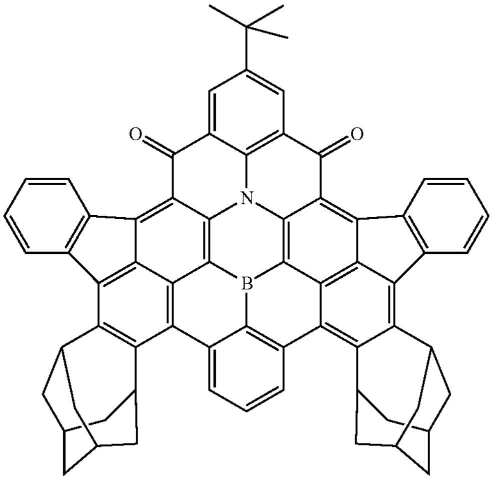 [SMILES: CC(C)(C)c1cc2c(=O)c3c4c5ccccc5c5c6c(c7c(c8c3n3c9c%10c%11c(c%12c(c%13c%14ccccc%14c(c9c(=O)c(c1)c23)c%11%13)C1CC2CC(CC%12C2)C1)-c1cccc-7c1B8%10)c54)C1CC2CC(C1)CC6C2]
132
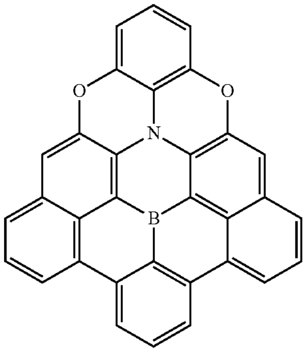 [SMILES: c1cc2c3c(c1)Oc1cc4cccc5c4c4c1N3c1c(cc3cccc6c3c1B4c1c-6cccc1-5)O2]
133
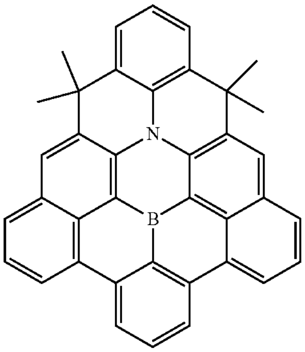 [SMILES: CC1(C)c2cccc3c2N2c4c1cc1cccc5c1c4B1c4c-5cccc4-c4cccc5cc(c2c1c45)C3(C)C]

-continued
134
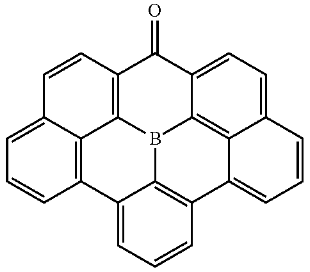
135
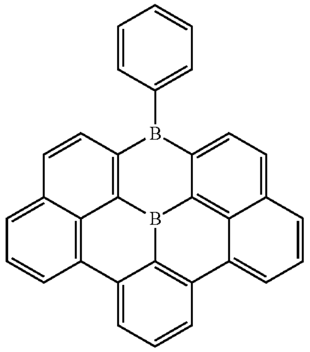
136
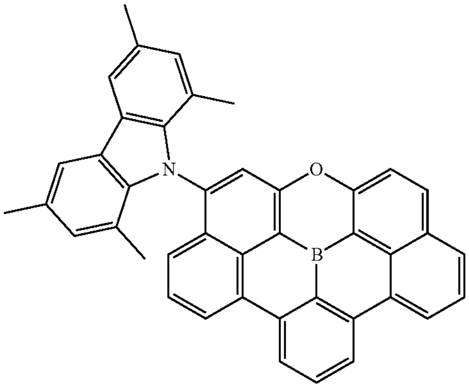 [SMILES: Cc1cc(C)c2c(c1)c1cc(C)cc(C)c1n2-c1cc2c3c4c(cccc14)-c1cccc4c1B3c1c(ccc3cccc-4c13)O2]
137
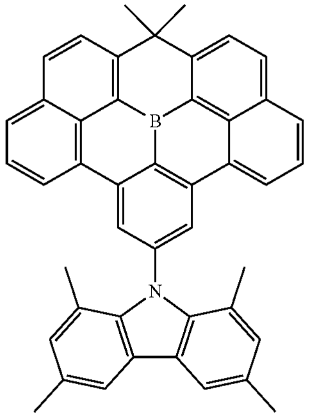 [SMILES: Cc1cc(C)c2c(c1)c1cc(C)cc(C)c1n2-c1cc2c3c(c1)-c1cccc4ccc5c(c14)B3c1c(ccc3cccc-2c13)C5(C)C]

-continued
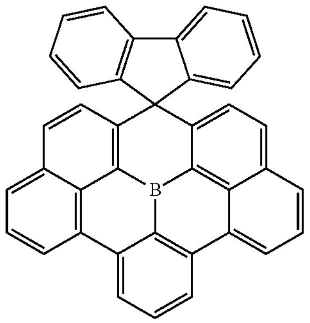
138
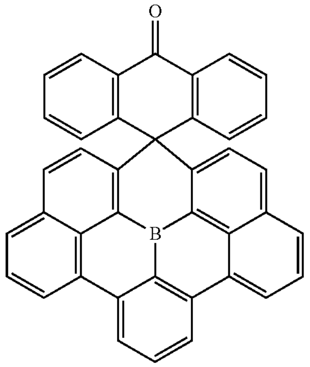 [SMILES: O=C1c2ccccc2C2(c3ccccc31)c1ccc3cccc4c3c1B1c3c-4cccc3-c3cccc4ccc2c1c34]
139
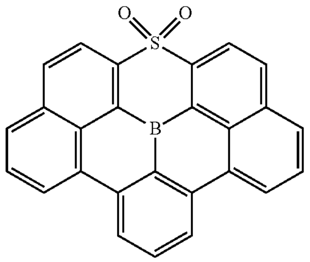
140
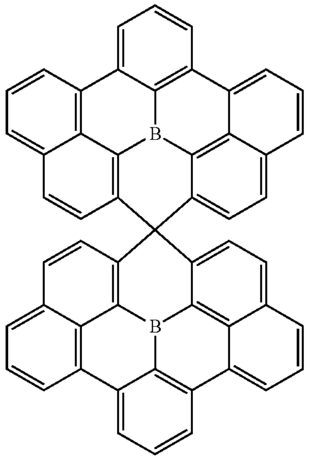
141

-continued
142
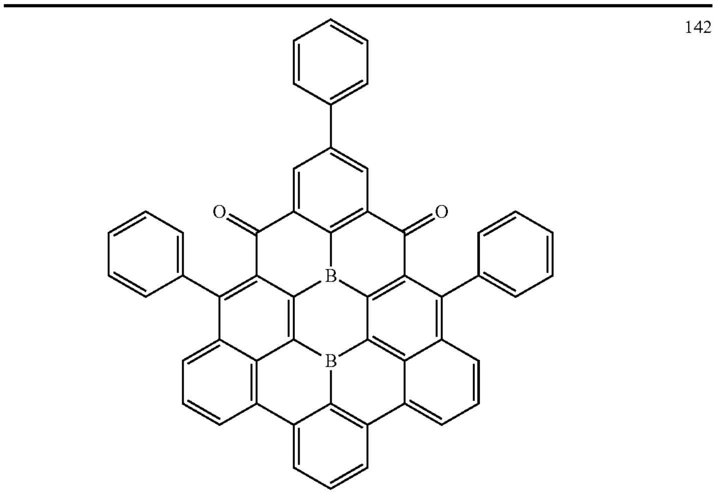
143
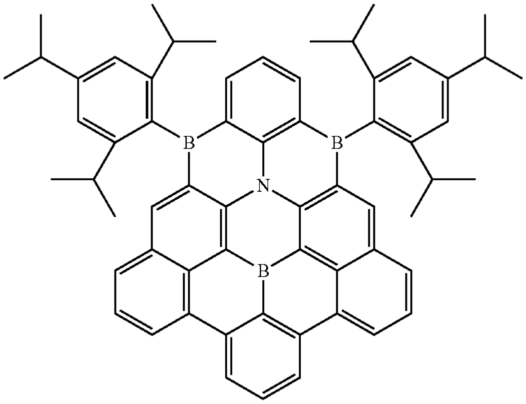 [SMILES: CC(C)c1cc(C(C)C)c(B2c3cccc4c3N3c5c2cc2cccc6c2c5B2c5c-6cccc5-c5cccc6cc(c3c2c56)B4c2c(C(C)C)cc(C(C)C)cc2C(C)C)c(C(C)C)c1]
144
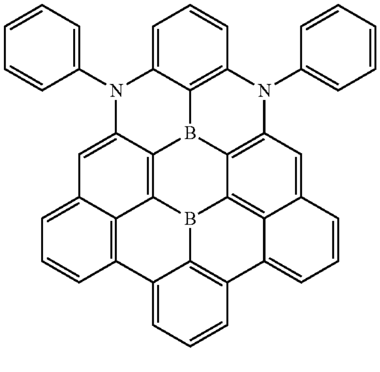

-continued
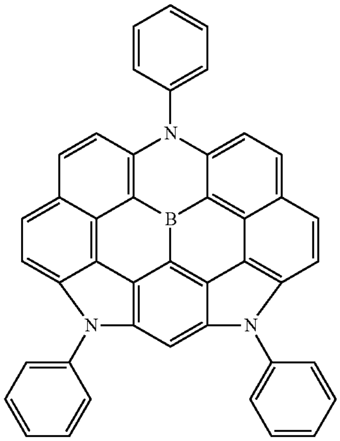 [SMILES: c1ccc(N2c3ccc4ccc5c6c4c3B3c4c2ccc2ccc7c(c42)c2c3c6c(cc2n7-c2ccccc2)n5-c2ccccc2)cc1]
145
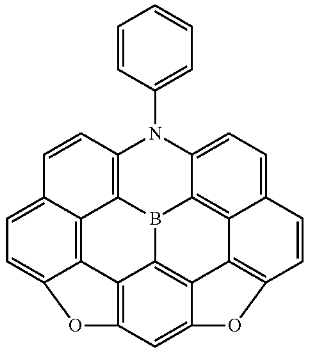 [SMILES: c1ccc(N2c3ccc4ccc5oc6cc7oc8ccc9ccc2c2c9c8c7c7c6c5c4c3B27)cc1]
146
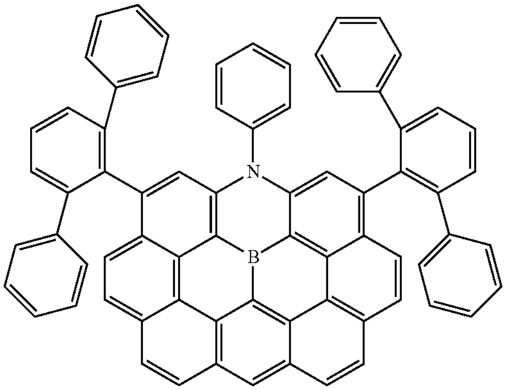 [SMILES: c1ccc(-c2cccc(-c3ccccc3)c2-c2cc3c4c5c2ccc2ccc6cc7ccc8ccc9c(-c%10c(-c%11ccccc%11)cccc%10-c%10ccccc%10)cc(c%10c9c8c7c(c6c25)B4%10)N3c2ccccc2)cc1]
147
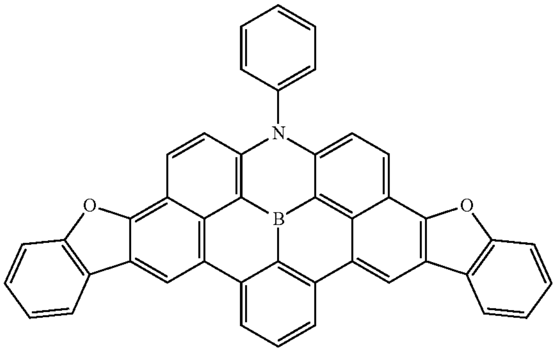 [SMILES: c1ccc(N2c3ccc4c5c(cc6c7ccccc7oc46)-c4cccc6c4B(c35)c3c2ccc2c3c-6cc3c4ccccc4oc23)cc1]
148

-continued
149
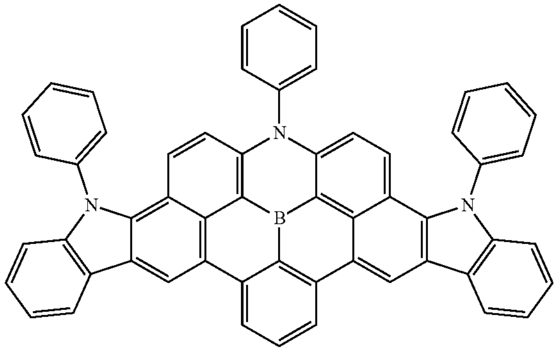 [SMILES: c1ccc(N2c3ccc4c5c(cc6c7ccccc7n(-c7ccccc7)c46)-c4cccc6c4B(c35)c3c2ccc2c3c-6cc3c4ccccc4n(-c4ccccc4)c23)cc1]
150
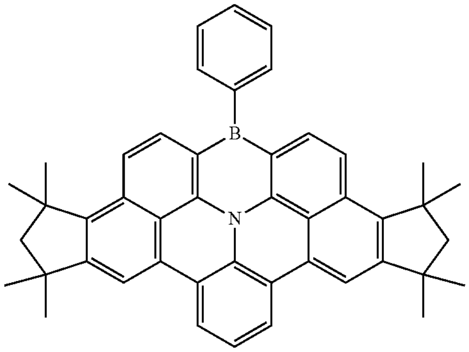
151
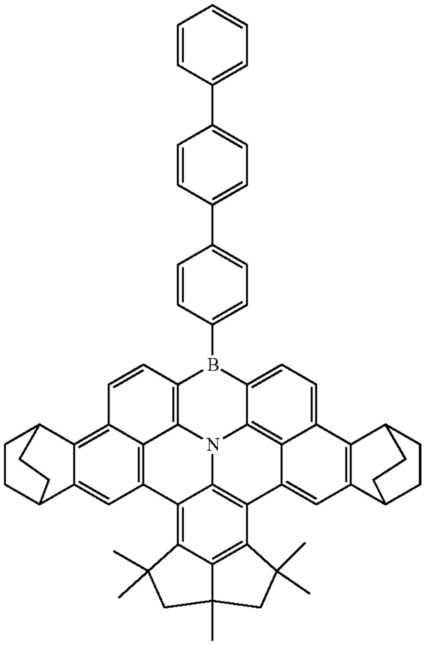 [SMILES: CC1(C)CC2(C)CC(C)(C)c3c4c5c(c1c32)-c1cc2c(c3ccc6c(c13)N5c1c(ccc3c5c(cc-4c13)C1CCC5CC1)B6c1ccc(-c3ccc(-c4ccccc4)cc3)cc1)C1CCC2CC1]

-continued
152
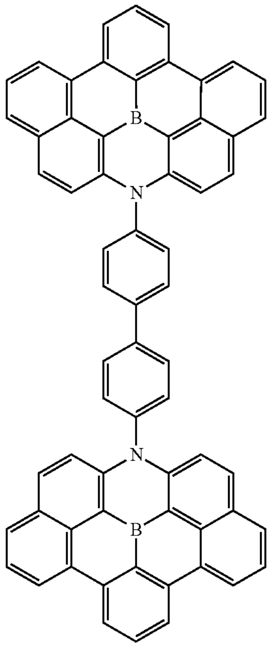 [SMILES: c1cc2c3c(c1)-c1cccc4ccc5c(c14)B3c1c(ccc3cccc-2c13)N5c1ccc(-c2ccc(N3c4ccc5cccc6c5c4B4c5c-6cccc5-c5cccc6ccc3c4c56)cc2)cc1]
153
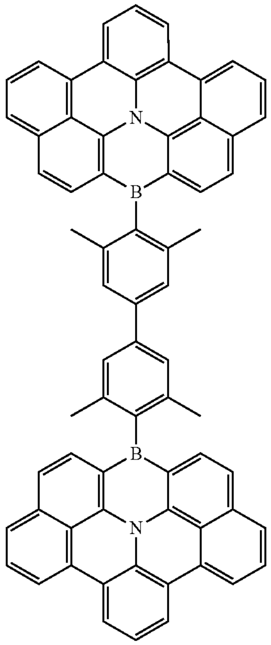 [SMILES: Cc1cc(-c2cc(C)c(B3c4ccc5cccc6c5c4N4c5c-6cccc5-c5cccc6ccc3c4c56)c(C)c2)cc(C)c1B1c2ccc3cccc4c3c2N2c3c-4cccc3-c3cccc4ccc1c2c34]

-continued
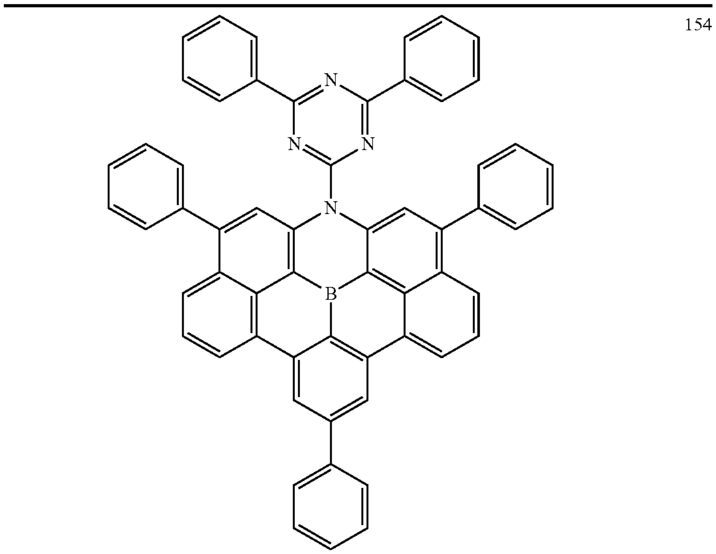
154
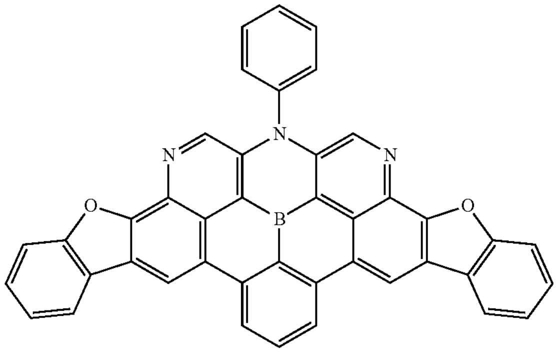 [SMILES: c1ccc(N2c3cnc4c5c(cc6c7ccccc7oc64)-c4cccc6c4B(c35)c3c2cnc2c3c-6cc3c4ccccc4oc32)cc1]
155
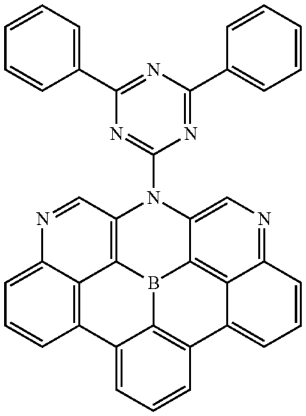 [SMILES: c1ccc(-c2nc(-c3ccccc3)nc(N3c4cnc5cccc6c5c4B4c5c-6cccc5-c5cccc6ncc3c4c56)n2)cc1]
156

-continued
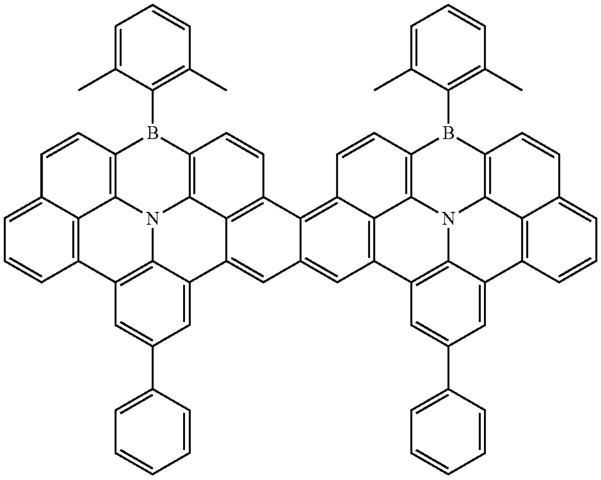 [SMILES: Cc1cccc(C)c1B1c2ccc3cccc4c5cc(-c6ccccc6)cc6c7cc8cc9c%10cc(-c%11ccccc%11)cc%11c%12cccc%13ccc%14c(c%13%12)n(c%12c(ccc(c8c8ccc1c(c78)n(c2c34)c56)c9%12)B%14c1c(C)cccc1C)c%11%10]
157
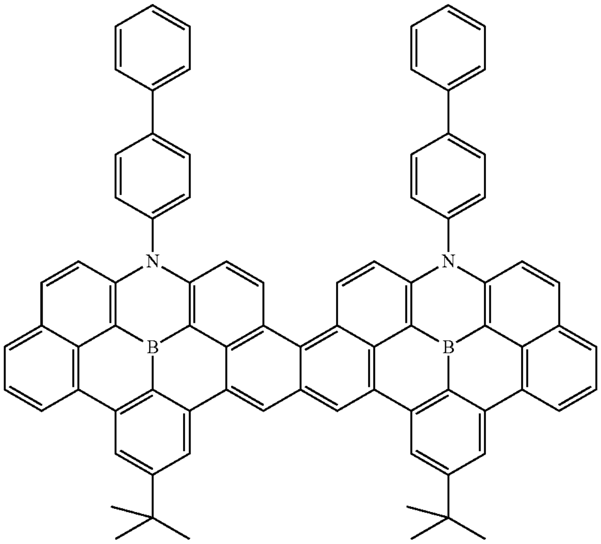 [SMILES: CC(C)(C)c1cc2c3c(c1)-c1cc4cc5c6c7c(ccc6c4c4ccc6c(c14)B3c1c(ccc3cccc-2c13)N6c1ccc(-c2ccccc2)cc1)N(c1ccc(-c2ccccc2)cc1)c1ccc2cccc3c2c1B7c1c-3cc(C(C)(C)C)cc1-5]
158
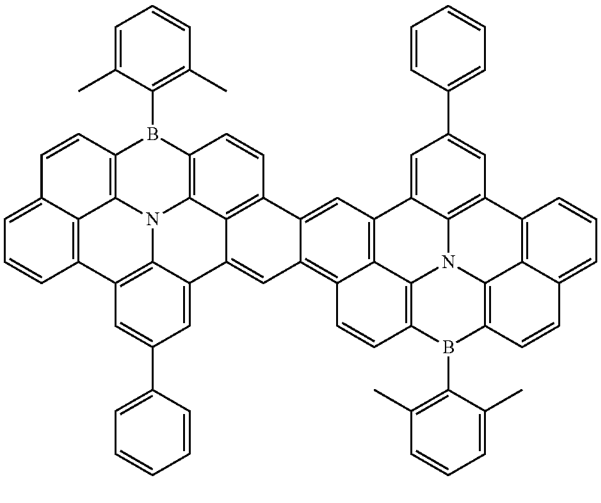 [SMILES: Cc1cccc(C)c1B1c2ccc3cccc4c5cc(-c6ccccc6)cc6c7cc8c(cc9c%10cc(-c%11ccccc%11)cc%11c%12cccc%13ccc%14c(c%13%12)n(c%12c(ccc8c9%12)B%14c8c(C)cccc8C)c%11%10)c8ccc1c(c87)n(c2c34)c56]
159

-continued
160
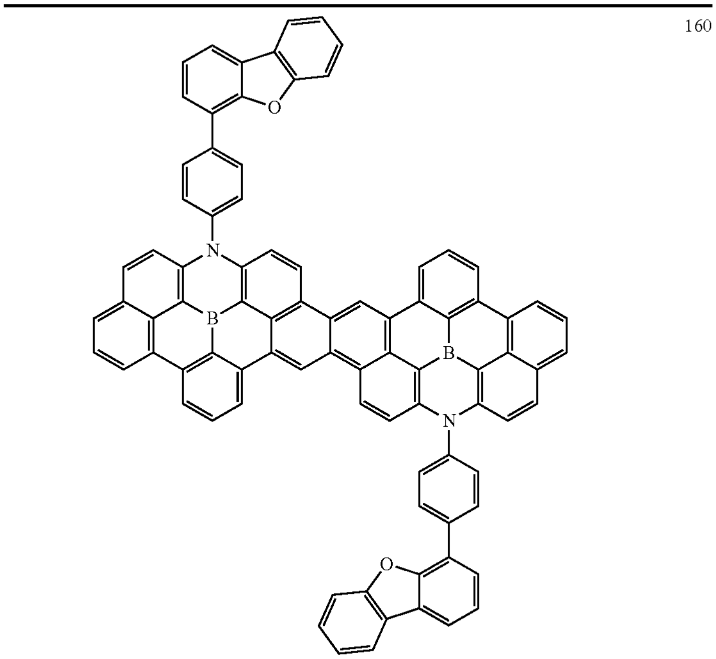
161
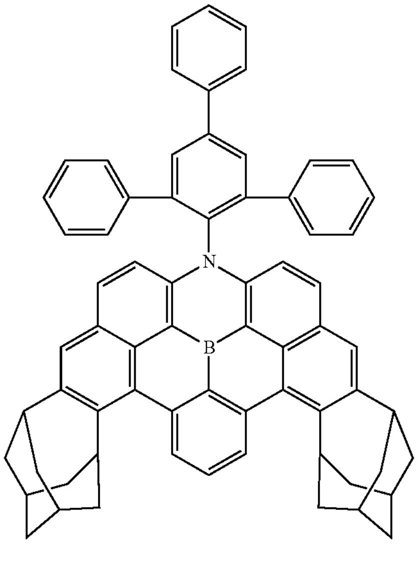 [SMILES: c1ccc(-c2cc(-c3ccccc3)c(N3c4ccc5cc6c(c7c5c4B4c5c-7cccc5-c5c7c(cc8ccc3c4c58)C3CC4CC(C3)CC7C4)C3CC4CC(CC6C4)C3)c(-c3ccccc3)c2)cc1]

-continued
162
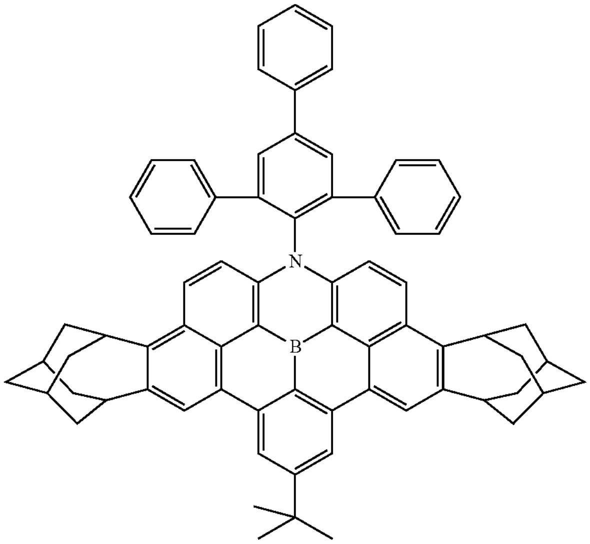 [SMILES: CC(C)(C)c1cc2c3c(c1)-c1cc4c(c5ccc6c(c15)B3c1c(ccc3c5c(cc-2c13)C1CC2CC(C1)CC5C2)N6c1c(-c2ccccc2)cc(-c2ccccc2)cc1-c1ccccc1)C1CC2CC(CC4C2)C1]
163
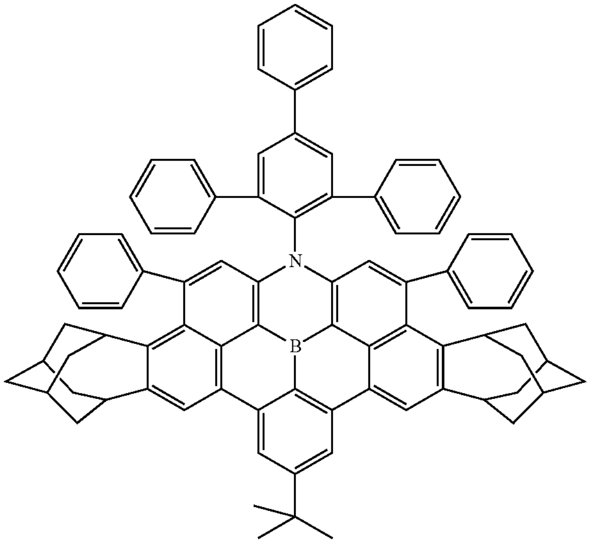 [SMILES: CC(C)(C)c1cc2c3c(c1)-c1cc4c(c5c(-c6ccccc6)cc6c(c15)B3c1c(cc(-c3ccccc3)c3c5c(cc-2c13)C1CC2CC(C1)CC5C2)N6c1c(-c2ccccc2)cc(-c2ccccc2)cc1-c1ccccc1)C1CC2CC(CC4C2)C1]

-continued
164
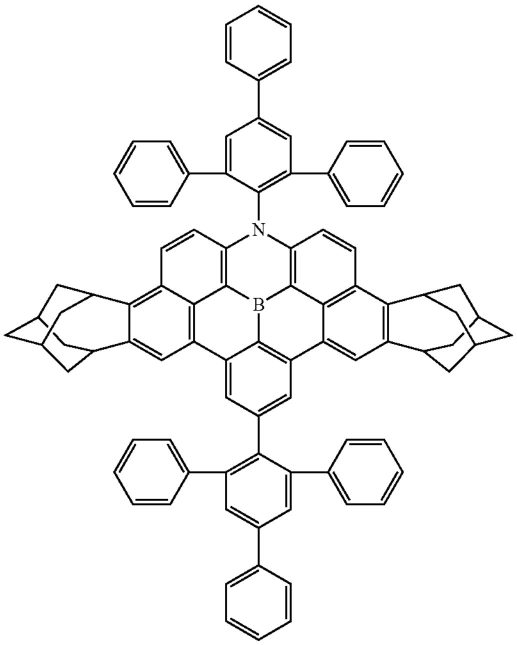 [SMILES: c1ccc(-c2cc(-c3ccccc3)c(-c3cc4c5c(c3)-c3cc6c(c7ccc8c(c37)B5c3c(ccc5c7c(cc-4c35)C3CC4CC(C3)CC7C4)N8c3c(-c4ccccc4)cc(-c4ccccc4)cc3-c3ccccc3)C3CC4CC(CC6C4)C3)c(-c3ccccc3)c2)cc1]
165
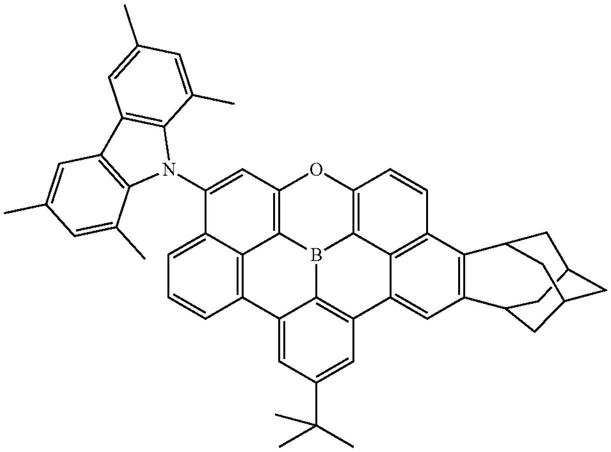 [SMILES: Cc1cc(C)c2c(c1)c1cc(C)cc(C)c1n2-c1cc2c3c4c(cccc14)-c1cc(C(C)(C)C)cc4c1B3c1c(ccc3c5c(cc-4c13)C1CC3CC(C1)CC5C3)O2]
166
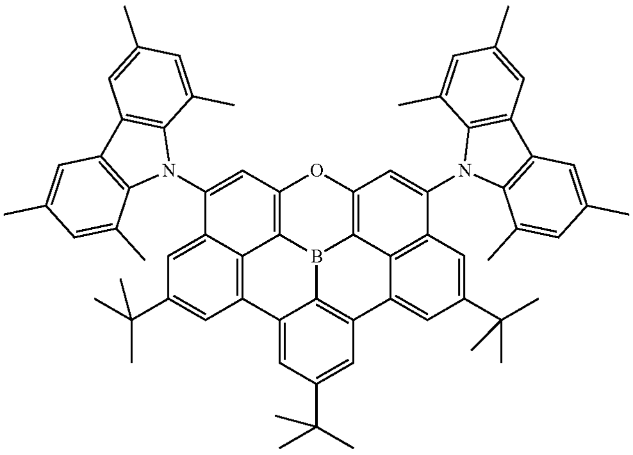

Preferred embodiments of compounds of the invention are recited in detail in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, in which a base skeleton having a $Z^1$ group or a precursor of the $Z^1$ group is synthesized, and then a ring closure reaction is conducted by means of a nucleophilic aromatic substitution reaction or a coupling reaction.

The present invention also further provides a process for preparing the compounds of the invention, in which a base skeleton having a $Z^1$ group or a precursor of the $Z^1$ group is synthesized, and at least one of the $Z^2$, $Y^1$, $Y^2$, $Y^3$ groups is introduced by means of a nucleophilic aromatic substitution reaction or a coupling reaction.

Suitable compounds comprising a base skeleton having a $Z^1$ group are in many cases commercially available, and the starting compounds detailed in the examples are obtainable by known processes, and so reference is made thereto.

These compounds can be reacted with further compounds comprising at least one of the $Z^2$, $Y^1$, $Y^2$, $Y^3$ groups by known coupling reactions, the necessary conditions for this purpose being known to the person skilled in the art, and detailed specifications in the examples assisting the person skilled in the art in conducting these reactions.

Particularly suitable and preferred coupling reactions which all lead to C—C bond formations and/or C—N bond formations are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The principles of the preparation processes detailed above are known in principle from the literature for similar compounds and can be adapted easily by the person skilled in the art for the preparation of the compounds of the invention. Further information can be found in the examples.

It is possible by these methods, if necessary followed by purification, for example recrystallization or sublimation, to obtain the compounds of the invention in high purity, preferably more than 99% (determined by means of $^1H$ NMR and/or HPLC).

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (Ia) and/or (Ib) and preferred embodiments of this formula or compounds of the invention, wherein one or more bonds of the compounds of the invention or of the structures of the formula (Ia) and/or (Ib) and preferred embodiments of that formula to the polymer, oligomer or dendrimer are present. According to the linkage of the structures of the formula (Ia) and/or (Ib) and preferred embodiments of this formula or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (Ia) and/or (Ib) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the formula (Ia) and/or (Ib) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of the invention and at least one further compound. The further compound may, for example, be a solvent, especially one of the abovementioned solvents or a mixture of these solvents. If the further compound comprises a solvent, this mixture is referred to herein as formulation. The further compound may alternatively be at least one further organic or inorganic compound which is likewise used in the electronic device, for example an emitter and/or a matrix material, where these compounds differ from the compounds of the invention. Suitable emitters and matrix materials are listed at the back in connection with the organic electroluminescent device. The further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide bandgap materials and n-dopants.

The present invention further provides for the use of a compound of the invention in an electronic device, especially in an organic electroluminescent device, preferably as emitter, more preferably as green, red or blue emitter. In this case, compounds of the invention preferably exhibit fluorescent properties and thus provide preferentially fluorescent emitters.

The present invention still further provides an electronic device comprising at least one compound of the invention. An electronic device in the context of the present invention is a device comprising at least one layer comprising at least one organic compound. This component may also comprise inorganic materials or else layers formed entirely from inorganic materials.

The electronic device is preferably selected from the group consisting of More preferably, electronic device is selected from the group consisting of organic electroluminescent devices (OLEDs, sOLED, PLEDs, LECs, etc.), preferably organic light-emitting diodes (OLEDs), organic light-emitting diodes based on small molecules (sOLEDs), organic light-emitting diodes based on polymers (PLEDs), light-emitting electrochemical cells (LECs), organic laser diodes (O-laser), organic plasmon-emitting devices (D. M. Koller et al., *Nature Photonics* 2008, 1-4), organic integrated circuits (O—ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs) and organic electrical sensors, preferably organic electroluminescent devices (OLEDs, sOLED, PLEDs, LECs, etc.), more preferably organic light-emitting diodes (OLEDs), organic light-emitting diodes based on small molecules (sOLEDs), organic light-emitting diodes based on polymers (PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem electroluminescent device, especially for white-emitting OLEDs.

The compound of the invention may be used in different layers, according to the exact structure. Preference is given to an organic electroluminescent device comprising a compound of formula (Ia) and/or (Ib) or the above-detailed preferred embodiments in an emitting layer as emitter, preferably red, green or blue emitter.

When the compound of the invention is used as emitter in an emitting layer, preference is given to using a suitable matrix material which is known as such.

A preferred mixture of the compound of the invention and a matrix material contains between 99% and 1% by volume, preferably between 98% and 10% by volume, more preferably between 97% and 60% by volume and especially between 95% and 80% by volume of matrix material, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or biscarbazoles, for example according to JP 3139321 B2. Further-preferred matrix materials or host materials are anthracenes. Particularly preferred anthracenes are disclosed in WO 2014/106523 A1, very particularly those of the formula (II). Further particularly preferred anthracenes are disclosed in WO2007/065547 A1, very particularly those of the formulae (2) and (3) and especially those of the formulae (A1) to (A64). Further particularly preferred anthracenes are disclosed in WO2007/065548 A1, very particularly those of the formula (1) and especially those of the formulae H1 to H20.

In addition, the co-host used may be a compound that does not take part in charge transport to a significant degree, if at all, as described, for example, in WO 2010/108579. Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

In a preferred configuration, a compound of the invention which is used as emitter is preferably used in combination with one or more phosphorescent materials (triplet emitters) and/or a compound which is a TADF (thermally activated delayed fluorescence) host material. Preference is given here to forming a hyperfluorescence and/or hyperphosphorescence system.

WO 2015/091716 A1 and WO 2016/193243 A1 disclose OLEDs containing both a phosphorescent compound and a fluorescent emitter in the emission layer, where the energy is transferred from the phosphorescent compound to the fluorescent emitter (hyperphosphorescence). In this context, the phosphorescent compound accordingly behaves as a host material. As the person skilled in the art knows, host materials have higher singlet and triplet energies as compared to the emitters in order that the energy from the host material can also be transferred to the emitter with maximum efficiency. The systems disclosed in the prior art have exactly such an energy relation.

Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186, WO 2018019687, WO 2018019688, WO 2018041769, WO 2018054798, WO 2018069196, WO 2018069197, WO 2018069273, WO 2018134392, WO 2018178001, WO 2018177981, WO 2019020538, WO 2019115423, WO 2019158453 and WO 2019179909. In general, all phosphorescent complexes as used for phosphorescent electroluminescent devices according to the prior art and as known to those skilled in the art in the field of organic electroluminescence are suitable, and the person skilled in the art will be able to use further phosphorescent complexes without exercising inventive skill.

A compound of the invention may preferably be used in combination with a TADF host material and/or a TADF emitter, as set out above.

The process referred to as thermally activated delayed fluorescence (TADF) is described, for example, by B. H. Uoyama et al., Nature 2012, Vol. 492, 234. In order to enable this process, a comparatively small singlet-triplet separation $\Delta E(S_1-T_1)$ of less than about 2000 $cm^{-1}$, for example, is needed in the emitter. In order to open up the $T_1 \rightarrow S_1$ transition which is spin-forbidden in principle, as well as the emitter, it is possible to provide a further compound in the matrix that has strong spin-orbit coupling, such that intersystem crossing is enabled via the spatial proximity and the interaction which is thus possible between the molecules, or the spin-orbit coupling is generated by means of a metal atom present in the emitter.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (Ia) and/or (Ib) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

Formulations for applying a compound of formula (Ia) and/or (Ib) or the preferred embodiments thereof detailed above are novel. The present invention therefore further provides formulations containing at least one solvent and a compound according to formula (Ia) and/or (Ib) or the preferred embodiments thereof detailed above.

In addition, hybrid methods are possible, in which, for example, one or more layers are applied from solution and one or more further layers are applied by vapor deposition.

Those skilled in the art are generally aware of these methods and are able to apply them without exercising inventive skill to organic electroluminescent devices comprising the compounds of the invention.

The compounds of the invention and the organic electroluminescent devices of the invention have the particular feature of an improved lifetime over the prior art. At the same time, the further electronic properties of the electroluminescent devices, such as efficiency or operating voltage, remain at least equally good. In a further variant, the compounds of the invention and the organic electroluminescent devices of the invention especially feature improved efficiency and/or operating voltage and higher lifetime compared to the prior art.

The electronic devices of the invention, especially organic electroluminescent devices, are notable for one or more of the following surprising advantages over the prior art:

1. Electronic devices, especially organic electroluminescent devices comprising compounds of formula (Ia) and/or (Ib) or the preferred embodiments as emitters that have been recited above and hereinafter have very narrow emission bands having low FWHM (Full Width Half Maximum) values, and lead to particularly pure-color emission, recognizable by the low CIE y values.
2. Electronic devices, especially organic electroluminescent devices, comprising compounds of formula (Ia) and/or (Ib) or the preferred embodiments as emitters that have been recited above and hereinafter, have excellent efficiency. In this context, compounds of the invention having structures of formula (Ia) and/or (Ib) or the preferred embodiments recited above and hereinafter bring about a low operating voltage when used in electronic devices.
3. With compounds of formula (Ia) and/or (Ib) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
4. Compounds of formula (Ia) and/or (Ib) or the preferred embodiments recited above and hereinafter have excellent glass film formation.
5. Compounds of formula (Ia) and/or (Ib) or the preferred embodiments recited above and hereinafter form very good films from solutions and show excellent solubility.

These abovementioned advantages are not accompanied by an inordinately high deterioration in the further electronic properties.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can have multiple enantiomeric, diastereomeric or tautomeric forms, one form is shown in a representative manner.

Synthesis of Synthons S:

Example S1

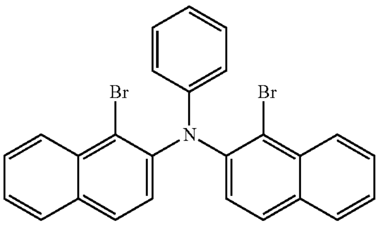 [SMILES: Brc1c(N(c2ccccc2)c2ccc3ccccc3c2Br)ccc2ccccc12]

To a well-stirred mixture of 33.3 g (100 mmol) of 1-bromo-2-iodonaphthalene [90948-03-1], 4.6 g (50 mmol) of aniline [62-53-3], 24.2 g (250 mmol) of sodium tert-butoxide in 600 ml of toluene are added 405 mg (2 mmol) of tri-tert-butylphosphine [131274-22-2] and then 404 mg (1.8 mmol) of palladium(II) acetate, and the mixture is then stirred at 70° C. for 16 h. After cooling, the reaction mixture is washed three times with 500 ml each time of water and once with 500 ml of saturated sodium chloride solution. The organic phase is dried over magnesium sulfate, the magnesium sulfate is filtered therefrom through a silica gel bed in the form of a toluene slurry, and the filtrate is concentrated under reduced pressure to dryness. The residue is subjected to flash chromatography, silica gel, n-heptane/ethyl acetate, Torrent automated column system from A. Semrau. Yield: 14.4 g (28.5 mmol) 57%; purity about 95% by $^{1}$H NMR.

The following compounds can be prepared analogously:

| Ex. | Reactants | Product | Yield |
|---|---|---|---|
| S2 | 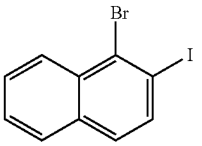<br>90948-03-1<br>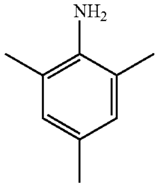<br>88-05-1 | 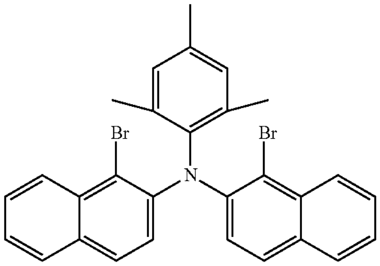 [SMILES: Cc1cc(C)c(N(c2ccc3ccccc3c2Br)c2ccc3ccccc3c2Br)c(C)c1] | 49% |
| S3 | 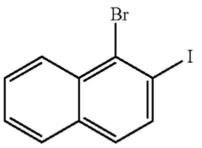<br>90948-03-1<br>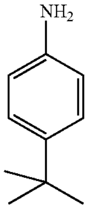<br>769-92-6 | 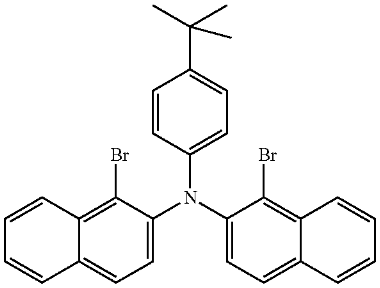 [SMILES: CC(C)(C)c1ccc(N(c2ccc3ccccc3c2Br)c2ccc3ccccc3c2Br)cc1] | 60% |

-continued
| Ex. | Reactants | Product | Yield |
| --- | --- | --- | --- |
| S4 | 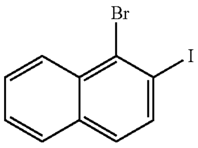<br>90948-03-1<br>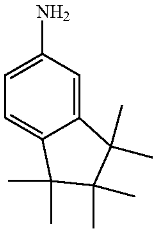<br>2082698-39-1 | 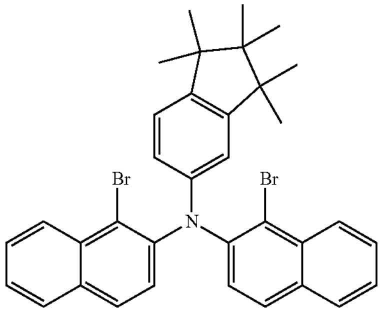 [SMILES: CC1(C)c2ccc(N(c3ccc4ccccc4c3Br)c3ccc4ccccc4c3Br)cc2C(C)(C)C1(C)C] | 57% |
| S5 | 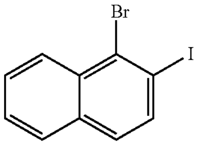<br>90948-03-1<br>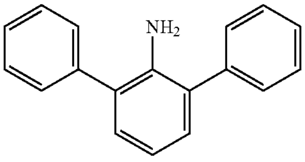<br>87666-57-7 | 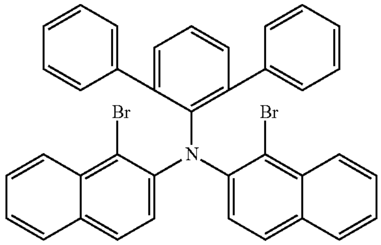 [SMILES: Brc1c(N(c2ccc3ccccc3c2Br)c2c(-c3ccccc3)cccc2-c2ccccc2)ccc2ccccc12] | 41% |
| S6 | 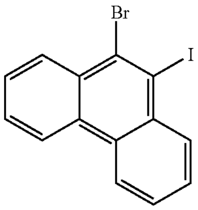<br>93188-73-9<br>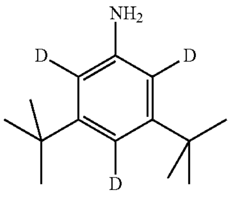<br>18628-47-2 | 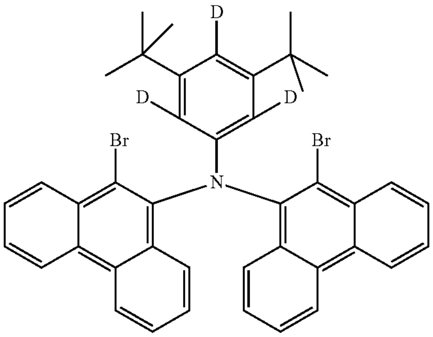 [SMILES: [2H]c1c(N(c2c(Br)c3ccccc3c3ccccc23)c2c(Br)c3ccccc3c3ccccc23)c([2H])c(C(C)(C)C)c([2H])c1C(C)(C)C] | 54% |
| S50 | 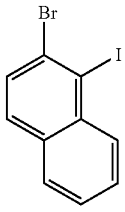<br>676267-05-3 | 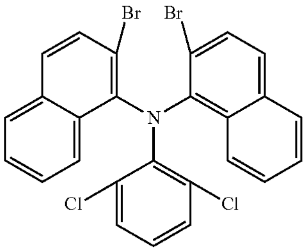 [SMILES: Clc1cccc(Cl)c1N(c1c(Br)ccc2ccccc12)c1c(Br)ccc2ccccc12] | 38% |

-continued
| Ex. | Reactants | Product | Yield |
|---|---|---|---|
| | 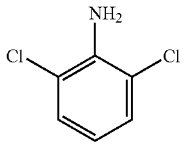 608-31-1 | | |
| S51 | 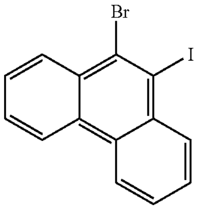 93188-73-9 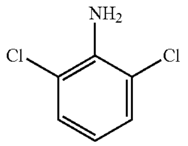 608-31-1 | 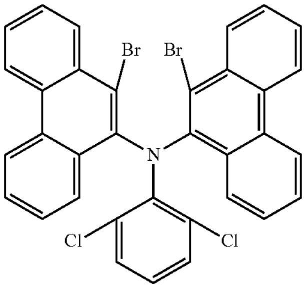 [SMILES: Clc1cccc(Cl)c1N(c1c(Br)c2ccccc2c2ccccc12)c1c(Br)c2ccccc2c2ccccc12] | 33% |
| S52 | 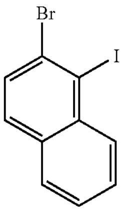 676267-05-3 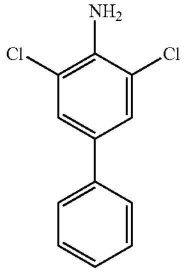 134006-32-9 | 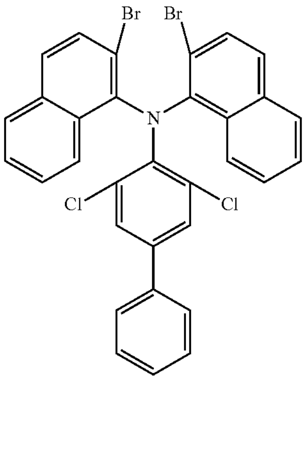 [SMILES: Clc1cc(-c2ccccc2)cc(Cl)c1N(c1c(Br)ccc2ccccc12)c1c(Br)ccc2ccccc12] | 40% |

-continued
| Ex. | Reactants | Product | Yield |
|---|---|---|---|
| S53 | 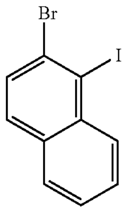<br>676267-05-3<br>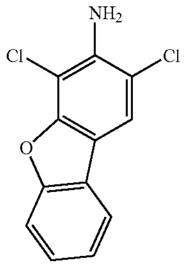<br>132334-54-4 | 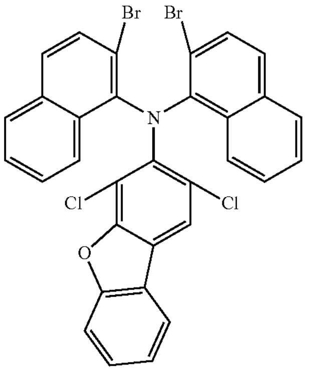 [SMILES: Clc1cc2c(oc3ccccc32)c(Cl)c1N(c1c(Br)ccc2ccccc12)c1c(Br)ccc2ccccc12] | 37% |
| S54 | 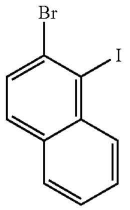<br>676267-05-3<br>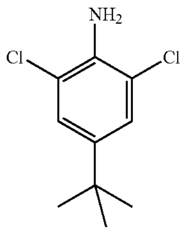<br>85911-37-1 | 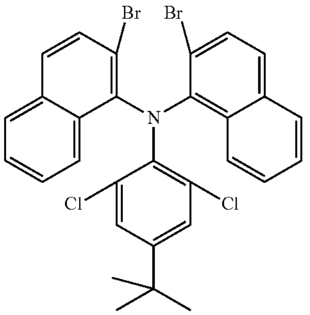 [SMILES: CC(C)(C)c1cc(Cl)c(N(c2c(Br)ccc3ccccc23)c2c(Br)ccc3ccccc23)c(Cl)c1] | 43% |
| S55 | 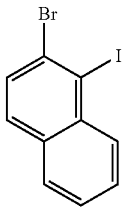<br>676267-05-3<br>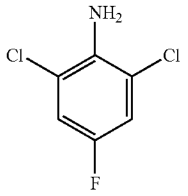<br>344-19-4 | 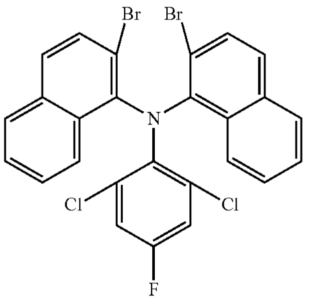 [SMILES: Fc1cc(Cl)c(N(c2c(Br)ccc3ccccc23)c2c(Br)ccc3ccccc23)c(Cl)c1] | 40% |

-continued

| Ex. | Reactants | Product | Yield |
|---|---|---|---|
| S56 | 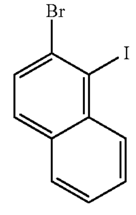<br>676267-05-3<br>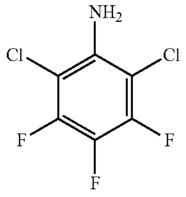<br>512778-61-9 | 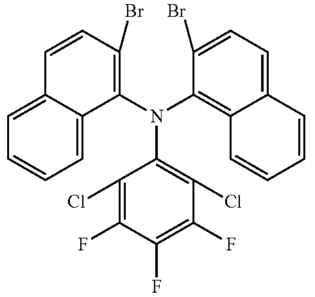 [SMILES: Fc1c(F)c(Cl)c(N(c2c(Br)ccc3ccccc23)c2c(Br)ccc3ccccc23)c(Cl)c1F] | 30% |

Synthesis of the Compounds of the Invention

Example D1

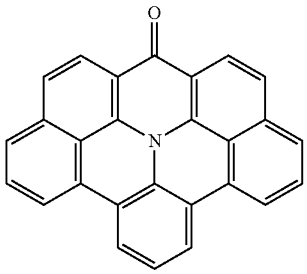 [SMILES: O=c1c2ccc3cccc4c5cccc6c7cccc8ccc1c(c87)n(c56)c2c34]

A well-stirred mixture of 29.5 g (100 mmol) of dibenzo [c,h]acridin-7(14H)-one [50405-28-2], 30.0 g (110 mmol) of 2-iodo-1,3-dichlorobenzene [19230-28-5], 41.5 g (300 mmol) of potassium carbonate, anhydrous, 42.6 g (300 mmol) of sodium sulfate, anhydrous, 21.0 g (330 mmol) of copper powder, 100 g of glass beads (diameter 3 mm) and 300 ml of nitrobenzene is boiled at reflux for 24 h. After cooling, a mixture of 1000 ml of methanol and 500 ml of water is added, the mixture is stirred for a further 1 h, and the solids are filtered off with suction, washed five times with 100 ml each time of methanol and dried under reduced pressure. The residue is taken up in 500 ml of o-dichlorobenzene, boiled under reflux for 30 min, and then filtered with suction while still hot through a Celite bed in the form of a o-dichlorobenzene slurry. The filtrate is concentrated to a volume of about 50 ml at 80° C. under reduced pressure, and 100 ml of ethanol is added while it is still hot, which crystallizes the product. After cooling, the crystals are filtered off with suction, washed three times with 50 ml each time of ethanol and dried under reduced pressure. Purification is effected by repeated hot extraction crystallization with dichloromethane (DCM) (alternative solvents: toluene, benzonitrile, chlorobenzene, dimethylacetamide, etc.) and final fractional sublimation or heat treatment under high vacuum. Yield: 13.3 g (36 mmol), 36%; purity: >99.5% by $^1$H NMR/HPLC.

The following compounds can be prepared analogously:
| Ex. | Reactants | Product | Yield |
|---|---|---|---|
| D2 | 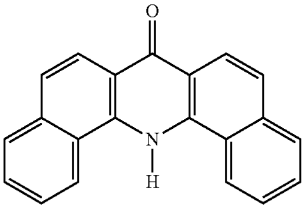<br>50405-28-2<br>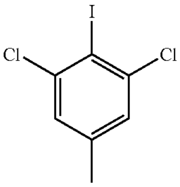<br>939990-12-2 | 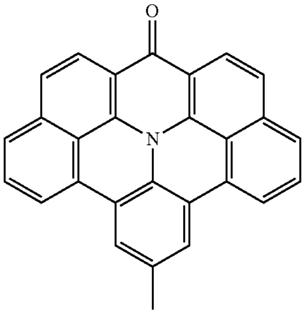 [SMILES: Cc1cc2c3cccc4ccc5c(=O)c6ccc7cccc8c(c1)c2n(c5c43)c6c78] | 33% |
| D3 | 50405-28-2<br>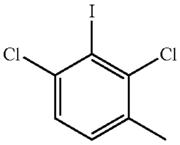<br>206559-56-0 | 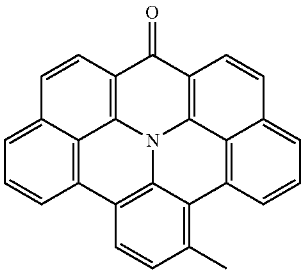 [SMILES: Cc1ccc2c3cccc4ccc5c(=O)c6ccc7cccc8c1c2n(c5c43)c6c78] | 29% |
| D4 | 50405-28-2<br>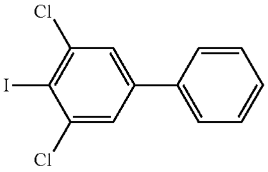<br>1802146-66-2 | 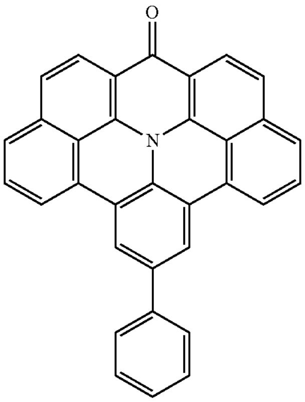 [SMILES: O=c1c2ccc3cccc4c5cc(-c6ccccc6)cc6c7cccc8ccc1c(c87)n(c56)c2c34] | 41% |
| D5 | 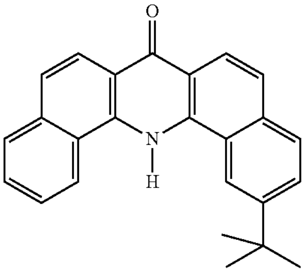<br>213963-12-3<br>1802146-66-2 | 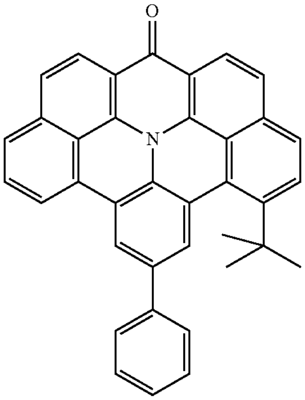 [SMILES: CC(C)(C)c1ccc2ccc3c(=O)c4ccc5cccc6c7cc(-c8ccccc8)cc8c1c2c3n(c78)c4c56] | 23% |

-continued
| Ex. | Reactants | Product | Yield |
|---|---|---|---|
| D6 | 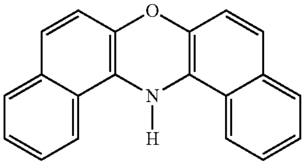<br>224-59-9<br>1802146-66-2 | 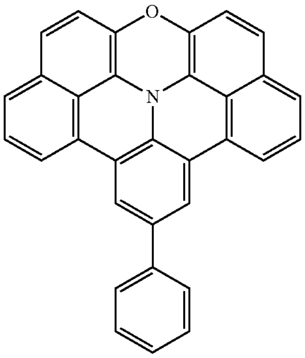 | 56% |
| D7 | 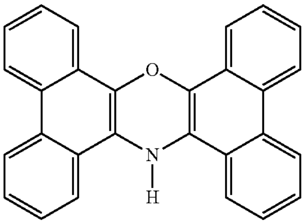<br>215-15-6<br>1802146-66-2 | 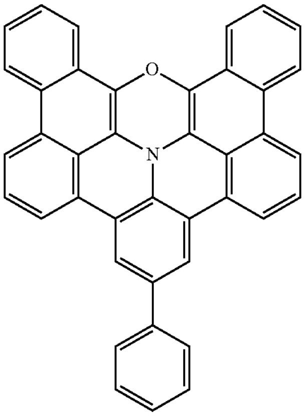 [SMILES: c1ccc(-c2cc3c4cccc5c6ccccc6c6oc7c8ccccc8c8cccc9c(c2)c3n(c6c54)c7c89)cc1] | 53% |
| D8 | 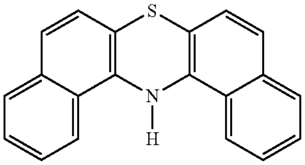<br>224-59-9<br>1802146-66-2 | 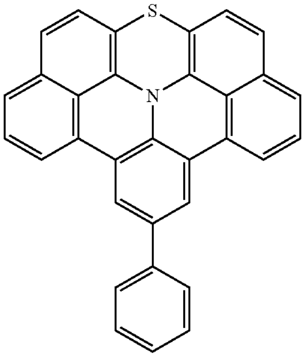 [SMILES: c1ccc(-c2cc3c4cccc5ccc6sc7ccc8cccc9c(c2)c3n(c6c54)c7c89)cc1] | 47% |
| D9 | 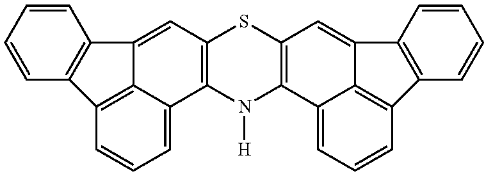<br>43184-05-0<br>1802146-66-2 | 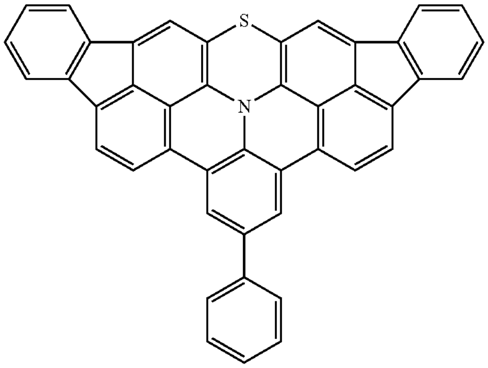 [SMILES: c1ccc(-c2cc3c4ccc5c6ccccc6c6cc7sc8cc9c%10ccccc%10c%10ccc%11c(c2)c3n(c7c4c56)c8c%11c%109)cc1] | 48% |

-continued

| Ex. | Reactants | Product | Yield |
| --- | --- | --- | --- |
| D10 | 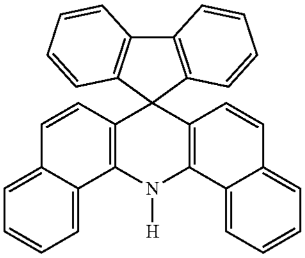 1303969-19-8 1802146-66-2 | 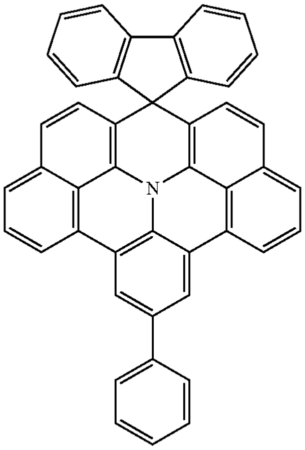 [SMILES: c1ccc(-c2cc3c4c(c2)-c2cccc5ccc6c(c25)N4c2c(ccc4cccc-3c24)C62c3ccccc3-c3ccccc32)cc1] | 40% |
| D11 | 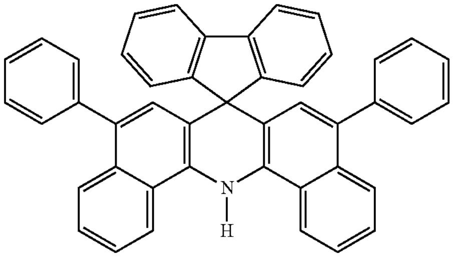 1303969-41-6 1802146-66-2 | 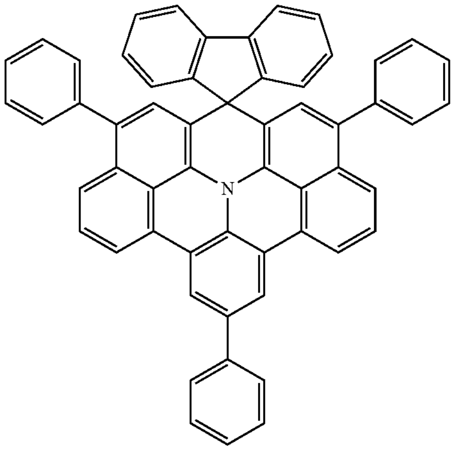 [SMILES: c1ccc(-c2cc3c4c(c2)-c2cccc5c(-c6ccccc6)cc6c(c25)N4c2c(cc(-c4ccccc4)c4cccc-3c24)C62c3ccccc3-c3ccccc32)cc1] | 37% |

Example D50

Steps 1-3 of the sequence that follows are conducted as a one-pot reaction.

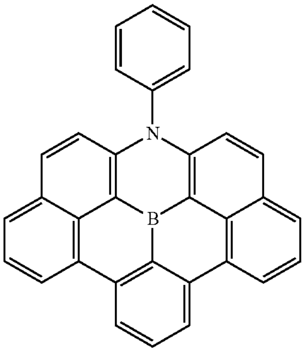 [SMILES: c1ccc(N2c3ccc4cccc5c4c3B3c4c-5cccc4-c4cccc5ccc2c3c45)cc1]

Step 1: Lithiation of S1

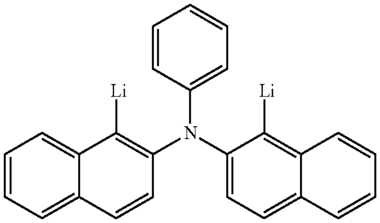

Intermediate, not Isolated

A baked-out, argon-inertized four-neck flask with magnetic stirrer bar, dropping funnel, water separator, reflux condenser and argon blanketing is charged with 28.0 g (50 mmol) of S1 in 1500 ml of tert-butylbenzene. The reaction mixture is cooled down to −45° C., and then 110.5 ml (210 mmol) of tert-butyllithium, 1.9 M in n-pentane, is added dropwise for 30 min. The mixture is stirred at −40° C. for a further 30 min, allowed to warm up to room temperature, then heated 70° C., in the course of which the n-pentane is distilled off via the water separator over about 1 h.

Step 2: Transmetalation and Cyclization

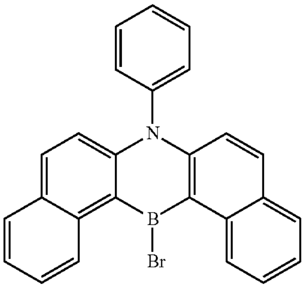 [SMILES: BrB1c2c(ccc3ccccc23)N(c2ccccc2)c2ccc3ccccc3c21]

Intermediate, not Isolated

The reaction mixture is cooled back down to −40° C. 5.2 ml (55 mmol) of boron tribromide is added dropwise over a period of about 10 min. On completion of addition, the reaction mixture is stirred at RT for 1 h and then cooled back down to −40° C.

Step 3: Arylation

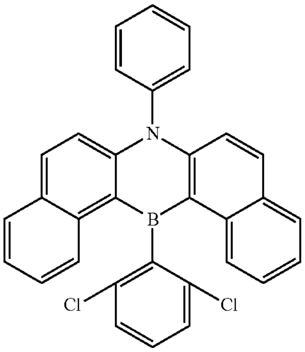 [SMILES: Clc1cccc(Cl)c1B1c2c(ccc3ccccc23)N(c2ccccc2)c2ccc3ccccc3c21]

Intermediate, not Isolated

A second baked-out, argon-inertized Schlenk flask with magnetic stirrer bar is charged with 8.8 g (60 mmol) of 1,3-dichlorobenzene [541-73-1] in 300 ml of THF and cooled down to −78° C. Then 24.0 ml (60 mmol) of n-butyllithium, 2.5 M in n-hexane, is added dropwise thereto for about 20 min; the mixture is then stirred for a further 1.5 h. The reaction mixture is allowed to warm up to RT and stirred for a further 1 h, and the solvent is removed completely under reduced pressure. The lithium organyl is suspended in 300 ml of toluene and transferred into the cold reaction mixture from step 2. The mixture is stirred for a further 1 h, and the reaction mixture is left to warm up to RT overnight. 50 ml of methanol is added cautiously to the reaction mixture, and then the solvent is removed completely under reduced pressure.

Step 4: Cyclization

The solids from step 3 are taken up in 300 ml of dimethylacetamide (DMAC), 27.6 g (200 mmol) of potassium carbonate, 50 g of glass beads (diameter 3 mm) and 1.72 g (3 mmol) of (NHC)Pd(Allyl)Cl[478980-03-9] are added, and the well-stirred reaction mixture is heated to 130° C. for 18 h. The still-hot reaction mixture is filtered through a Celite bed in the form of a hot DMAC slurry, the filtrate is largely concentrated under reduced pressure, 300 ml of hot ethanol is added, and the mixture is stirred for a further 1 h. The product is filtered off with suction while the mixture is still hot, washed three times with 50 ml each time of ethanol and dried under reduced pressure. Purification is effected by repeated hot extraction crystallization with dichloromethane (DCM) (alternative solvents: toluene, benzonitrile, chlorobenzene, dimethylacetamide, etc.) and final fractional sublimation or heat treatment under high vacuum. Yield: 9.4 g (22 mmol), 44%; purity: >99.5% by $^{1}H$ NMR/HPLC.

The following compounds can be prepared analogously:

| Ex. | Reactants | Product | Yield |
|---|---|---|---|
| D51 | 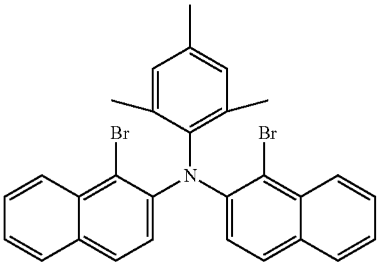 S2 | 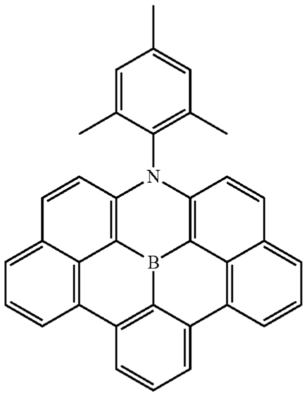 [SMILES: Cc1cc(C)c(N2c3ccc4cccc5c4c3B3c4c-5cccc4-c4cccc5ccc2c3c45)c(C)c1] | 23% |

-continued
| Ex. | Reactants | Product | Yield |
|---|---|---|---|
| D52 | 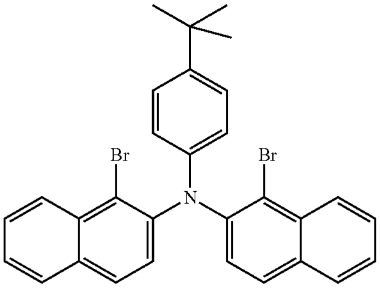 S3 | 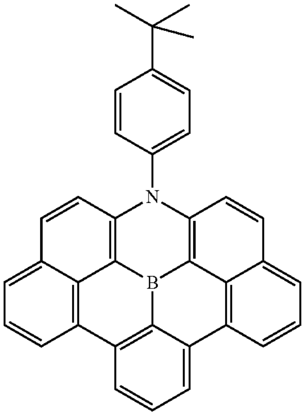 [SMILES: CC(C)(C)c1ccc(N2c3ccc4cccc5c4c3B3c4c-5cccc4-c4cccc5ccc2c3c45)cc1] | 39% |
| D53 | 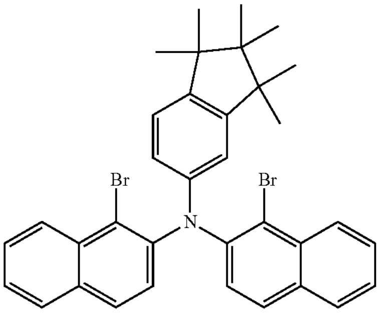 S4 | 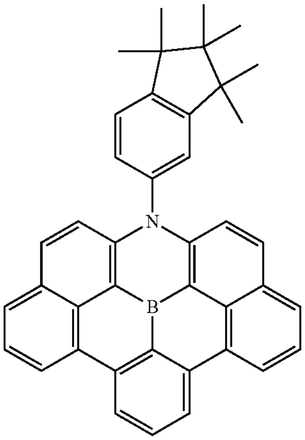 [SMILES: CC1(C)c2ccc(N3c4ccc5cccc6c5c4B4c5c-6cccc5-c5cccc6ccc3c4c56)cc2C(C)(C)C1(C)C] | 35% |
| D54 | 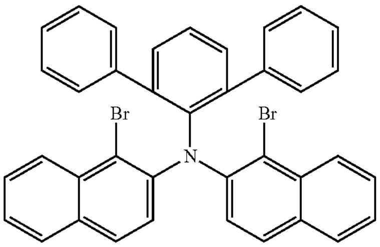 S5 | 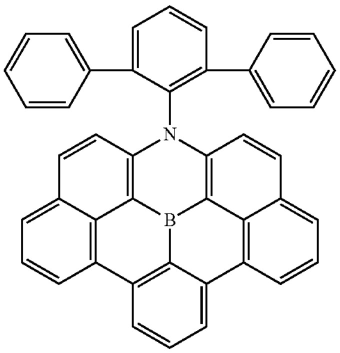 [SMILES: c1ccc(-c2cccc(-c3ccccc3)c2N2c3ccc4cccc5c4c3B3c4c-5cccc4-c4cccc5ccc2c3c45)cc1] | 19% |

-continued
| Ex. | Reactants | Product | Yield |
| --- | --- | --- | --- |
| D55 | 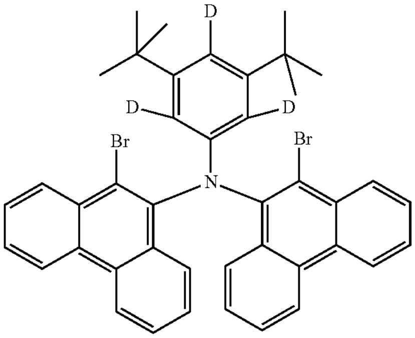 S6 | 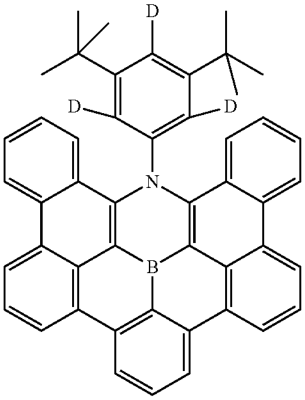 [SMILES: [2H]c1c(N2c3c4c5c(cccc5c5ccccc35)-c3cccc5c3B4c3c2c2ccccc2c2cccc-5c32)c([2H])c(C(C)(C)C)c([2H])c1C(C)(C)C] | 19% |
| D56 | 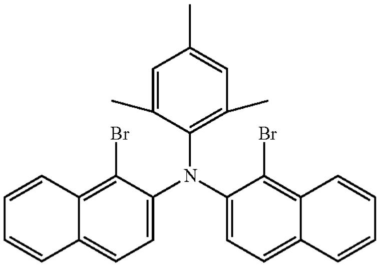 S2 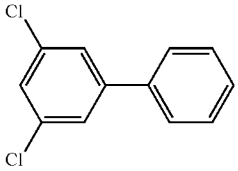 34883-41-5 | 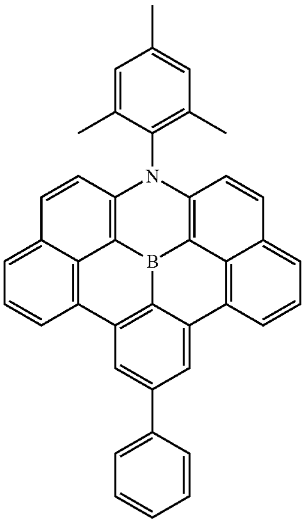 [SMILES: Cc1cc(C)c(N2c3ccc4cccc5c4c3B3c4c-5cc(-c5ccccc5)cc4-c4cccc5ccc2c3c45)c(C)c1] | |
| D57 | 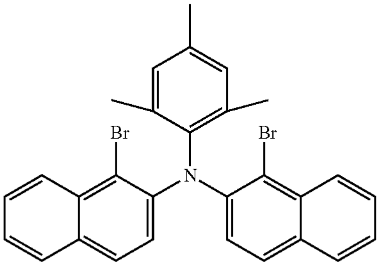 S2 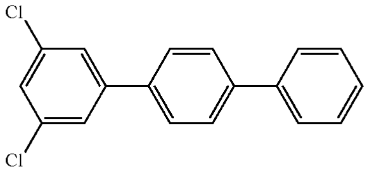 61576-85-0 | 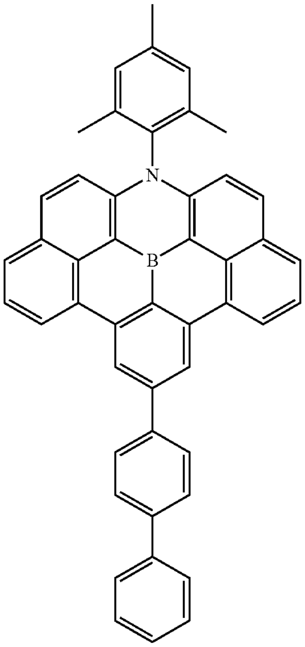 [SMILES: Cc1cc(C)c(N2c3ccc4cccc5c4c3B3c4c-5cc(-c5ccc(-c6ccccc6)cc5)cc4-c4cccc5ccc2c3c45)c(C)c1] | 44% |

-continued
| Ex. | Reactants | Product | Yield |
| --- | --- | --- | --- |
| D58 | 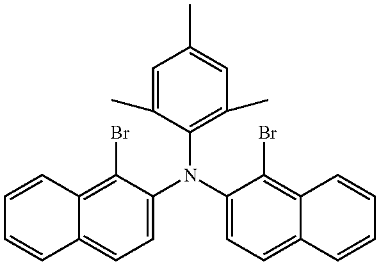<br>S2<br>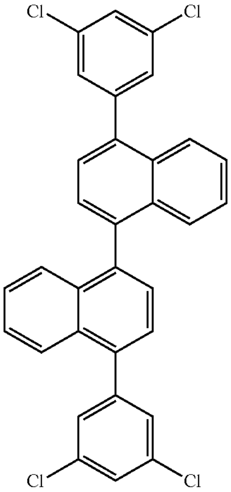<br>951660-91-6<br>25 mmol | 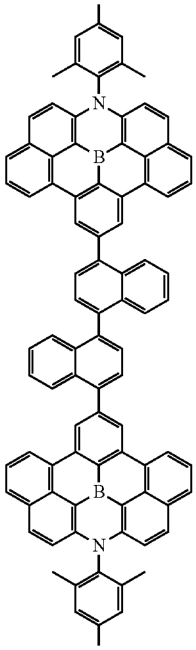 [SMILES: Cc1cc(C)c(N2c3ccc4cccc5c4c3B3c4c-5cc(-c5ccc(-c6ccc(-c7cc8c9c(c7)-c7cccc%10ccc%11c(c7%10)B9c7c(ccc9cccc-8c79)N%11c7c(C)cc(C)cc7C)c7ccccc67)c6ccccc56)cc4-c4cccc5ccc2c3c45)c(C)c1] | 21% |
| D59 | 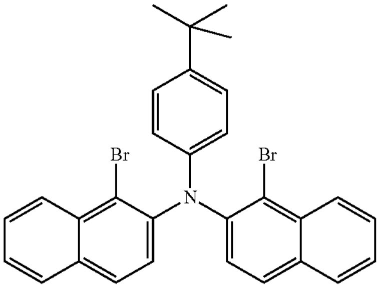<br>S3<br>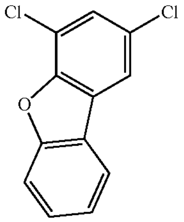<br>24478-74-8 | 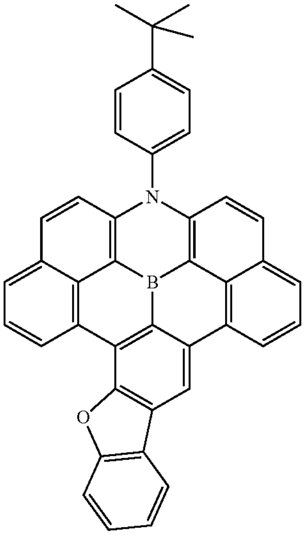 [SMILES: CC(C)(C)c1ccc(N2c3ccc4cccc5c4c3B3c4c-5cc5c(oc6ccccc65)c4-c4cccc5ccc2c3c45)cc1] | 37% |

-continued
| Ex. | Reactants | Product | Yield |
|---|---|---|---|
| D60 | 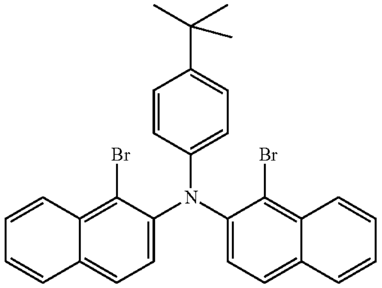 S3 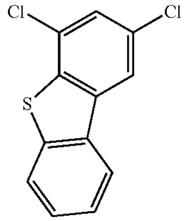 230308-31-3 | 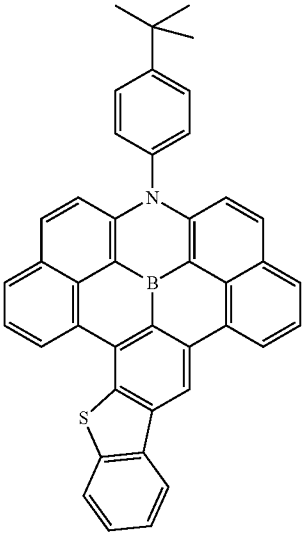 [SMILES: CC(C)(C)c1ccc(N2c3ccc4cccc5c4c3B3c4c-5cc5c(sc6ccccc65)c4-c4cccc5ccc2c3c45)cc1] | 39% |
| D61 | 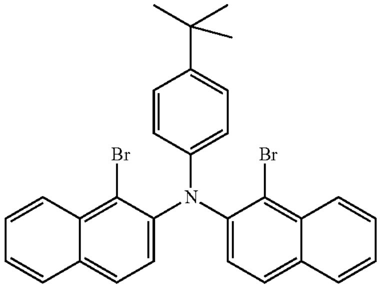 S3 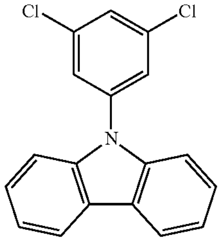 185112-53-2 | 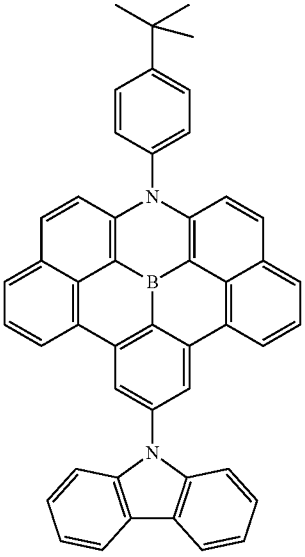 [SMILES: CC(C)(C)c1ccc(N2c3ccc4cccc5c4c3B3c4c-5cc(-n5c6ccccc6c6ccccc65)cc4-c4cccc5ccc2c3c45)cc1] | 40% |

-continued
| Ex. | Reactants | Product | Yield |
|---|---|---|---|
| D62 | 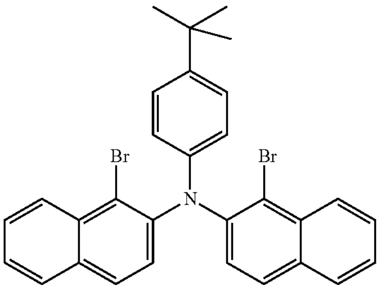 S3 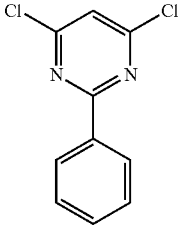 3740-92-9 | 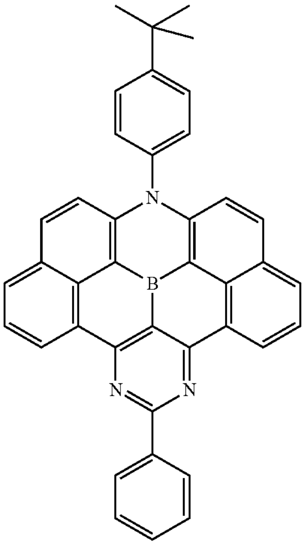 [SMILES: CC(C)(C)c1ccc(N2c3ccc4cccc5c4c3B3c4c-5nc(-c5ccccc5)nc4-c4cccc5ccc2c3c45)cc1] | 11% |
| D63 | 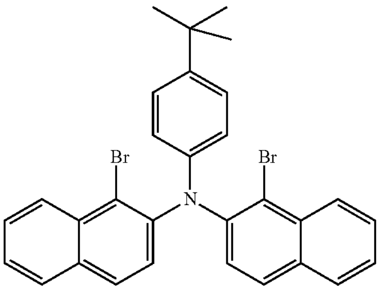 S3 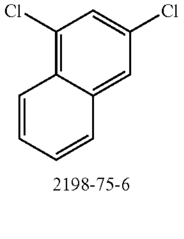 [SMILES: Clc1cc(Cl)c2ccccc2c1] 2198-75-6 | 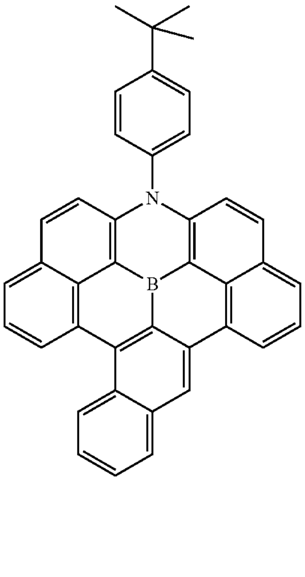 [SMILES: CC(C)(C)c1ccc(N2c3ccc4cccc5c4c3B3c4c-5cc5ccccc5c4-c4cccc5ccc2c3c45)cc1] | 27% |

-continued
| Ex. | Reactants | Product | Yield |
|---|---|---|---|
| D64 | 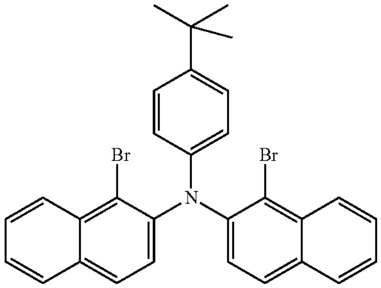 S3 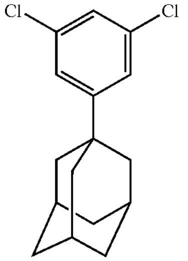 172944-85-3 | 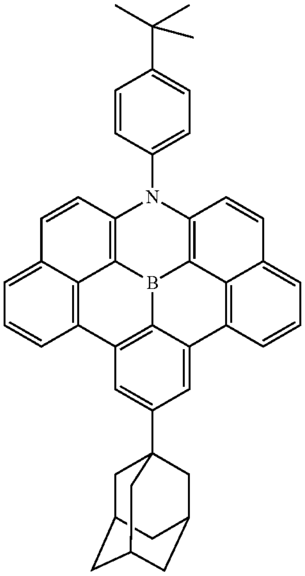 [SMILES: CC(C)(C)c1ccc(N2c3ccc4cccc5c4c3B3c4c-5cc(C56CC7CC(CC(C7)C5)C6)cc4-c4cccc5ccc2c3c45)cc1] | 35% |
| D100 | 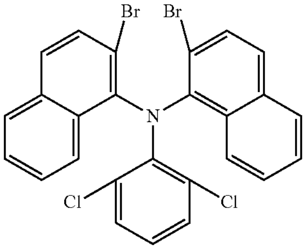 S50 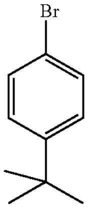 3972-65-4 | 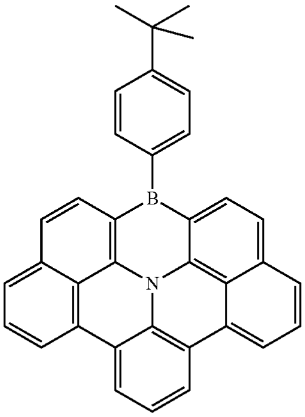 [SMILES: CC(C)(C)c1ccc(B2c3ccc4cccc5c4c3N3c4c-5cccc4-c4cccc5ccc2c3c45)cc1] | 31% |

-continued
| Ex. | Reactants | Product | Yield |
|---|---|---|---|
| D101 | 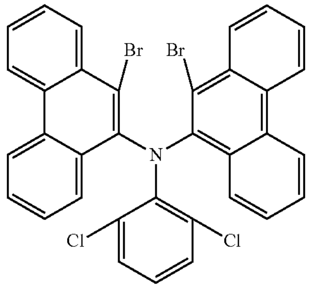<br>S51<br>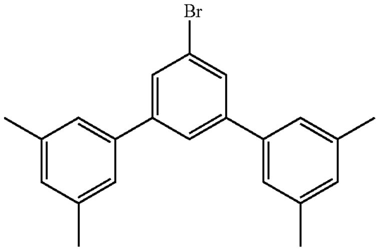<br>278600-38-7 | 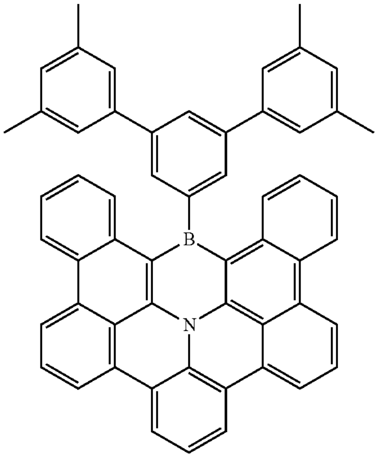 | 18% |
| D102 | 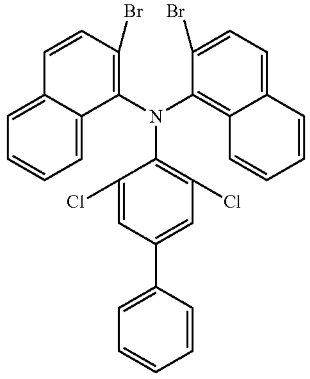<br>S52<br>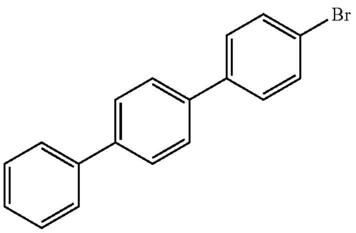<br>1762-84-1 | 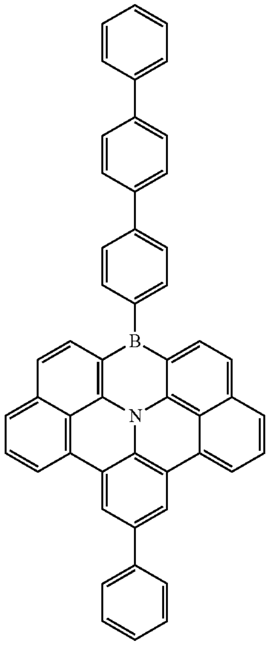 [SMILES: c1ccc(-c2ccc(-c3ccc(B4c5ccc6cccc7c6c5N5c6c-7cc(-c7ccccc7)cc6-c6cccc7ccc4c5c67)cc3)cc2)cc1] | 34% |

-continued
| Ex. | Reactants | Product | Yield |
| --- | --- | --- | --- |
| D103 | 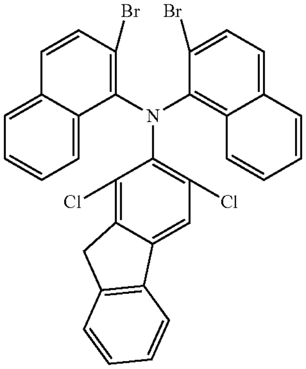<br>S53<br>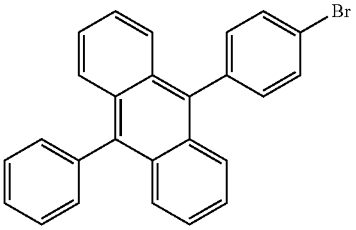<br>625854-02-6 | 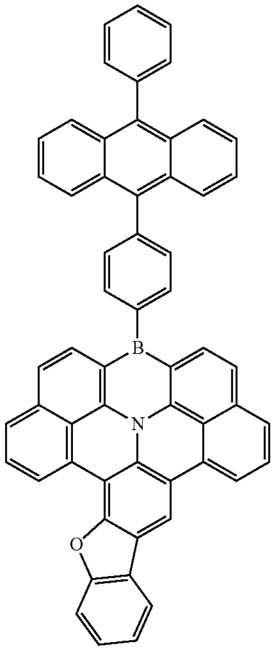 [SMILES: c1ccc(-c2c3ccccc3c(-c3ccc(B4c5ccc6cccc7c6c5N5c6c-7cc7c(oc8ccccc87)c6-c6cccc7ccc4c5c67)cc3)c3ccccc23)cc1] | 28% |
| D104 | 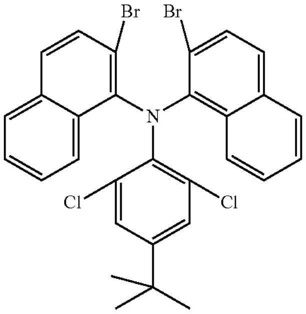<br>S54<br>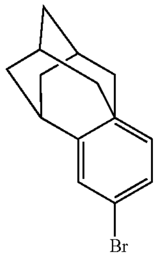<br>1801624-97-4 | 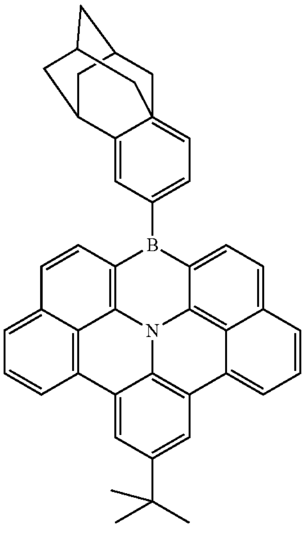 | 37% |

-continued

| Ex. | Reactants | Product | Yield |
|---|---|---|---|
| D105 | 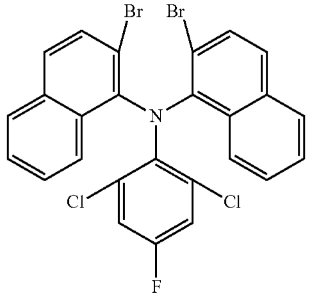 S55 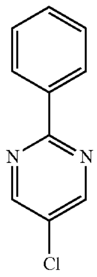 34771-50-1 | 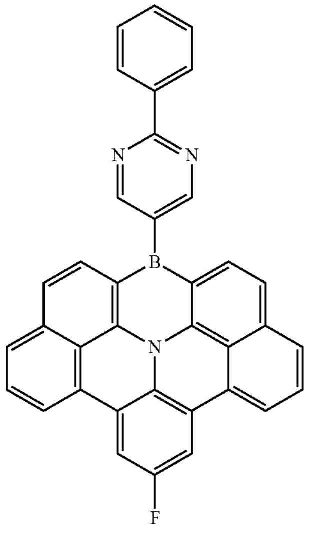 [SMILES: Fc1cc2c3c(c1)-c1cccc4ccc5c(c14)N3c1c(ccc3cccc-2c13)B5c1cnc(-c2ccccc2)nc1] | 25% |
| D106 | 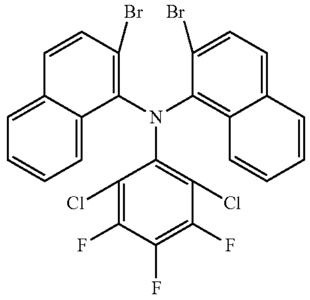 S56 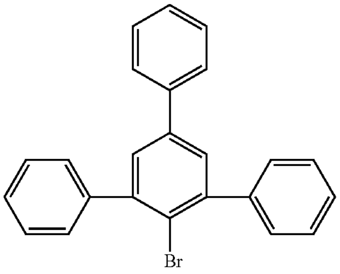 10368-73-7 | 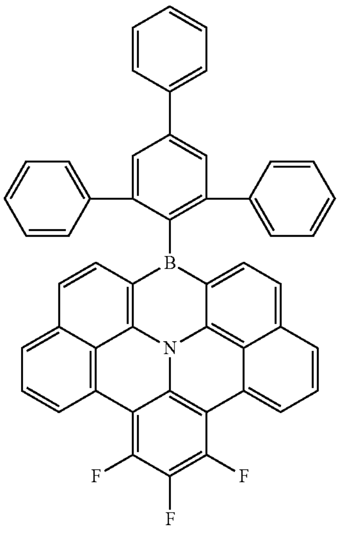 [SMILES: Fc1c(F)c2c3c(c1F)-c1cccc4ccc5c(c14)N3c1c(ccc3cccc-2c13)B5c1c(-c2ccccc2)cc(-c2ccccc2)cc1-c1ccccc1] | 19% |

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plates (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly(styrenesulfonate), purchased as CLEVIOS™ P VP Al 4083 from Heraeus Precious Metals GmbH Deutschland, spun on from aqueous solution) and then baked at 180° C. for 10 min. These coated glass plates form the substrates to which the OLEDs are applied.

The OLEDs basically have the following layer structure: substrate/hole injection layer 1 (HIL1) consisting of Ref-HTM1 doped with 5% NDP-9 (commercially available from Novaled), 20 nm/hole transport layer 1 (HTL1) composed of 160 nm of HTM1/optional hole transport layer 2 (HTL2) 10 nm/emission layer (EML) 20 nm/hole blocker layer (HBL) 10 nm/electron transport layer (ETL) 20 nm/electron injection layer (EIL) composed of 1 nm of ETM2/and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as SMB1: D1 (95:5%) mean here that the material SMB1 is present in the layer in a proportion by volume of 95% and D1 in a proportion of 5%. Analogously, the electron transport layer may also consist of a mixture of two materials. The exact structure of the OLEDs can be found in table 1. The materials used for production of the OLEDs are shown in table 3.

The OLEDs are characterized in a standard manner. For this purpose, the electroluminescence spectra, the current efficiency (measured in cd/A), the power efficiency (measured in Im/VV) and the external quantum efficiency (EQE, measured in percent) are, as a function of luminance, calculated from current-voltage-luminance characteristics (IUL characteristics) assuming Lambertian radiation characteristics. Electroluminescence spectra are determined at a luminance of 1000 $cd/m^2$, and these are used to calculate the CIE 1931 y color coordinates.

Use of compounds of the invention as materials in OLEDs One use of the compounds of the invention is as hole transport material and dopant in the emission layer in OLEDs. The compounds D-Ref.1 according to table 3 are used as a comparison according to the prior art. The results for the OLEDs are collated in table 2.

TABLE 1

Structure of the OLEDs

| Ex. | HTL2 | EML | HBL | ETL |
|---|---|---|---|---|
| Ref. 1 | — | SMB1:D-Ref. 1 (95%:5%) | ETM1 | ETM1:ETM2 (50%:50%) |
| DD5 | D11 | SMB1:D5 (95%:5%) | ETM1 | ETM1:ETM2 (50%:50%) |
| DD50 | — | SMB1:D50 (95%:5%) | ETM1 | ETM1:ETM2 (50%:50%) |
| DD51 | — | SMB1:D51 (95%:5%) | ETM1 | ETM1:ETM2 (50%:50%) |
| DD52 | — | SMB2:D52 (95%:5%) | ETM1 | ETM1:ETM2 (50%:50%) |
| DD54 | D6 | SMB1:D54 (95%:5%) | ETM1 | ETM1:ETM2 (50%:50%) |
| DD55 | — | SMB1:D55 (95%:5%) | ETM1 | ETM1:ETM2 (50%:50%) |
| DD57 | D8 | SMB1:D57 (95%:5%) | ETM1 | ETM1:ETM2 (50%:50%) |
| DD59 | — | SMB1:D59 (95%:5%) | ETM1 | ETM1:ETM2 (50%:50%) |
| DD60 | — | SMB3:D60 (95%:5%) | ETM1 | ETM1:ETM2 (50%:50%) |
| DD61 | — | SMB1:D61 (95%:5%) | ETM1 | ETM1:ETM2 (50%:50%) |
| DD62 | — | SMB1:D62 (95%:5%) | ETM1 | ETM1:ETM2 (50%:50%) |
| DD63 | — | SMB1:D63 (95%:5%) | ETM1 | ETM1:ETM2 (50%:50%) |
| DD100 | — | SMB1:D100 (95%:5%) | ETM1 | ETM1:ETM2 (50%:50%) |
| DD101 | — | SMB1:D101 (95%:5%) | ETM1 | ETM1:ETM2 (50%:50%) |

TABLE 1-continued

Structure of the OLEDs

| Ex. | HTL2 | EML | HBL | ETL |
|---|---|---|---|---|
| DD102 | — | SMB1:D102 (95%:5%) | ETM1 | ETM1:ETM2 (50%:50%) |
| DD105 | D10 | SMB1:D105 (95%:5%) | ETM1 | ETM1:ETM2 (50%:50%) |

TABLE 2

Results for the vacuum-processed OLEDs

| Ex. | EQE (%) 1000 $cd/m^2$ | Voltage (V) 1000 $cd/m^2$ | Lmax. [nm] | EL-FWHM [nm] |
|---|---|---|---|---|
| Ref. 1 | 2.9 | 5.6 | 506 | 53 |
| DD5 | 5.4 | 4.5 | 490 | 34 |
| DD50 | 6.0 | 4.3 | 433 | 27 |
| DD51 | 5.8 | 4.3 | 403 | 26 |
| DD52 | 5.7 | 4.3 | 439 | 29 |
| DD54 | 5.5 | 4.2 | 436 | 28 |
| DD55 | 5.8 | 4.4 | 438 | 30 |
| DD57 | 8.2 | 4.3 | 435 | 29 |
| DD59 | 7.3 | 4.4 | 448 | 31 |
| DD60 | 7.0 | 4.2 | 452 | 33 |
| DD61 | 8.5 | 4.4 | 483 | 51 |
| DD62 | 5.6 | 4.2 | 433 | 31 |
| DD63 | 6.3 | 4.4 | 478 | 35 |
| DD100 | 7.3 | 4.2 | 465 | 26 |
| DD101 | 7.7 | 4.2 | 473 | 29 |
| DD102 | 8.5 | 4.3 | 468 | 28 |
| DD105 | 8.0 | 4.5 | 460 | 30 |

TABLE 3

Structural formulae of the materials used

HTM1

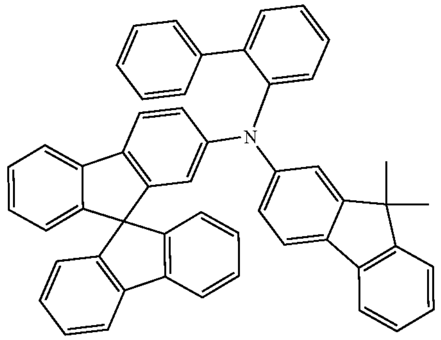

[136463-07-5]

SMB1

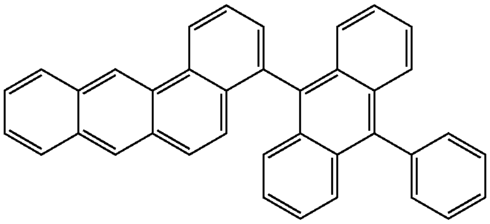

[1087346-88-0]

TABLE 3-continued

Structural formulae of the materials used

SMB2

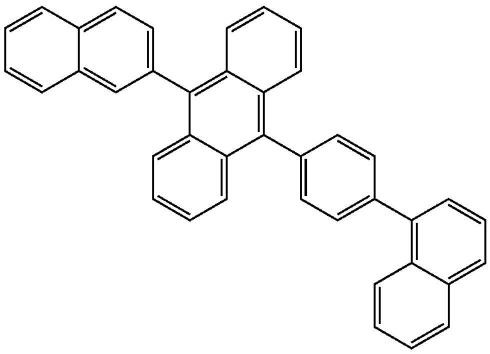

[667940-34-3]

SMB3

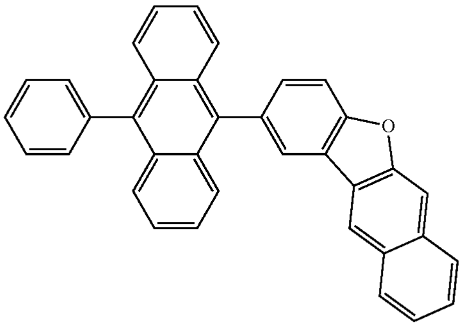

[1627916-48-6]

Ref.-D1

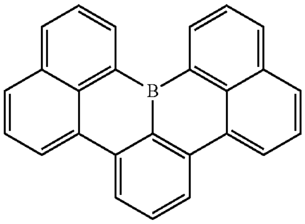

[1809858-60-3]

ETM1

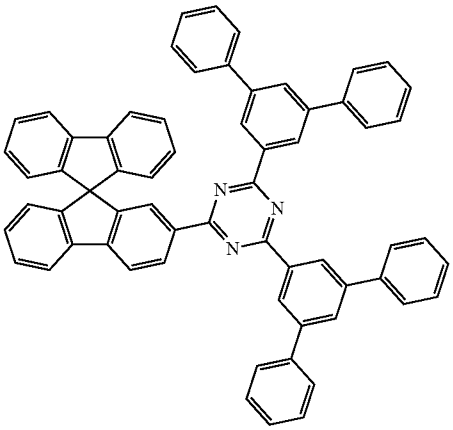

[1233200-52-6]

TABLE 3-continued

Structural formulae of the materials used

ETM2

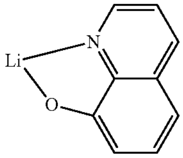

[25387-93-3]

The compounds of the invention, by comparison with the references, show bluer emission, identifiable by the shorter emission wavelength ELmax., combined with narrower electroluminescence spectra, identifiable by the smaller EL-FWHM values (ELectroluminescence—Full Width Half Maximum—width of the EL emission spectra in nm at half the peak height), which leads to distinctly improved color purity (smaller CIE y values). Moreover, EQE values (External Quantum Efficiencies) are distinctly greater and operating voltages are distinctly lower compared to the reference, which leads to a distinct improvement in power efficiencies of the device and hence to lower power consumption.

The invention claimed is:

1. A compound including at least one structure of the formula (Ia) and/or (Ib):

Formula (Ia)

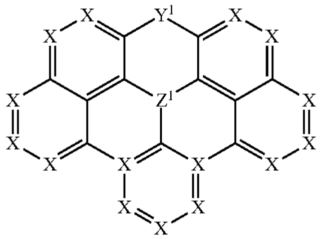

Formula (Ib)

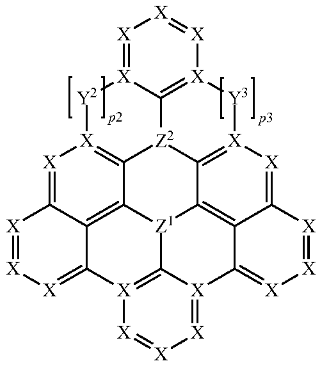

where the symbols and indices used are as follows:

$Z^1$, $Z^2$ is the same or different at each instance and is N, P, B, Al, P(═O), P(═S), or Ga;

$Y^1$, $Y^2$, $Y^3$ is the same or different at each instance and is a bond, N(Ar), N(R), P(Ar), P(R), P(═O)Ar, P(═O)R, P(═S)Ar, P(═S)R, B(Ar), B(R), Al(Ar), Al(R), Ga(Ar), Ga(R), C═O, $C(R)_2$, $Si(R)_2$, C═NR, C═NAr, $C{=}C(R)_2$, O, S, Se, S═O, or $SO_2$;

$p^2$, $p^3$ are the same or different and are 0 or 1;

X is N, CR, or C if a $Y^1$, $Y^2$ or $Y^3$ group binds thereto, with the proviso that not more than two of the X groups in one cycle are N;

R is the same or different at each instance and is H, D, OH, F, Cl, Br, I, CN, $NO_2$, $N(Ar)_2$, $N(R^1)_2$, $C(=O)N(Ar)_2$, $C(=O)N(R^1)_2$, $C(Ar)_3$, $C(R^1)_3$, $Si(Ar)_3$, $Si(R^1)_3$, $B(Ar)_2$, $B(R^1)_2$, $C(=O)Ar$, $C(=O)R^1$, $P(=O)(Ar)_2$, $P(=O)(R^1)_2$, $P(Ar)_2$, $P(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more non-adjacent $CH_2$ groups may be replaced by $R^1C{=}CR^1$, $C{\equiv}C$, $Si(R^1)_2$, C=O, C=S, C=Se, $C{=}NR^1$, —C(=O)O—, $—C(=O)NR^1—$, $NR^1$, $P(=O)(R^1)$, —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R radicals may also together form a ring system;

Ar is the same or different at each instance and is an aromatic or heteroaromatic ring system which has 5 to 60 aromatic ring atoms and may be substituted by one or more $R^1$ radicals; at the same time, it is possible for two Ar radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C=O, $C{=}NR^1$, $C{=}C(R^1)_2$, O, S, S=O, $SO_2$, $N(R^1)$, $P(R^1)$ and $P(=O)R^1$;

$R^1$ is the same or different at each instance and is H, D, F, Cl, Br, I, CN, $NO_2$, $N(Ar')_2$, $N(R^2)_2$, $C(=O)Ar'$, $C(=O)R^2$, $P(=O)(Ar')_2$, $P(Ar')_2$, $B(Ar')_2$, $B(R^2)_2$, $C(Ar')_3$, $C(R^2)_3$, $Si(Ar')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more non-adjacent $CH_2$ groups may be replaced by $—R^2C{=}CR^2—$, $—C{\equiv}C—$, $Si(R^2)_2$, C=O, C=S, C=Se, $C{=}NR^2$, —C(=O)O—, $—C(=O)NR^2—$, $NR^2$, $P(=O)(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent $R^1$ radicals together may form a ring system; at the same time, one or more $R^1$ radicals may form a ring system with a further part of the compound;

Ar' is the same or different at each instance and is an aromatic or heteroaromatic ring system which has 5 to 30 aromatic ring atoms and may be substituted by one or more $R^2$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C=O, $C{=}NR^2$, $C{=}C(R^2)_2$, O, S, S=O, $SO_2$, $N(R^2)$, $P(R^2)$ and $P(=O)R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; or two or more substituents $R^2$ together may form a ring system; and wherein at least two R radicals form a fused ring together with the further groups to which the two R radicals bind, where the two R radicals form at least one structure of the formulae (RA-1) to (RA-12);

where $R^1$ has the definition set out above, the dotted bonds represent the sites of attachment to the atoms of the groups to which the two R radicals bind, and the further symbols have the following definition, Formula RA-1

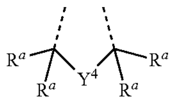

Formula RA-2

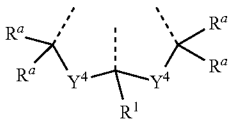

Formula RA-3

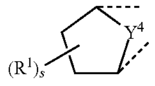

Formula RA-4

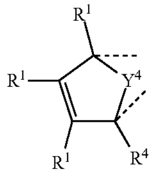

Formula RA-5

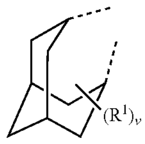

Formula RA-6

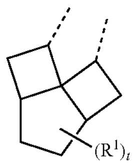

Formula RA-7

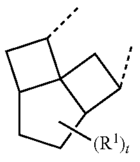

-continued

Formula RA-8

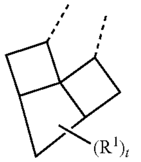

Formula RA-9

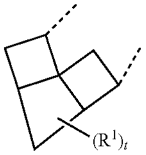

Formula RA-10

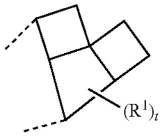

Formula RA-11

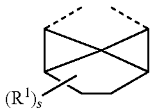

Formula RA-12

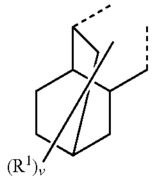

$Y^4$ is the same or different at each instance and is $C(R^1)_2$, $(R^1)_2C—C(R^1)_2$, $(R^1)C═C(R^1)$, $NR^1$, NAr, O or S;

$R^a$ is the same or different at each instance and is F, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more non-adjacent $CH_2$ groups may be replaced by $R^2C═CR^2$, C≡C, $Si(R^2)_2$, C═O, C═S, C═Se, $C═NR^2$, —O(═O)O—, $—C(═O)NR^2—$, $NR^2$, $P(═O)(R^1)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; or two $R^a$ radicals together may form a ring system;

s is 0, 1, 2, 3, 4, 5 or 6;

t is 0, 1, 2, 3, 4, 5, 6, 7 or 8;

v is 0, 1, 2, 3, 4, 5, 6, 7, 8 or 9.

2. A compound as claimed in claim 1, comprising at least one structure of the formulae (IIa), (IIb), (IIc) and (IId):

Formula (IIa)

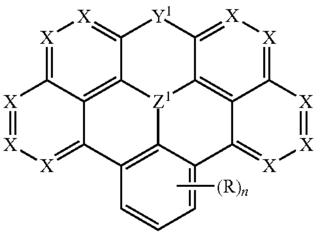

Formula (IIb)

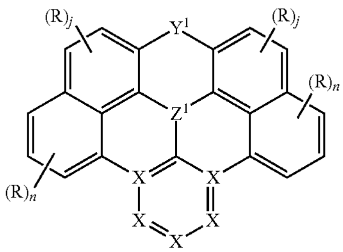

Formula (IIc)

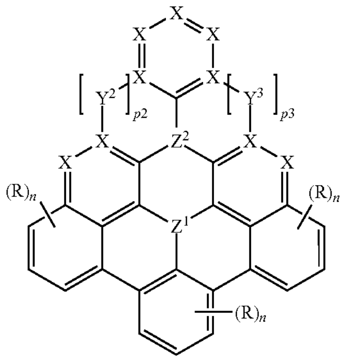

Formula (IId)

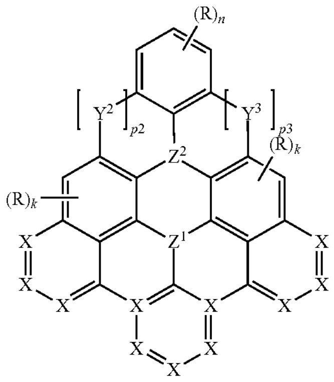

where $p^2$, $p^3$, $Y^1$, $Y^2$, $Y^3$, X, $Z^1$, $Z^2$ and R have the definitions given in claim 1, the index n is 0, 1, 2 or 3, the index j is 0, 1 or 2, and the index k is 0 or 1, where the sum total of the indices k, j and n is 0, 1, 2, 3, 4, 5 or 6.

3. A compound as claimed in claim 1, selected from the compounds of the formulae (IIIa), (IIIb), (IIIc) and (IIId):

Formula (IIIa)

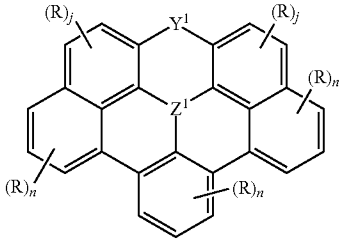

Formula (IIIb)

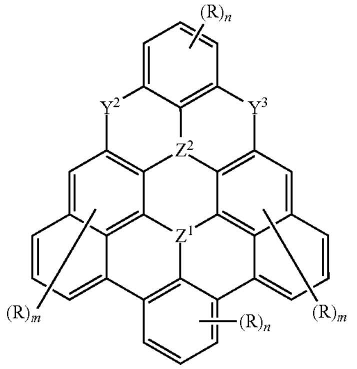

Formula (IIIc)

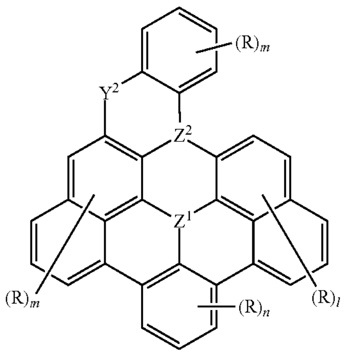

Formula (IIId)

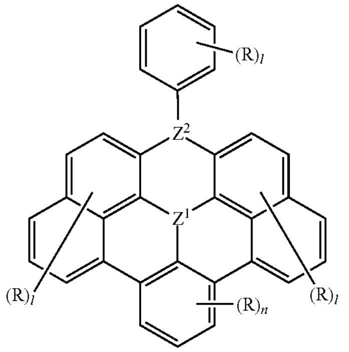

where $Y^1$, Y2, $Y^3$, X, $Z^1$, $Z^2$ and R have the definitions given in claim 1, the index l is 0, 1, 2, 3, 4 or 5, the index m is 0, 1, 2, 3 or 4, and the index n is 0, 1, 2 or 3, where the sum total of the indices l, m and n is 2, 3, 4, 5, 6, 7 or 8, preference being given to structures of the formulae (IIIa) and (IIIb).

4. A compound as claimed in claim 1, wherein, if $Z^1$ is N and $Y^1$ is N(Ar), compounds are excluded in which the Ar group of the N(Ar) radical represented by $Y^1$, together with four R radicals derived from X groups of the ring systems to which the $Y^1$ radical binds, forms an aromatic ring system where any two of the four X groups are adjacent.

5. A compound as claimed in claim 1, wherein $Z^1$ is selected from N and P and the $Y^1$ group is P(=O)Ar, P(=O)R, B(Ar), B(R), Al(Ar), Al(R), Ga(Ar), Ga(R), C=O, S=O or $SO_2$, or that $Z^1$ is selected from N and P and the $Z^2$ group is B, Al, P(=O), P(=S) or Ga, or that $Z^2$ is selected from N and P and at least one of the $Y^2$, $Y^3$ groups is P(=O)Ar, P(=O)R, B(Ar), B(R), Al(Ar), Al(R), Ga(Ar), Ga(R), C=O, S=O or $SO_2$.

6. A compound as claimed in claim 1, wherein $Z^1$ is selected from B, Al, P(=O), P(=S) and Ga and the $Y^1$ group is N(Ar), N(R), P(Ar), P(R), O, S or Se, or that $Z^1$ is selected from B, Al, P(=O), P(=S) and Ga, and the $Z^2$, $Y^3$ group is N or P, or that $Z^2$ is selected from B, Al, P(=O), P(=S) and Ga, and at least one of the $Y^2$, $Y^3$ groups is N(Ar), N(R), P(Ar), P(R), O, S or Se.

7. A compound as claimed in claim 1, that $Z^1$ and/or $Z^2$ is/are B.

8. A compound as claimed in claim 1, that $Z^1$ and/or $Z^2$ is/are N.

9. A compound as claimed in claim 1, that at least two R radicals form a fused ring together with the further groups to which the two R radicals bind, where the two R radicals form of the structures of the formulae (RA-1a) to (RA-4f):

Formula RA-1a

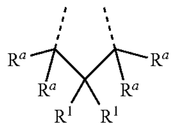

Formula RA-1b

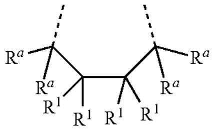

Formula RA-1c

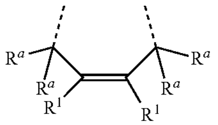

Formula RA-2a

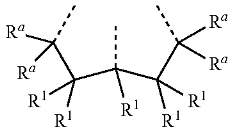

Formula RA-2b

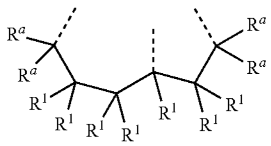

Formula RA-2c

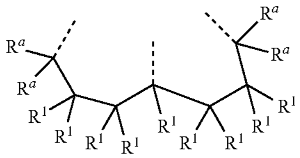

-continued

Formula RA-3a

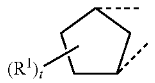

Formula RA-3b

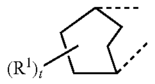

Formula RA-4a

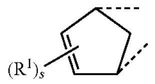

Formula RA-4b

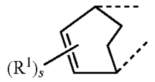

Formula RA-4c

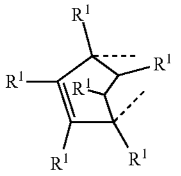

Formula RA-4d

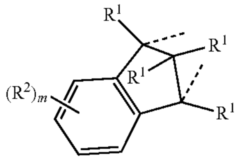

Formula RA-4e

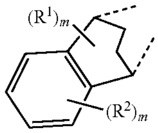

Formula RA-4f

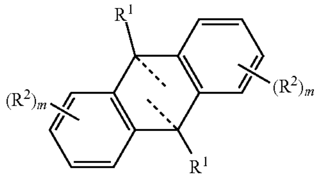

where the index m is 0, 1, 2, 3 or 4, preferably 0, 1 or 2, and the symbols R1, R2, Ra and the indices s and t have the definition set out above, especially in claim 1.

10. A compound as claimed in claim 1, that at least two R radicals form a fused ring together with the further groups to which the two R radicals bind, where the two R radicals form of the structures of the formula (RB):

Formula RB

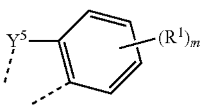

where $R^1$ has the definition set out in claim 1, the index m is 0, 1, 2, 3 or 4, and $Y^5$ is $C(R^1)_2$, $NR^1$, NAr, $BR^1$, BAr, O or S.

11. A compound as claimed in claim 1, comprising at least one structure of the formulae (IVa) to (IVr), where the compounds have at least one fused ring:

Formula (IVa)

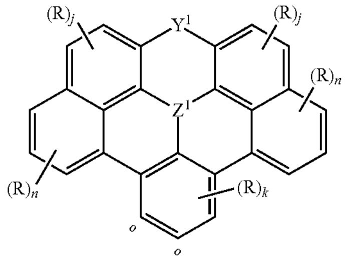

Formula (IVb)

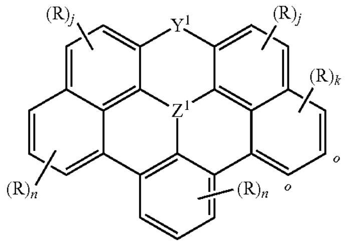

Formula (IVc)

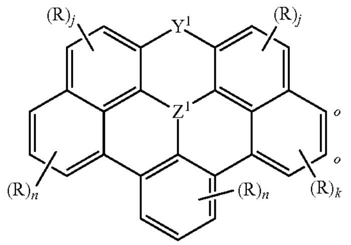

Formula (IVd)

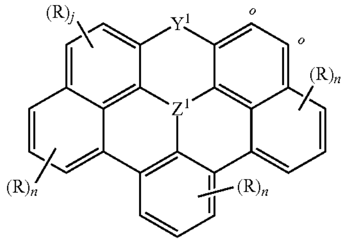

Formula (IVe)

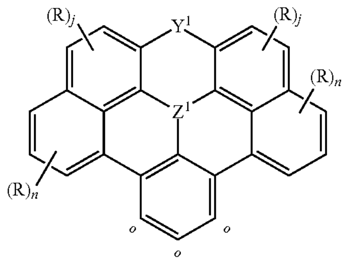

Formula (IVf)

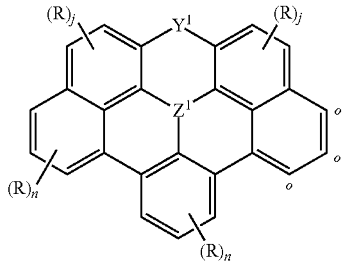

-continued
Formula (IVg)
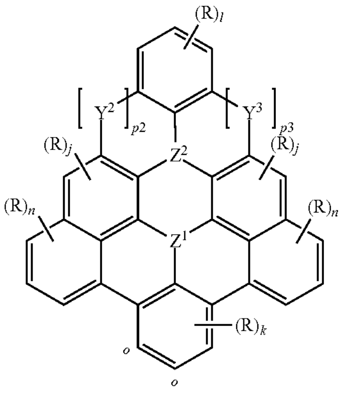
Formula (IVh)
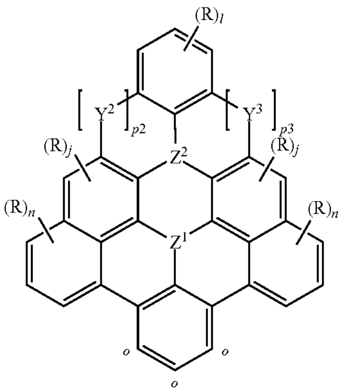
Formula (IVi)
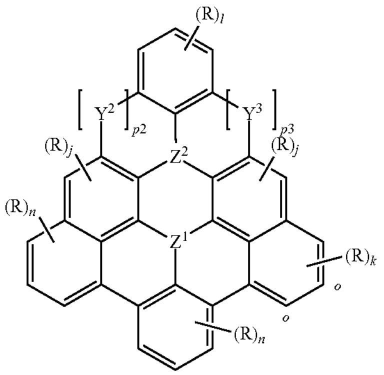
Formula (IVj)
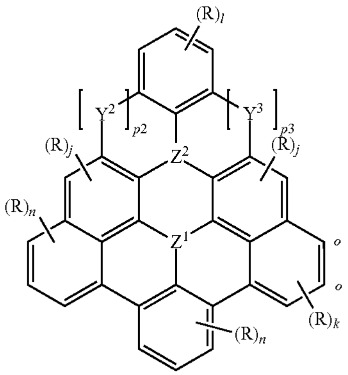
-continued
Formula (IVk)
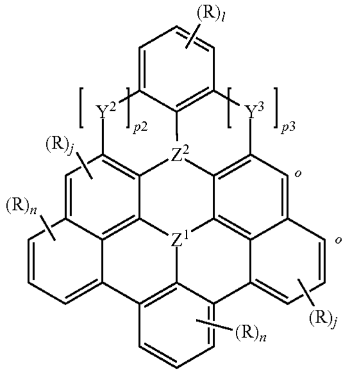
Formula (IVm)
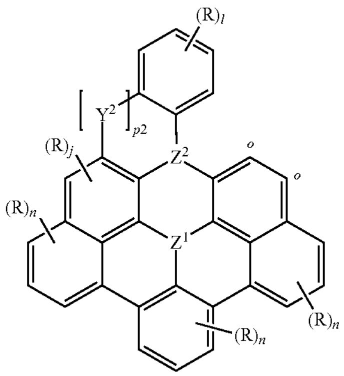
Formula (IVn)
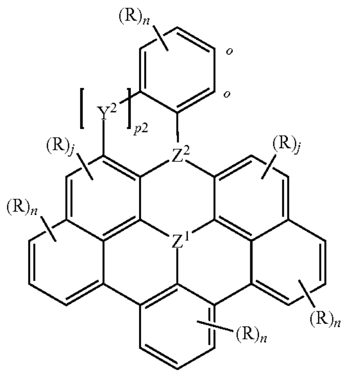
Formula (IVo)
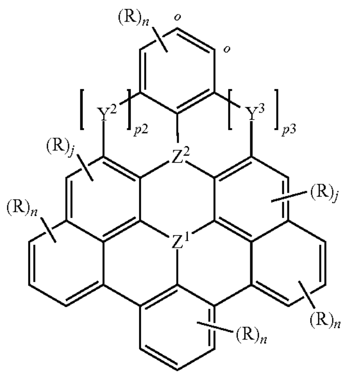

-continued

Formula (IVp)

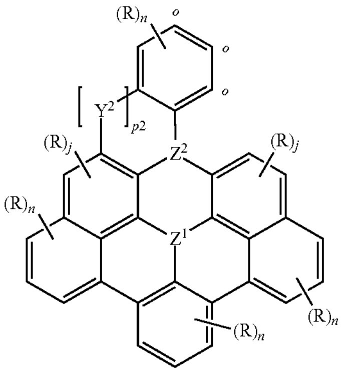

Formula (IVq)

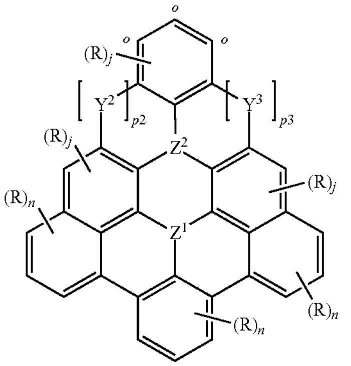

Formula (IVr)

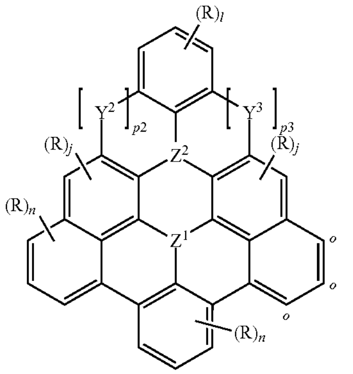

where $Y^1$, $Y^2$, $Y^3$, X, $Z^1$, $Z^2$ and R have the definitions given in claim 1, the symbol o represents the sites of attachment, the index l is 0, 1, 2, 3, 4 or 5, the index m is 0, 1, 2, 3 or 4, the index n is 0, 1, 2 or 3, the index j is 0, 1 or 2, and the index k is 0 or 1, where the sum total of the indices k, j, l, m and n is 0, 1, 2, 3, 4, 5 or 6.

12. A compound as claimed in claim 1, wherein the compounds have at least two fused rings, wherein at least one fused ring is formed by structures of the formulae (RA-1) to (RA-12) and a further ring is formed by structures of the formulae (RA-1) to (RA-12) or (RB), comprising at least one structure of the formulae (Va) to (Vs):

Formula (Va)

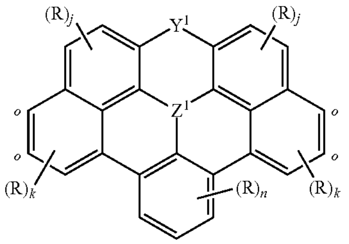

Formula (Vb)

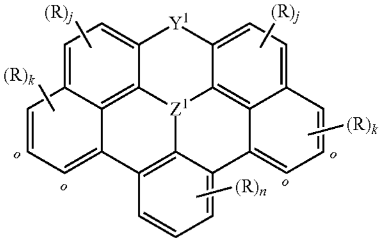

Formula (Vc)

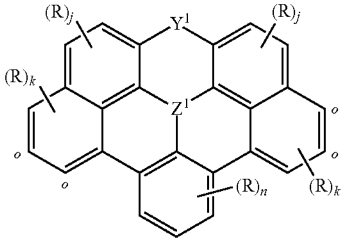

Formula (Vd)

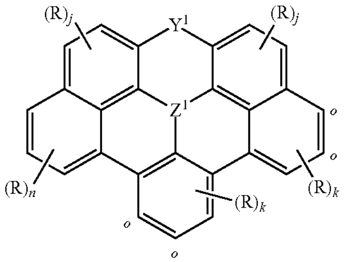

Formula (Ve)

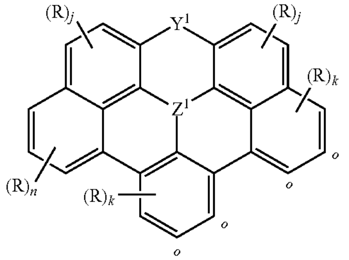

Formula (Vf)

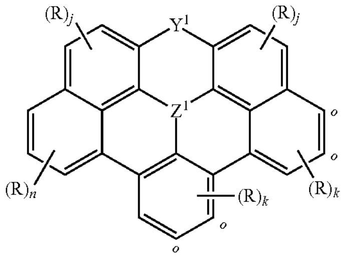

-continued
Formula (Vg)
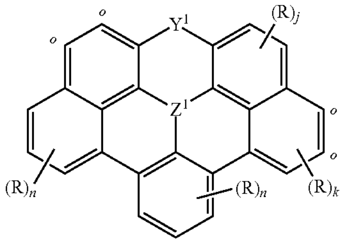
Formula (Vh)
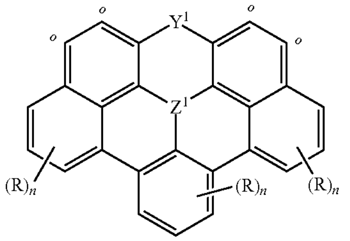
Formula (Vi)
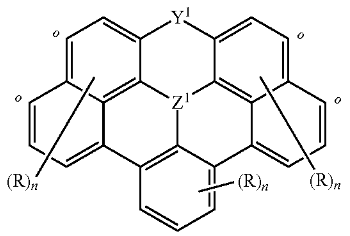
Formula (Vj)
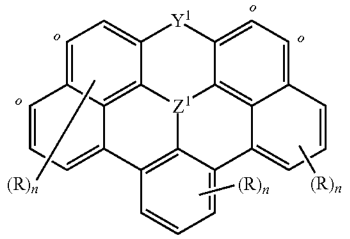
Formula (Vk)
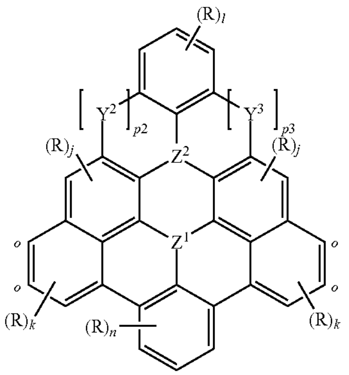
-continued
Formula (Vl)
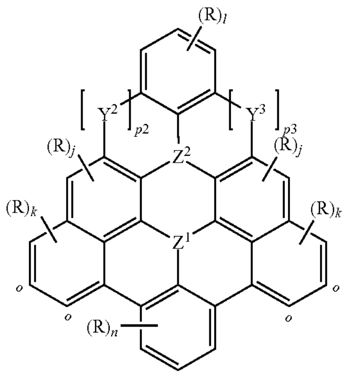
Formula (Vm)
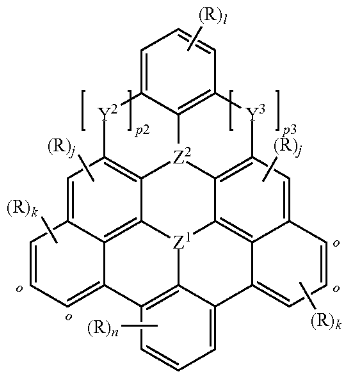
Formula (Vn)
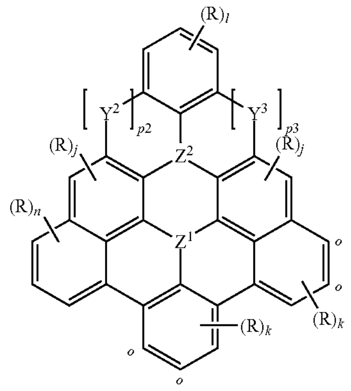
Formula (Vo)
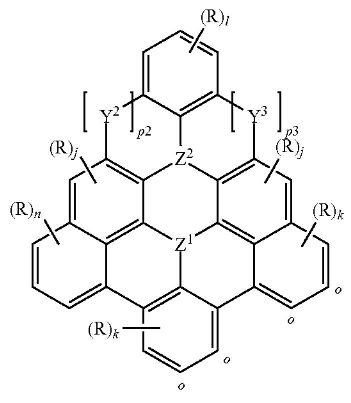

-continued

Formula (Vp)

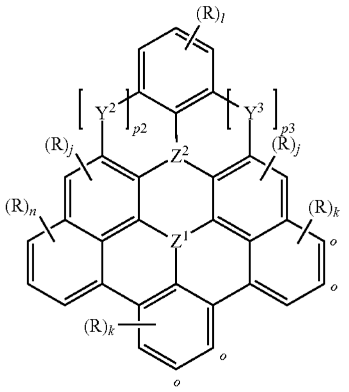

Formula (Vq)

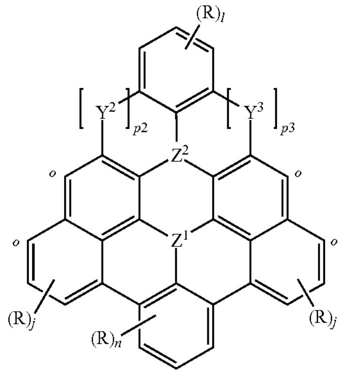

Formula (Vr)

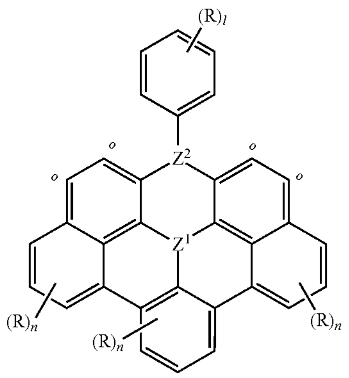

-continued

Formula (Vs)

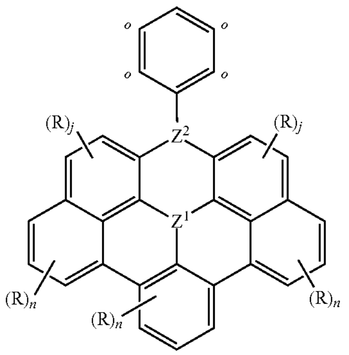

where $Y^1$, $Y^2$, $Y^3$, X, $Z^1$, $Z^2$ and R have the definitions given in claim 1, the symbol o represents the sites of attachment of at least one structure of the formulae (RA-1) to (RA-12) or a structure of the formula (RB), the index l is 0, 1, 2, 3, 4 or 5, the index m is 0, 1, 2, 3 or 4, the index n is 0, 1, 2 or 3, the index j is 0, 1 or 2, and the index k is 0 or 1, where the sum total of the indices k, j, l, m and n is 0, 1, 2, 3 or 4.

13. An oligomer, polymer or dendrimer containing one or more compounds as claimed in claim 1, wherein, rather than a hydrogen atom or a substituent, there are one or more bonds of the compounds to the polymer, oligomer or dendrimer.

14. A formulation comprising at least one compound as claimed in claim 1 and at least one further compound, where the further compound is preferably selected from one or more solvents.

15. A composition comprising at least one compound as claimed in claim 1 and at least one further compound selected from the group consisting of fluorescent emitters, phosphorescent emitters, emitters that exhibit TADF, host materials, electron transport materials, electron injection materials, hole conductor materials, hole injection materials, electron blocker materials and hole blocker materials.

16. A process for preparing a compound as claimed in claim 1, wherein a base skeleton having a $Z^1$ group or a precursor of the $Z^1$ group is synthesized, and then a ring closure reaction is conducted by means of a nucleophilic aromatic substitution reaction or a coupling reaction.

17. A method comprising incorporating the compound as claimed in claim 1 in an electronic device.

18. An electronic device comprising at least one compound as claimed in claim 1, wherein the electronic device is an electroluminescent device.

* * * * *